(12) United States Patent
Gross et al.

(10) Patent No.: US 11,234,692 B2
(45) Date of Patent: Feb. 1, 2022

(54) SELF-RETAINING SYSTEM HAVING LASER-CUT RETAINERS

(71) Applicants: Ethicon, Inc., Somerville, NJ (US); Ethicon LLC, Guaynabo, PR (US)

(72) Inventors: Jeffrey M. Gross, Carlsbad, CA (US); William L. D'Agostino, Hamden, CT (US); Lev Drubetsky, Coquitlam (CA); Alexander Naimagon, Richmond (CA)

(73) Assignee: Cilag GmbH International, Zug (CH)

( * ) Notice: Subject to any disclaimer, the term of this patent is extended or adjusted under 35 U.S.C. 154(b) by 75 days.

(21) Appl. No.: 16/539,263

(22) Filed: Aug. 13, 2019

(65) Prior Publication Data
US 2020/0060679 A1 Feb. 27, 2020

Related U.S. Application Data

(63) Continuation of application No. 13/695,089, filed as application No. PCT/US2011/035271 on May 4, 2011, now Pat. No. 10,420,546.
(Continued)

(51) Int. Cl.
| | |
|---|---|
| *A61B 17/06* | (2006.01) |
| *A61B 17/00* | (2006.01) |
| *B23K 26/14* | (2014.01) |
| *B23K 26/361* | (2014.01) |
| *B23K 26/06* | (2014.01) |

(Continued)

(52) U.S. Cl.
CPC .... *A61B 17/06166* (2013.01); *A61B 17/0401* (2013.01); *B23K 26/032* (2013.01); *B23K 26/0652* (2013.01); *B23K 26/0665* (2013.01); *B23K 26/083* (2013.01); *B23K 26/1462* (2015.10); *B23K 26/361* (2015.10); *B23K 26/362* (2013.01); *B23K 37/04* (2013.01); *A61B 17/0644* (2013.01); *A61B 2017/00526* (2013.01); *A61B 2017/0417* (2013.01); *A61B 2017/0427* (2013.01); *A61B 2017/06038* (2013.01);
(Continued)

(58) Field of Classification Search
CPC .... A61B 17/06166; A61B 2017/06176; A61B 2017/0412; A61B 2017/0427; A61B 17/0401; A61B 2017/00526; B26D 3/08
See application file for complete search history.

(56) References Cited

U.S. PATENT DOCUMENTS

| | | |
|---|---|---|
| 709,392 A | 9/1902 | Brown |
| 733,723 A | 7/1903 | Lukens |

(Continued)

FOREIGN PATENT DOCUMENTS

| | | |
|---|---|---|
| BE | 1014364 | 9/2003 |
| CA | 2309844 | 12/1996 |

(Continued)

OTHER PUBLICATIONS

US 8,663,276 B2, 03/2014, Leung et al. (withdrawn)
(Continued)

*Primary Examiner* — Majid Jamialahmadi
(74) *Attorney, Agent, or Firm* — Frost Brown Todd LLC

(57) ABSTRACT

Self-retaining suture systems including a suture thread bearing a plurality of laser-cut retainers are disclosed. A laser system allows the creation of retainers and self-retaining suture systems in configurations which are difficult and/or impossible to achieve using mechanical cutting technology.

18 Claims, 15 Drawing Sheets

Related U.S. Application Data

(60) Provisional application No. 61/331,294, filed on May 4, 2010, provisional application No. 61/331,302, filed on May 4, 2010.

(51) Int. Cl.
  *B23K 26/08* (2014.01)
  *A61B 17/04* (2006.01)
  *B23K 26/03* (2006.01)
  *B23K 26/362* (2014.01)
  *B23K 37/04* (2006.01)
  *A61B 90/00* (2016.01)
  *A61B 17/064* (2006.01)

(52) U.S. Cl.
  CPC ............... *A61B 2017/06176* (2013.01); *A61B 2090/3937* (2016.02)

(56) References Cited

U.S. PATENT DOCUMENTS

| | | |
|---|---|---|
| 816,026 A | 3/1906 | Meier |
| 1,142,510 A | 6/1915 | Engle |
| 1,728,316 A | 9/1929 | Von Wachenfeldt |
| 1,886,721 A | 11/1932 | O'Brien |
| 2,094,578 A | 10/1937 | Blumenthal et al. |
| 2,201,610 A | 5/1940 | Dawson, Jr. |
| 2,232,142 A | 2/1941 | Schumann |
| 2,254,620 A | 9/1941 | Miller |
| 2,347,956 A | 5/1944 | Lansing |
| 2,355,907 A | 8/1944 | Cox |
| 2,421,193 A | 5/1947 | Gardner |
| 2,452,734 A | 11/1948 | Costelow |
| 2,472,009 A | 5/1949 | Gardner |
| 2,480,271 A | 8/1949 | Sumner |
| 2,572,936 A | 10/1951 | Kulp et al. |
| 2,591,063 A | 4/1952 | Goldberg |
| 2,684,070 A | 7/1954 | Kelsey |
| 2,736,964 A | 3/1956 | Lieberman |
| 2,779,083 A | 1/1957 | Enton |
| 2,817,339 A | 12/1957 | Sullivan |
| 2,830,366 A | 4/1958 | Chisena |
| 2,866,256 A | 12/1958 | Matlin |
| 2,910,067 A | 10/1959 | White |
| 2,928,395 A | 3/1960 | Forbes et al. |
| 2,988,028 A | 6/1961 | Alcamo |
| 3,003,155 A | 10/1961 | Mielzynski et al. |
| 3,066,452 A | 12/1962 | Bott et al. |
| 3,066,673 A | 12/1962 | Bott et al. |
| 3,068,869 A | 12/1962 | Shelden et al. |
| 3,068,870 A | 12/1962 | Levin |
| 3,082,523 A | 3/1963 | Modes et al. |
| 3,123,077 A | 3/1964 | Alcamo |
| 3,166,072 A | 1/1965 | Sullivan, Jr. |
| 3,187,752 A | 6/1965 | Glick |
| 3,206,018 A | 9/1965 | Lewis et al. |
| 3,209,652 A | 10/1965 | Burgsmueller |
| 3,209,754 A | 10/1965 | Brown |
| 3,212,187 A | 10/1965 | Benedict |
| 3,214,810 A | 11/1965 | Mathison |
| 3,221,746 A | 12/1965 | Noble |
| 3,234,636 A | 2/1966 | Brown |
| 3,273,562 A | 9/1966 | Brown |
| 3,352,191 A | 11/1967 | Crawford |
| 3,378,010 A | 4/1968 | Codling |
| 3,385,299 A | 5/1968 | LeRoy |
| 3,452,910 A | 7/1969 | Richter |
| 3,494,006 A | 2/1970 | Brumlik |
| 3,522,637 A | 8/1970 | Brumlik |
| 3,525,340 A | 8/1970 | Gilbert |
| 3,545,608 A | 12/1970 | Berger et al. |
| 3,557,795 A | 1/1971 | Hirsch |
| 3,570,497 A | 3/1971 | Lemole |
| 3,576,284 A | 4/1971 | Fellous et al. |
| 3,586,002 A | 6/1971 | Wood |
| 3,587,974 A | 6/1971 | Rosenkranz et al. |
| 3,608,095 A | 9/1971 | Barry |
| 3,608,539 A | 9/1971 | Miller |
| 3,618,447 A | 11/1971 | Goins |
| 3,646,615 A | 3/1972 | Ness |
| 3,683,926 A | 8/1972 | Suzuki |
| 3,716,058 A | 2/1973 | Tanner, Jr. |
| 3,720,055 A | 3/1973 | de Mestral et al. |
| 3,748,701 A | 7/1973 | de Mestral |
| 3,762,418 A | 10/1973 | Wasson |
| 3,782,617 A | 1/1974 | Gasser et al. |
| 3,825,010 A | 7/1974 | McDonald |
| 3,833,972 A | 9/1974 | Brumlik |
| 3,845,641 A | 11/1974 | Waller |
| 3,847,156 A | 11/1974 | Trumble |
| 3,863,822 A | 2/1975 | Keldany |
| 3,889,322 A | 6/1975 | Brumlik |
| 3,918,455 A | 11/1975 | Coplan |
| 3,922,455 A | 11/1975 | Brumlik |
| 3,941,164 A | 3/1976 | Musgrave |
| 3,977,937 A | 8/1976 | Candor |
| 3,980,177 A | 9/1976 | McGregor |
| 3,981,051 A | 9/1976 | Brumlik |
| 3,981,307 A | 9/1976 | Borysko |
| 3,985,138 A | 10/1976 | Jarvik |
| 3,990,144 A | 11/1976 | Schwartz |
| 4,006,747 A | 2/1977 | Kronenthal |
| 4,008,303 A | 2/1977 | Glick et al. |
| 4,024,871 A | 5/1977 | Stephenson |
| 4,027,608 A | 6/1977 | Arbuckle |
| 4,043,344 A | 8/1977 | Landi |
| 4,052,988 A | 10/1977 | Doddi et al. |
| D246,911 S | 1/1978 | Bess, Jr. et al. |
| 4,069,825 A | 1/1978 | Akiyama |
| 4,073,298 A | 2/1978 | Le Roy |
| 4,075,962 A | 2/1978 | Mabry |
| 4,098,210 A | 7/1978 | Wright |
| 4,137,921 A | 2/1979 | Okuzumi et al. |
| 4,182,340 A | 1/1980 | Spencer |
| 4,186,239 A | 1/1980 | Mize et al. |
| 4,198,734 A | 4/1980 | Brumlik |
| 4,204,541 A | 5/1980 | Kapitanov |
| 4,204,542 A | 5/1980 | Bokros et al. |
| 4,259,959 A | 4/1981 | Walker |
| 4,278,374 A | 7/1981 | Wolosianski |
| 4,300,424 A | 11/1981 | Flinn |
| 4,311,002 A | 1/1982 | Hoffmann et al. |
| 4,313,448 A | 2/1982 | Stokes |
| 4,316,469 A | 2/1982 | Kapitanov |
| 4,317,451 A | 3/1982 | Cerwin et al. |
| 4,372,293 A | 2/1983 | Vijil-Rosales |
| 4,428,376 A | 1/1984 | Mericle |
| 4,430,998 A | 2/1984 | Harvey |
| 4,434,796 A | 3/1984 | Karapetian |
| 4,449,298 A | 5/1984 | Patz |
| 4,454,875 A | 6/1984 | Pratt et al. |
| 4,467,805 A | 8/1984 | Fukuda |
| 4,490,326 A | 12/1984 | Beroff et al. |
| 4,492,075 A | 1/1985 | Faure |
| 4,493,323 A | 1/1985 | Albright et al. |
| 4,505,274 A | 3/1985 | Speelman |
| 4,510,934 A | 4/1985 | Batra |
| 4,531,522 A | 7/1985 | Bedi et al. |
| 4,532,926 A | 8/1985 | O'Holla |
| 4,535,772 A | 8/1985 | Sheehan |
| 4,548,202 A | 10/1985 | Duncan |
| 4,553,544 A | 11/1985 | Nomoto et al. |
| 4,610,250 A | 9/1986 | Green |
| 4,610,251 A | 9/1986 | Kumar |
| 4,635,637 A | 1/1987 | Schreiber |
| 4,637,380 A | 1/1987 | Orejola |
| 4,653,486 A | 3/1987 | Coker |
| 4,669,473 A | 6/1987 | Richards et al. |
| 4,676,245 A | 6/1987 | Fukuda |
| 4,689,882 A | 9/1987 | Lorenz |
| 4,702,250 A | 10/1987 | Ovil et al. |
| 4,712,553 A | 12/1987 | MacGregor |
| 4,719,917 A | 1/1988 | Barrows |
| 4,741,330 A | 5/1988 | Hayhurst |

(56) References Cited

U.S. PATENT DOCUMENTS

| | | |
|---|---|---|
| 4,750,910 A | 6/1988 | Takayanagi et al. |
| 4,776,337 A | 10/1988 | Palmaz |
| 4,832,025 A | 5/1989 | Coates |
| 4,841,960 A | 6/1989 | Garner |
| 4,865,026 A | 9/1989 | Barrett |
| 4,873,976 A | 10/1989 | Schreiber |
| 4,887,601 A | 12/1989 | Richards |
| 4,895,148 A | 1/1990 | Bays et al. |
| 4,898,156 A | 2/1990 | Gatturna et al. |
| 4,899,743 A | 2/1990 | Nicholson et al. |
| 4,900,605 A | 2/1990 | Thorgersen et al. |
| 4,905,367 A | 3/1990 | Pinchuck et al. |
| 4,930,945 A | 6/1990 | Arai et al. |
| 4,932,962 A | 6/1990 | Yoon et al. |
| 4,946,468 A | 8/1990 | Li |
| 4,948,444 A | 8/1990 | Schultz et al. |
| 4,950,258 A | 8/1990 | Kawai et al. |
| 4,950,285 A | 8/1990 | Wilk |
| 4,968,315 A | 11/1990 | Gatturna |
| 4,976,715 A | 12/1990 | Bays et al. |
| 4,979,956 A | 12/1990 | Silvestrini et al. |
| 4,981,149 A | 1/1991 | Yoon |
| 4,994,073 A | 2/1991 | Green |
| 4,994,084 A | 2/1991 | Brennan |
| 4,997,439 A | 3/1991 | Chen |
| 5,002,550 A | 3/1991 | Li |
| 5,002,562 A | 3/1991 | Oberlander |
| 5,007,921 A | 4/1991 | Brown |
| 5,007,922 A | 4/1991 | Chen et al. |
| 5,026,390 A | 6/1991 | Brown |
| 5,037,422 A | 8/1991 | Hayhurst et al. |
| 5,037,433 A | 8/1991 | Wilk et al. |
| 5,041,129 A | 8/1991 | Hayhurst et al. |
| 5,046,513 A | 9/1991 | Gatturna et al. |
| 5,047,047 A | 9/1991 | Yoon |
| 5,053,047 A | 10/1991 | Yoon |
| 5,084,063 A | 1/1992 | Korthoff |
| 5,089,010 A | 2/1992 | Korthoff |
| 5,102,418 A | 4/1992 | Granger et al. |
| 5,102,421 A | 4/1992 | Anpach, Jr. |
| 5,103,073 A | 4/1992 | Danilov et al. |
| 5,112,344 A | 5/1992 | Petros |
| 5,123,911 A | 6/1992 | Granger et al. |
| 5,123,913 A | 6/1992 | Wilk et al. |
| 5,123,919 A | 6/1992 | Sauter et al. |
| 5,127,413 A | 7/1992 | Ebert |
| 5,133,738 A | 7/1992 | Korthoff et al. |
| 5,141,520 A | 8/1992 | Goble et al. |
| 5,147,382 A | 9/1992 | Gertzman et al. |
| 5,156,615 A | 10/1992 | Korthoff et al. |
| 5,156,788 A | 10/1992 | Chesterfield et al. |
| 5,176,692 A | 1/1993 | Wilk et al. |
| 5,179,964 A | 1/1993 | Cook |
| 5,192,274 A | 3/1993 | Bierman |
| 5,192,302 A | 3/1993 | Kensey et al. |
| 5,192,303 A | 3/1993 | Gatturna et al. |
| 5,197,597 A | 3/1993 | Leary et al. |
| 5,201,326 A | 4/1993 | Kubicki et al. |
| 5,207,679 A | 5/1993 | Li |
| 5,207,694 A | 5/1993 | Broome |
| 5,217,486 A | 6/1993 | Rice et al. |
| 5,217,494 A | 6/1993 | Coggins et al. |
| 5,222,508 A | 6/1993 | Contarini |
| 5,222,976 A | 6/1993 | Yoon |
| 5,224,946 A | 7/1993 | Hayhurst et al. |
| 5,226,459 A | 7/1993 | De Ro et al. |
| 5,234,006 A | 8/1993 | Eaton et al. |
| 5,242,457 A | 9/1993 | Akopov et al. |
| 5,246,441 A | 9/1993 | Ross et al. |
| 5,259,846 A | 11/1993 | Granger et al. |
| 5,263,973 A | 11/1993 | Cook |
| 5,269,783 A | 12/1993 | Sander |
| 5,282,832 A | 2/1994 | Toso et al. |
| 5,292,326 A | 3/1994 | Green |
| 5,306,288 A | 4/1994 | Granger et al. |
| 5,306,290 A | 4/1994 | Martins et al. |
| 5,312,422 A | 5/1994 | Trott |
| 5,320,629 A | 6/1994 | Noda et al. |
| 5,330,488 A | 7/1994 | Goldrath |
| 5,330,503 A | 7/1994 | Yoon |
| 5,342,376 A | 8/1994 | Ruff |
| 5,342,395 A | 8/1994 | Jarrett et al. |
| 5,350,385 A | 9/1994 | Christy |
| 5,352,515 A | 10/1994 | Jarrett et al. |
| 5,354,271 A | 10/1994 | Voda |
| 5,354,298 A | 10/1994 | Lee et al. |
| 5,358,511 A | 10/1994 | Gatturna et al. |
| 5,363,556 A | 11/1994 | Banholzer et al. |
| 5,372,146 A | 12/1994 | Branch |
| 5,374,268 A | 12/1994 | Sander |
| 5,374,278 A | 12/1994 | Chesterfield et al. |
| 5,380,334 A | 1/1995 | Torrie et al. |
| 5,387,383 A | 2/1995 | Collier et al. |
| 5,391,173 A | 2/1995 | Wilk |
| 5,403,346 A | 4/1995 | Loeser |
| 5,411,523 A | 5/1995 | Goble |
| 5,414,988 A | 5/1995 | DiPalma et al. |
| 5,417,691 A | 5/1995 | Hayhurst |
| 5,425,746 A | 6/1995 | Proto et al. |
| 5,425,747 A | 6/1995 | Brotz |
| 5,437,680 A | 8/1995 | Yoon et al. |
| 5,450,860 A | 9/1995 | O'Connor |
| 5,451,461 A | 9/1995 | Broyer |
| 5,462,561 A | 10/1995 | Voda |
| 5,464,422 A | 11/1995 | Silverman |
| 5,464,426 A | 11/1995 | Bonutti |
| 5,464,427 A | 11/1995 | Curtis et al. |
| 5,472,452 A | 12/1995 | Trott |
| 5,478,353 A | 12/1995 | Yoon |
| 5,480,403 A | 1/1996 | Lee et al. |
| 5,480,411 A | 1/1996 | Liu et al. |
| 5,484,451 A | 1/1996 | Akopov et al. |
| 5,486,197 A | 1/1996 | Le et al. |
| 5,500,000 A | 3/1996 | Feagin et al. |
| 5,500,991 A | 3/1996 | Demarest et al. |
| 5,520,084 A | 5/1996 | Chesterfield et al. |
| 5,520,691 A | 5/1996 | Branch |
| 5,522,845 A | 6/1996 | Wenstrom, Jr. |
| 5,527,342 A | 6/1996 | Pietrzak et al. |
| 5,531,760 A | 7/1996 | Alwafaie |
| 5,531,761 A | 7/1996 | Yoon |
| 5,531,790 A | 7/1996 | Frechet et al. |
| 5,536,582 A | 7/1996 | Prasad et al. |
| 5,540,705 A | 7/1996 | Meade et al. |
| 5,540,718 A | 7/1996 | Bartlett |
| 5,545,148 A | 8/1996 | Wurster |
| 5,549,631 A | 8/1996 | Bonutti |
| 5,554,171 A | 9/1996 | Gatturna et al. |
| 5,569,272 A | 10/1996 | Reed et al. |
| 5,571,139 A | 11/1996 | Jenkins, Jr. |
| 5,571,175 A | 11/1996 | Vanney et al. |
| 5,571,216 A | 11/1996 | Anderson |
| 5,573,543 A | 11/1996 | Akopov et al. |
| 5,584,859 A | 12/1996 | Brotz |
| 5,593,424 A | 1/1997 | Northrup, III et al. |
| 5,601,557 A | 2/1997 | Hayhurst |
| 5,626,590 A | 5/1997 | Wilk |
| 5,626,611 A | 5/1997 | Liu et al. |
| 5,632,753 A | 5/1997 | Loeser |
| 5,643,288 A | 7/1997 | Thompson |
| 5,643,295 A | 7/1997 | Yoon |
| 5,643,319 A | 7/1997 | Green et al. |
| 5,645,568 A | 7/1997 | Chervitz et al. |
| 5,647,874 A | 7/1997 | Hayhurst |
| 5,649,939 A | 7/1997 | Reddick |
| 5,653,716 A | 8/1997 | Malo et al. |
| 5,662,654 A | 9/1997 | Thompson |
| 5,662,714 A | 9/1997 | Charvin et al. |
| 5,669,935 A | 9/1997 | Rosenman et al. |
| D386,583 S | 11/1997 | Ferragamo et al. |
| 5,676,675 A | 11/1997 | Grice |
| 5,683,417 A | 11/1997 | Cooper |
| D387,161 S | 12/1997 | Ferragamo et al. |
| 5,693,072 A | 12/1997 | McIntosh |

(56) References Cited

U.S. PATENT DOCUMENTS

| | | |
|---|---|---|
| 5,695,879 A | 12/1997 | Goldmann et al. |
| 5,697,976 A | 12/1997 | Chesterfield et al. |
| 5,702,397 A | 12/1997 | Goble et al. |
| 5,702,462 A | 12/1997 | Oberlander |
| 5,709,692 A | 1/1998 | Mollenauer et al. |
| 5,716,358 A | 2/1998 | Ochoa et al. |
| 5,716,376 A | 2/1998 | Roby et al. |
| 5,722,991 A | 3/1998 | Colligan |
| 5,723,008 A | 3/1998 | Gordon |
| 5,725,557 A | 3/1998 | Gatturna et al. |
| 5,728,114 A | 3/1998 | Evans et al. |
| 5,731,855 A | 3/1998 | Koyama et al. |
| 5,741,277 A | 4/1998 | Gordon et al. |
| 5,744,151 A | 4/1998 | Capelli |
| 5,746,072 A | 5/1998 | Bohnke |
| 5,763,411 A | 6/1998 | Edwardson et al. |
| 5,765,560 A | 6/1998 | Verkerke et al. |
| 5,766,246 A | 6/1998 | Mullhauser et al. |
| 5,779,719 A | 7/1998 | Klein et al. |
| 5,782,864 A | 7/1998 | Lizardi |
| 5,807,403 A | 9/1998 | Beyar et al. |
| 5,807,406 A | 9/1998 | Brauker et al. |
| 5,810,853 A | 9/1998 | Yoon |
| 5,814,051 A | 9/1998 | Wenstrom, Jr. |
| 5,843,087 A | 12/1998 | Jensen et al. |
| 5,843,178 A | 12/1998 | Vanney et al. |
| 5,855,619 A | 1/1999 | Caplan et al. |
| 5,863,360 A | 1/1999 | Wood et al. |
| 5,887,594 A | 3/1999 | LoCicero, III |
| 5,891,166 A | 4/1999 | Schervinsky |
| 5,893,856 A | 4/1999 | Jacob et al. |
| 5,895,395 A | 4/1999 | Yeung |
| 5,895,413 A | 4/1999 | Nordstrom |
| 5,897,572 A | 4/1999 | Schulsinger et al. |
| 5,899,911 A | 5/1999 | Carter |
| 5,916,224 A | 6/1999 | Esplin |
| 5,919,234 A | 7/1999 | Lemperle et al. |
| 5,925,078 A | 7/1999 | Anderson |
| 5,931,855 A | 8/1999 | Buncke |
| 5,938,668 A | 8/1999 | Scirica et al. |
| 5,941,899 A | 8/1999 | Granger et al. |
| 5,950,633 A | 9/1999 | Lynch et al. |
| 5,954,747 A | 9/1999 | Clark |
| 5,964,765 A | 10/1999 | Fenton, Jr. et al. |
| 5,964,783 A | 10/1999 | Grafton et al. |
| 5,968,097 A | 10/1999 | Frechet et al. |
| 5,972,024 A | 10/1999 | Northrup, III et al. |
| 5,984,933 A | 11/1999 | Yoon |
| 5,993,459 A | 11/1999 | Larsen et al. |
| 5,997,554 A | 12/1999 | Thompson |
| 6,001,111 A | 12/1999 | Sepetka et al. |
| 6,012,216 A | 1/2000 | Esteves et al. |
| 6,015,410 A | 1/2000 | Tormala et al. |
| 6,024,757 A | 2/2000 | Haase et al. |
| 6,027,523 A | 2/2000 | Schmieding |
| 6,039,741 A | 3/2000 | Meislin |
| 6,042,583 A | 3/2000 | Thompson et al. |
| 6,045,571 A | 4/2000 | Hill et al. |
| 6,056,778 A | 5/2000 | Grafton et al. |
| 6,063,105 A | 5/2000 | Totakura |
| 6,071,292 A | 6/2000 | Makower et al. |
| 6,074,419 A | 6/2000 | Healy et al. |
| 6,076,255 A | 6/2000 | Shikakubo et al. |
| 6,083,244 A | 7/2000 | Lubbers et al. |
| 6,102,947 A | 8/2000 | Gordon |
| 6,106,544 A | 8/2000 | Brazeau |
| 6,106,545 A | 8/2000 | Egan |
| 6,110,484 A | 8/2000 | Sierra |
| 6,129,741 A | 10/2000 | Wurster et al. |
| D433,753 S | 11/2000 | Weiss |
| 6,146,406 A | 11/2000 | Shluzas et al. |
| 6,146,407 A | 11/2000 | Krebs |
| 6,149,660 A | 11/2000 | Laufer et al. |
| 6,159,234 A | 12/2000 | Bonutti et al. |
| 6,160,084 A | 12/2000 | Langer et al. |
| 6,163,948 A | 12/2000 | Esteves et al. |
| 6,165,203 A | 12/2000 | Krebs |
| 6,168,633 B1 | 1/2001 | Shoher et al. |
| 6,174,324 B1 | 1/2001 | Egan et al. |
| 6,183,499 B1 | 2/2001 | Fischer et al. |
| 6,187,095 B1 | 2/2001 | Labrecque et al. |
| 6,203,565 B1 | 3/2001 | Bonutti et al. |
| 6,206,908 B1 | 3/2001 | Roby |
| 6,214,030 B1 | 4/2001 | Matsutani et al. |
| 6,231,911 B1 | 5/2001 | Steinback et al. |
| 6,235,869 B1 | 5/2001 | Roby et al. |
| 6,241,747 B1 | 6/2001 | Ruff |
| 6,251,143 B1 | 6/2001 | Schwartz et al. |
| 6,264,675 B1 | 7/2001 | Brotz |
| 6,267,772 B1 | 7/2001 | Mulhauser et al. |
| 6,270,517 B1 | 8/2001 | Brotz |
| 6,315,788 B1 | 11/2001 | Roby |
| 6,319,231 B1 | 11/2001 | Andrulitis |
| 6,322,581 B1 | 11/2001 | Fukuda et al. |
| 6,334,865 B1 | 1/2002 | Redmond et al. |
| 6,383,201 B1 | 5/2002 | Dong |
| 6,387,363 B1 | 5/2002 | Gruskin |
| 6,388,043 B1 | 5/2002 | Langer et al. |
| 6,395,029 B1 | 5/2002 | Levy |
| D462,766 S | 9/2002 | Jacobs et al. |
| 6,443,962 B1 | 9/2002 | Gaber |
| 6,471,715 B1 | 10/2002 | Weiss |
| 6,478,809 B1 | 11/2002 | Brotz |
| 6,485,503 B2 | 11/2002 | Jacobs et al. |
| 6,491,701 B2 | 12/2002 | Tierney et al. |
| 6,491,714 B1 | 12/2002 | Bennett |
| 6,494,898 B1 | 12/2002 | Roby et al. |
| 6,495,127 B1 | 12/2002 | Wallace et al. |
| RE37,963 E | 1/2003 | Thal |
| 6,506,190 B1 | 1/2003 | Walshe |
| 6,506,197 B1 | 1/2003 | Rollero et al. |
| 6,508,833 B2 | 1/2003 | Pavcnik et al. |
| 6,511,488 B1 | 1/2003 | Marshall et al. |
| 6,514,265 B2 | 2/2003 | Ho et al. |
| 6,527,795 B1 | 3/2003 | Lizardi |
| 6,575,976 B2 | 3/2003 | Grafton |
| 6,548,002 B2 | 4/2003 | Gresser et al. |
| 6,548,569 B1 | 4/2003 | Williams et al. |
| 6,551,343 B1 | 4/2003 | Tormala et al. |
| 6,554,802 B1 | 4/2003 | Pearson et al. |
| 6,565,597 B1 | 5/2003 | Fearnot et al. |
| 6,592,609 B1 | 7/2003 | Bonutti |
| 6,592,625 B2 | 7/2003 | Cauthen |
| 6,596,296 B1 | 7/2003 | Nelson et al. |
| 6,599,310 B2 | 7/2003 | Leung et al. |
| 6,607,541 B1 | 8/2003 | Gardiner et al. |
| 6,610,078 B1 | 8/2003 | Bru-Magniez et al. |
| 6,613,059 B2 | 9/2003 | Schaller et al. |
| 6,613,254 B1 | 9/2003 | Shiffer |
| 6,616,982 B2 | 9/2003 | Merrill et al. |
| 6,623,492 B1 | 9/2003 | Berube et al. |
| 6,626,930 B1 | 9/2003 | Allen et al. |
| 6,632,245 B2 | 10/2003 | Kim |
| 6,641,592 B1 | 11/2003 | Sauer et al. |
| 6,641,593 B1 | 11/2003 | Schaller et al. |
| 6,645,226 B1 | 11/2003 | Jacobs et al. |
| 6,645,227 B2 | 11/2003 | Fallin et al. |
| 6,648,921 B2 | 11/2003 | Anderson et al. |
| 6,656,182 B1 | 12/2003 | Hayhurst |
| 6,689,153 B1 | 2/2004 | Skiba |
| 6,689,166 B2 | 2/2004 | Laurencin et al. |
| 6,692,761 B2 | 2/2004 | Mahmood et al. |
| 6,698,639 B1 | 3/2004 | Otomo et al. |
| 6,702,844 B1 | 3/2004 | Lazarus |
| 6,712,830 B2 | 3/2004 | Esplin |
| 6,712,838 B2 | 3/2004 | D'Aversa et al. |
| 6,712,859 B2 | 3/2004 | Rousseau et al. |
| 6,716,234 B2 | 4/2004 | Grafton et al. |
| 6,720,402 B2 | 4/2004 | Langer et al. |
| 6,726,705 B2 | 4/2004 | Peterson et al. |
| 6,746,443 B1 | 6/2004 | Morley et al. |
| 6,746,458 B1 | 6/2004 | Cloud |
| 6,749,616 B1 | 6/2004 | Nath |
| 6,756,000 B2 | 6/2004 | Antal et al. |

(56) References Cited

U.S. PATENT DOCUMENTS

| | | | |
|---|---|---|---|
| 6,773,450 B2 | 8/2004 | Leung et al. |
| 6,776,340 B2 | 8/2004 | Murokh et al. |
| 6,776,789 B2 | 8/2004 | Bryant et al. |
| 6,783,554 B2 | 8/2004 | Amara et al. |
| 6,814,748 B1 | 11/2004 | Baker et al. |
| 6,818,010 B2 | 11/2004 | Eichhorn et al. |
| 6,838,493 B2 | 1/2005 | Williams et al. |
| 6,848,152 B2 | 2/2005 | Genova et al. |
| 6,852,825 B2 | 2/2005 | Ledlein et al. |
| 6,858,222 B2 | 2/2005 | Nelson et al. |
| 6,860,891 B2 | 3/2005 | Schulze |
| 6,860,901 B1 | 3/2005 | Baker et al. |
| 6,867,248 B1 | 3/2005 | Martin et al. |
| 6,877,934 B2 | 4/2005 | Gainer |
| 6,881,766 B2 | 4/2005 | Hain |
| 6,893,452 B2 | 5/2005 | Jacobs |
| 6,905,484 B2 | 6/2005 | Buckman et al. |
| 6,911,035 B1 | 6/2005 | Blomme |
| 6,911,037 B2 | 6/2005 | Gainor et al. |
| 6,913,607 B2 | 7/2005 | Ainsworth et al. |
| 6,915,623 B2 | 7/2005 | Dey et al. |
| 6,921,811 B2 | 7/2005 | Zamora et al. |
| 6,923,819 B2 | 8/2005 | Meade et al. |
| 6,945,021 B2 | 9/2005 | Michel |
| 6,945,980 B2 | 9/2005 | Nguyen et al. |
| 6,951,565 B2 | 10/2005 | Keane et al. |
| 6,960,221 B2 | 11/2005 | Ho et al. |
| 6,960,233 B1 | 11/2005 | Berg et al. |
| 6,974,450 B2 | 12/2005 | Weber et al. |
| 6,981,983 B1 | 1/2006 | Rosenblatt et al. |
| 6,984,241 B2 | 1/2006 | Lubbers et al. |
| 6,986,780 B2 | 1/2006 | Rudnick et al. |
| 6,991,643 B2 | 1/2006 | Saadat |
| 6,996,880 B2 | 2/2006 | Kurtz, Jr. |
| 7,004,970 B2 | 2/2006 | Cauthen, III et al. |
| 7,021,316 B2 | 4/2006 | Leiboff |
| 7,026,437 B2 | 4/2006 | Shalaby et al. |
| 7,029,490 B2 | 4/2006 | Grafton et al. |
| 7,033,379 B2 | 4/2006 | Peterson |
| 7,037,984 B2 | 5/2006 | Ledlein et al. |
| 7,048,748 B1 | 5/2006 | Ustuner |
| 7,056,331 B2 | 6/2006 | Kaplan et al. |
| 7,056,333 B2 | 6/2006 | Walshe |
| 7,057,135 B2 | 6/2006 | Li |
| 7,063,716 B2 | 6/2006 | Cunningham |
| 7,070,610 B2 | 7/2006 | Im et al. |
| 7,070,858 B2 | 7/2006 | Shalaby et al. |
| 7,074,117 B2 | 7/2006 | Dore |
| 7,081,135 B2 | 7/2006 | Smith et al. |
| 7,083,637 B1 | 8/2006 | Tannhauser |
| 7,083,648 B2 | 8/2006 | Yu et al. |
| 7,101,504 B2 | 9/2006 | Suzuki |
| 7,107,090 B2 | 9/2006 | Salisbury, Jr. et al. |
| 7,112,207 B2 | 9/2006 | Allen et al. |
| 7,112,214 B2 | 9/2006 | Peterson et al. |
| 7,125,403 B2 | 10/2006 | Julian et al. |
| 7,125,413 B2 | 10/2006 | Grigoryants et al. |
| D532,107 S | 11/2006 | Peterson et al. |
| 7,138,441 B1 | 11/2006 | Zhang |
| 7,141,302 B2 | 11/2006 | Mueller et al. |
| 7,144,401 B2 | 12/2006 | Yamamoto et al. |
| 7,144,412 B2 | 12/2006 | Wolf et al. |
| 7,144,415 B2 | 12/2006 | DelRio et al. |
| 7,150,712 B2 | 12/2006 | Buehlmann et al. |
| 7,150,757 B2 | 12/2006 | Fallin et al. |
| 7,152,605 B2 | 12/2006 | Khairkhahan et al. |
| 7,156,858 B2 | 1/2007 | Shuldt-Hempe et al. |
| 7,156,862 B2 | 1/2007 | Jacobs et al. |
| 7,160,312 B2 | 1/2007 | Saadat |
| 7,172,595 B1 | 2/2007 | Goble |
| 7,172,615 B2 | 2/2007 | Morriss et al. |
| 7,186,262 B2 | 3/2007 | Saadat |
| 7,195,634 B2 | 3/2007 | Schmieding et al. |
| 7,211,088 B2 | 5/2007 | Grafton et al. |
| 7,214,230 B2 | 5/2007 | Brock et al. |
| 7,217,744 B2 | 5/2007 | Lendlein et al. |
| 7,225,512 B2 | 6/2007 | Genova et al. |
| 7,226,468 B2 | 6/2007 | Ruff |
| 7,232,447 B2 | 6/2007 | Gellman et al. |
| 7,244,270 B2 | 7/2007 | Lesh et al. |
| 7,279,612 B1 | 10/2007 | Heaton et al. |
| 7,294,357 B2 | 11/2007 | Roby |
| 7,297,142 B2 | 11/2007 | Brock |
| 7,322,105 B2 | 1/2008 | Lewis |
| 7,329,271 B2 | 2/2008 | Koyfman et al. |
| 7,351,250 B2 | 4/2008 | Zamierowski |
| 7,357,810 B2 | 4/2008 | Koyfman et al. |
| 7,371,253 B2 | 5/2008 | Leung et al. |
| 7,381,211 B2 | 6/2008 | Zamierowski |
| 7,387,634 B2 | 6/2008 | Benderev |
| 7,410,495 B2 | 8/2008 | Zamierowski |
| 7,413,570 B2 | 8/2008 | Zamierowski |
| 7,413,571 B2 | 8/2008 | Zamierowski |
| 7,416,556 B2 | 8/2008 | Jackson |
| 7,425,200 B2 | 9/2008 | Brockway et al. |
| 7,445,626 B2 | 11/2008 | Songer et al. |
| 7,452,371 B2 | 11/2008 | Pavcnik et al. |
| 7,467,710 B2 | 12/2008 | Cerwin et al. |
| 7,468,068 B2 | 12/2008 | Kolster |
| 7,481,826 B2 | 1/2009 | Cichocki, Jr. |
| 7,491,214 B2 | 2/2009 | Greene, Jr. et al. |
| 7,510,566 B2 | 3/2009 | Jacobs et al. |
| 7,513,904 B2 | 4/2009 | Sulamanidze et al. |
| 7,547,315 B2 | 6/2009 | Peterson et al. |
| 7,547,316 B2 | 6/2009 | Priewe et al. |
| 7,572,275 B2 | 8/2009 | Fallin et al. |
| 7,582,105 B2 | 9/2009 | Kolster |
| 7,591,850 B2 | 9/2009 | Cavazzoni |
| 7,601,164 B2 | 10/2009 | Wu |
| 7,611,521 B2 | 11/2009 | Lubbers et al. |
| 7,615,076 B2 | 11/2009 | Cauthen, III et al. |
| 7,624,487 B2 | 12/2009 | Trull et al. |
| 7,641,672 B2 | 1/2010 | Fallin et al. |
| 7,641,825 B2 | 1/2010 | Rizk |
| 7,645,293 B2 | 1/2010 | Martinek et al. |
| 7,678,134 B2 | 3/2010 | Schmieding et al. |
| 7,682,374 B2 | 3/2010 | Foerster et al. |
| 7,686,200 B2 | 3/2010 | Peterson |
| 7,691,112 B2 | 4/2010 | Chanduszko et al. |
| 7,708,759 B2 | 5/2010 | Lubbers et al. |
| 7,740,646 B2 | 6/2010 | Hunt et al. |
| 7,741,273 B2 | 6/2010 | McKay et al. |
| 7,744,609 B2 | 6/2010 | Allen et al. |
| 7,758,595 B2 | 7/2010 | Allen et al. |
| 7,766,926 B2 | 8/2010 | Bosley, Jr. et al. |
| 7,766,939 B2 | 8/2010 | Yeung et al. |
| 7,803,574 B2 | 9/2010 | Desai et al. |
| 7,806,908 B2 | 10/2010 | Ruff |
| 7,815,589 B2 | 10/2010 | Meade et al. |
| 7,845,356 B2 | 12/2010 | Paraschac et al. |
| 7,850,894 B2 | 12/2010 | Lindh et al. |
| 7,857,829 B2 | 12/2010 | Kaplan et al. |
| 7,862,583 B2 | 1/2011 | Long |
| 7,871,425 B2 | 1/2011 | Jones et al. |
| 7,875,055 B2 | 1/2011 | Cichocki, Jr. |
| 7,879,072 B2 | 2/2011 | Bonutti et al. |
| 7,901,381 B2 | 3/2011 | Birk et al. |
| 7,913,365 B2 | 3/2011 | Genova et al. |
| 7,919,112 B2 | 4/2011 | Pathak et al. |
| 7,923,075 B2 | 4/2011 | Yeung et al. |
| 7,935,773 B2 | 5/2011 | Hadba et al. |
| 7,950,559 B2 | 5/2011 | Peterson et al. |
| 7,951,065 B2 | 5/2011 | Bosley, Jr. et al. |
| 7,956,100 B2 | 6/2011 | Wang |
| 7,967,841 B2 | 6/2011 | Yuan et al. |
| 7,972,347 B2 | 7/2011 | Garvin et al. |
| 7,976,469 B2 | 7/2011 | Bonde et al. |
| 7,981,140 B2 | 7/2011 | Burkhart |
| 7,996,967 B2 | 8/2011 | Genova et al. |
| 8,011,072 B2 | 9/2011 | Genova et al. |
| 8,015,678 B2 | 9/2011 | Genova et al. |
| 8,016,881 B2 | 9/2011 | Furst |
| 8,020,263 B2 | 9/2011 | Genova et al. |
| 8,028,387 B2 | 10/2011 | Genova et al. |

(56) References Cited

U.S. PATENT DOCUMENTS

| | | |
|---|---|---|
| 8,028,388 B2 | 10/2011 | Genova et al. |
| 8,032,996 B2 | 10/2011 | Trull et al. |
| 8,056,599 B2 | 11/2011 | Maiorino |
| 8,066,736 B2 | 11/2011 | Peterson et al. |
| 8,074,654 B2 | 12/2011 | Paraschac et al. |
| 8,074,857 B2 | 12/2011 | Peterson et al. |
| 8,083,770 B2 | 12/2011 | Leung et al. |
| 8,097,005 B2 | 1/2012 | Cohn et al. |
| 8,100,940 B2 | 1/2012 | Leung et al. |
| 8,100,941 B2 | 1/2012 | Lindh, Sr. et al. |
| 8,118,822 B2 | 2/2012 | Schaller et al. |
| 8,118,834 B1 | 2/2012 | Goraltchouk et al. |
| 8,128,393 B2 | 3/2012 | Rolland et al. |
| 8,151,661 B2 | 4/2012 | Schena et al. |
| 8,158,143 B2 | 4/2012 | Lendlein et al. |
| 8,161,618 B2 | 4/2012 | Maiorino et al. |
| 8,178,028 B2 | 5/2012 | Gandhi |
| 8,202,531 B2 | 6/2012 | McKay |
| 8,216,273 B1 | 7/2012 | Goraltchouk et al. |
| 8,222,564 B2 | 7/2012 | Maiorino et al. |
| 8,225,673 B2 | 7/2012 | D'Agostino |
| 8,226,684 B2 | 7/2012 | Nawrocki et al. |
| 8,236,027 B2 | 8/2012 | Wu |
| 8,246,652 B2 | 8/2012 | Ruff |
| 8,257,393 B2 | 9/2012 | Cichocki, Jr. |
| 8,267,961 B2 | 9/2012 | Popadiuk et al. |
| 8,273,105 B2 | 9/2012 | Cohen et al. |
| 8,287,555 B2 | 10/2012 | Starksen et al. |
| 8,303,625 B2 | 11/2012 | Lendlein et al. |
| 8,308,761 B2 | 11/2012 | Brailovski et al. |
| 8,348,973 B2 | 1/2013 | Stopek et al. |
| 8,353,931 B2 | 1/2013 | Stopek et al. |
| 8,403,017 B2 | 3/2013 | Maiorino et al. |
| 8,403,947 B2 | 3/2013 | Ochial |
| 8,414,612 B2 | 4/2013 | Kirsch et al. |
| 8,454,653 B2 | 6/2013 | Hadba et al. |
| 8,460,338 B2 | 6/2013 | Goraltchouk et al. |
| 8,480,557 B2 | 7/2013 | Guterman |
| 8,500,762 B2 | 8/2013 | Sholev et al. |
| 8,541,027 B2 | 9/2013 | Wright et al. |
| 8,562,644 B2 | 10/2013 | Yuan et al. |
| 8,563,117 B2 | 10/2013 | Messersmith et al. |
| 8,615,856 B1 | 12/2013 | Gelbart |
| 8,628,465 B2 | 1/2014 | Mamo et al. |
| 8,636,767 B2 | 1/2014 | McCalin |
| 8,641,732 B1 | 2/2014 | Goraltchouk et al. |
| 8,652,170 B2 | 2/2014 | Leung et al. |
| 8,652,215 B2 | 2/2014 | Bellamkonda et al. |
| 8,663,277 B2 | 3/2014 | Collier et al. |
| 8,673,536 B2 | 3/2014 | Ledlein et al. |
| 8,679,158 B2 | 3/2014 | Leung et al. |
| 8,690,914 B2 | 4/2014 | Leung et al. |
| 8,707,959 B2 | 4/2014 | Paraschac et al. |
| 8,721,664 B2 | 5/2014 | Ruff et al. |
| 8,721,681 B2 | 5/2014 | Leung et al. |
| 8,734,485 B2 | 5/2014 | Leung et al. |
| 8,734,486 B2 | 5/2014 | Leung et al. |
| 8,793,863 B2 | 5/2014 | Hunter et al. |
| 8,747,436 B2 | 6/2014 | Nawrocki et al. |
| 8,747,437 B2 | 6/2014 | Leung et al. |
| 8,747,438 B2 | 6/2014 | Longo et al. |
| 8,764,776 B2 | 7/2014 | Leung et al. |
| 8,764,796 B2 | 7/2014 | Kaplan et al. |
| 8,771,313 B2 | 7/2014 | Goraltchouk et al. |
| 8,777,987 B2 | 7/2014 | Herrmann et al. |
| 8,777,988 B2 | 7/2014 | Leung et al. |
| 8,777,989 B2 | 7/2014 | Leung et al. |
| 8,821,539 B2 | 9/2014 | Rousseau |
| 8,821,540 B2 | 9/2014 | Leung et al. |
| 8,852,232 B2 | 10/2014 | Leung et al. |
| 8,864,776 B2 | 10/2014 | Bogart et al. |
| 8,870,915 B2 | 10/2014 | Mayer et al. |
| 8,870,916 B2 | 10/2014 | Ewers et al. |
| 8,875,607 B2 | 11/2014 | Kozlowski |
| 8,876,865 B2 | 11/2014 | Goraltchouk et al. |
| 8,888,796 B2 | 11/2014 | Lindh et al. |
| 8,888,810 B2 | 11/2014 | Hadba et al. |
| 8,915,943 B2 | 12/2014 | Hunter |
| 8,916,077 B1 | 12/2014 | Goraltchouk et al. |
| 8,926,659 B2 | 1/2015 | Genova et al. |
| 8,932,327 B2 | 1/2015 | Kosa et al. |
| 8,932,328 B2 | 1/2015 | Megaro et al. |
| 8,944,804 B2 | 2/2015 | Robeson et al. |
| 8,961,560 B2 | 2/2015 | Avelar et al. |
| 9,011,489 B2 | 4/2015 | Ostrovsky et al. |
| 9,044,224 B2 | 6/2015 | Lauria |
| 9,125,647 B2 | 9/2015 | Goraltchouk et al. |
| 9,138,222 B2 | 9/2015 | Bonutti et al. |
| 9,186,135 B2 | 11/2015 | Kim et al. |
| 9,220,499 B2 | 12/2015 | Viola |
| 9,248,580 B2 | 2/2016 | Leung et al. |
| 9,307,983 B2 | 4/2016 | Stopek et al. |
| 9,398,943 B2 | 7/2016 | Criscuolo et al. |
| 9,439,746 B2 | 9/2016 | Bell et al. |
| 9,545,191 B2 | 1/2017 | Stokes et al. |
| 9,675,341 B2 | 6/2017 | D'Agostino et al. |
| 9,718,190 B2 | 8/2017 | Larkin et al. |
| 9,808,234 B2 | 11/2017 | Kim |
| 2002/0022861 A1 | 2/2002 | Jacobs et al. |
| 2002/0029011 A1 | 3/2002 | Dyer |
| 2002/0029066 A1 | 3/2002 | Foerster |
| 2002/0095164 A1 | 7/2002 | Andreas et al. |
| 2002/0099394 A1 | 7/2002 | Houser et al. |
| 2002/0111641 A1 | 8/2002 | Peterson et al. |
| 2002/0111688 A1 | 8/2002 | Cauthen |
| 2002/0151980 A1 | 10/2002 | Cauthen |
| 2002/0161168 A1 | 10/2002 | Shalaby et al. |
| 2002/0165555 A1 | 11/2002 | Stein et al. |
| 2002/0173822 A1 | 11/2002 | Justin et al. |
| 2002/0198544 A1 | 12/2002 | Uflacker |
| 2003/0040795 A1 | 2/2003 | Elson et al. |
| 2003/0069602 A1 | 4/2003 | Jacobs et al. |
| 2003/0088270 A1 | 5/2003 | Lubbers et al. |
| 2003/0149447 A1 | 8/2003 | Morency |
| 2003/0167072 A1 | 9/2003 | Oberlander |
| 2003/0204193 A1 | 10/2003 | Gabriel et al. |
| 2004/0010275 A1 | 1/2004 | Jacobs et al. |
| 2004/0068293 A1 | 4/2004 | Scalzo et al. |
| 2004/0068294 A1 | 4/2004 | Scalzo et al. |
| 2004/0088003 A1 | 5/2004 | Leung et al. |
| 2004/0098051 A1 | 5/2004 | Fallin et al. |
| 2004/0138683 A1 | 7/2004 | Shelton et al. |
| 2004/0153153 A1 | 8/2004 | Elson et al. |
| 2004/0167572 A1 | 8/2004 | Roth et al. |
| 2004/0186487 A1 | 9/2004 | Klein et al. |
| 2004/0193257 A1 | 9/2004 | Wu et al. |
| 2004/0260340 A1 | 12/2004 | Jacobs et al. |
| 2004/0267309 A1 | 12/2004 | Garvin |
| 2005/0004601 A1 | 1/2005 | Kong et al. |
| 2005/0004602 A1 | 1/2005 | Hart et al. |
| 2005/0033324 A1 | 2/2005 | Phan |
| 2005/0049636 A1 | 3/2005 | Leiboff |
| 2005/0055051 A1 | 3/2005 | Grafton |
| 2005/0065533 A1 | 3/2005 | Magen et al. |
| 2005/0066645 A1 | 3/2005 | Dejakum et al. |
| 2005/0096698 A1 | 5/2005 | Lederman |
| 2005/0113936 A1 | 5/2005 | Brustad et al. |
| 2005/0119694 A1 | 6/2005 | Jacobs et al. |
| 2005/0154255 A1 | 7/2005 | Jacobs |
| 2005/0181009 A1 | 8/2005 | Hunter et al. |
| 2005/0186247 A1 | 8/2005 | Hunter et al. |
| 2005/0197699 A1 | 9/2005 | Jacobs et al. |
| 2005/0199249 A1 | 9/2005 | Karram |
| 2005/0203576 A1 | 9/2005 | Sulamanidze et al. |
| 2005/0209542 A1 | 9/2005 | Jacobs et al. |
| 2005/0209612 A1 | 9/2005 | Nakao |
| 2005/0267531 A1 | 12/2005 | Ruff et al. |
| 2006/0020272 A1 | 1/2006 | Gildenberg |
| 2006/0036266 A1 | 2/2006 | Sulamanidze et al. |
| 2006/0058799 A1 | 3/2006 | Elson et al. |
| 2006/0058844 A1 | 3/2006 | White et al. |
| 2006/0079469 A1 | 4/2006 | Anderson et al. |
| 2006/0085016 A1 | 4/2006 | Eremia |
| 2006/0089672 A1 | 4/2006 | Martinek |

(56) References Cited

U.S. PATENT DOCUMENTS

| | | |
|---|---|---|
| 2006/0111742 A1 | 5/2006 | Kaplan et al. |
| 2006/0116503 A1 | 6/2006 | Lendlein et al. |
| 2006/0135994 A1 | 6/2006 | Ruff |
| 2006/0135995 A1 | 6/2006 | Ruff |
| 2006/0142784 A1 | 6/2006 | Kontos |
| 2006/0194721 A1 | 8/2006 | Allen |
| 2006/0200062 A1 | 9/2006 | Saadat |
| 2006/0207612 A1 | 9/2006 | Jackson et al. |
| 2006/0229671 A1 | 10/2006 | Steiner et al. |
| 2006/0235447 A1 | 10/2006 | Walshe |
| 2006/0241658 A1 | 10/2006 | Cerundolo |
| 2006/0253126 A1 | 11/2006 | Bjerken et al. |
| 2006/0258938 A1 | 11/2006 | Hoffman et al. |
| 2006/0272979 A1 | 12/2006 | Lubbers et al. |
| 2006/0276808 A1 | 12/2006 | Arnal et al. |
| 2006/0286289 A1 | 12/2006 | Prajapati et al. |
| 2006/0287675 A1 | 12/2006 | Prajapati et al. |
| 2006/0287676 A1 | 12/2006 | Prajapati et al. |
| 2007/0016251 A1 | 1/2007 | Roby |
| 2007/0027475 A1 | 2/2007 | Pagedas |
| 2007/0088135 A1 | 4/2007 | Lendlein et al. |
| 2007/0088391 A1 | 4/2007 | McAlexander et al. |
| 2007/0134292 A1 | 6/2007 | Suokas et al. |
| 2007/0135840 A1 | 6/2007 | Schmieding |
| 2007/0151961 A1 | 7/2007 | Kleine et al. |
| 2007/0156175 A1 | 7/2007 | Weadock et al. |
| 2007/0185494 A1 | 8/2007 | Reese |
| 2007/0208355 A1 | 9/2007 | Ruff |
| 2007/0213744 A1 | 9/2007 | Farris |
| 2007/0213770 A1 | 9/2007 | Drefyss |
| 2007/0219587 A1 | 9/2007 | Accardo |
| 2007/0224237 A1 | 9/2007 | Hwang et al. |
| 2007/0225642 A1 | 9/2007 | Houser et al. |
| 2007/0225761 A1 | 9/2007 | Shetty |
| 2007/0225763 A1 | 9/2007 | Zwolinski et al. |
| 2007/0225764 A1 | 9/2007 | Benavitz et al. |
| 2007/0239206 A1 | 10/2007 | Shelton, IV et al. |
| 2007/0239207 A1 | 10/2007 | Beramendi |
| 2007/0293892 A1 | 12/2007 | Takasu |
| 2008/0009902 A1 | 1/2008 | Hunter et al. |
| 2008/0046094 A1 | 2/2008 | Han et al. |
| 2008/0066764 A1 | 3/2008 | Paraschac et al. |
| 2008/0077181 A1 | 3/2008 | Jones et al. |
| 2008/0082113 A1 | 4/2008 | Bishop et al. |
| 2008/0082129 A1 | 4/2008 | Jones et al. |
| 2008/0086169 A1 | 4/2008 | Jones et al. |
| 2008/0086170 A1 | 4/2008 | Jones et al. |
| 2008/0132943 A1 | 6/2008 | Maiorino et al. |
| 2008/0195147 A1 | 8/2008 | Stopek |
| 2008/0215072 A1 | 9/2008 | Kelly |
| 2008/0221618 A1 | 9/2008 | Chen et al. |
| 2008/0255611 A1 | 10/2008 | Hunter |
| 2008/0255612 A1 | 10/2008 | Hunter |
| 2008/0262542 A1 | 10/2008 | Sulamanidze et al. |
| 2008/0281338 A1 | 11/2008 | Wohlert et al. |
| 2008/0281357 A1 | 11/2008 | Sung et al. |
| 2009/0018577 A1 | 1/2009 | Leung et al. |
| 2009/0082856 A1 | 3/2009 | Flanagan |
| 2009/0099597 A1 | 4/2009 | Isse |
| 2009/0105753 A1 | 4/2009 | Greenhalgh et al. |
| 2009/0112236 A1 | 4/2009 | Stopek |
| 2009/0112259 A1 | 4/2009 | D'Agostino |
| 2009/0143819 A1 | 6/2009 | D'Agostino |
| 2009/0210006 A1 | 8/2009 | Cohen et al. |
| 2009/0226500 A1 | 9/2009 | Avelar et al. |
| 2009/0228021 A1 | 9/2009 | Leung |
| 2009/0248066 A1 | 10/2009 | Wilkie |
| 2009/0248070 A1* | 10/2009 | Kosa ............ A61B 17/06166 606/232 |
| 2009/0259251 A1 | 10/2009 | Cohen |
| 2009/0299408 A1 | 12/2009 | Schuldt-Hempe et al. |
| 2010/0023055 A1 | 1/2010 | Rousseau |
| 2010/0057123 A1 | 3/2010 | D'Agostino et al. |
| 2010/0063540 A1 | 3/2010 | Maiorino |
| 2010/0163056 A1 | 7/2010 | Tschopp et al. |
| 2010/0211097 A1 | 8/2010 | Hadba et al. |
| 2010/0230300 A1 | 9/2010 | Hunter et al. |
| 2010/0239635 A1 | 9/2010 | McClain et al. |
| 2010/0298637 A1 | 11/2010 | Ruff |
| 2010/0298867 A1 | 11/2010 | Ruff |
| 2010/0298868 A1 | 11/2010 | Ruff |
| 2010/0298871 A1 | 11/2010 | Ruff et al. |
| 2010/0313729 A1 | 12/2010 | Genova et al. |
| 2010/0318123 A1 | 12/2010 | Leung et al. |
| 2011/0022086 A1 | 1/2011 | D'Agostino et al. |
| 2011/0125188 A1 | 5/2011 | Goraltchouk et al. |
| 2011/0264138 A1 | 10/2011 | Avelar et al. |
| 2011/0282384 A1* | 11/2011 | Odermatt ......... A61B 17/06166 606/222 |
| 2012/0245659 A1 | 9/2012 | Matthews |
| 2013/0172931 A1 | 7/2013 | Gross et al. |
| 2013/0204295 A1 | 8/2013 | Hunter et al. |
| 2013/0226234 A1 | 8/2013 | Avelar et al. |
| 2013/0238021 A1 | 9/2013 | Gross et al. |
| 2013/0238022 A1 | 9/2013 | Gross et al. |
| 2013/0317545 A1 | 11/2013 | Gross et al. |
| 2014/0039527 A1 | 2/2014 | Avelar et al. |

FOREIGN PATENT DOCUMENTS

| | | |
|---|---|---|
| CN | 2640420 | 9/2004 |
| CN | 1611189 | 5/2005 |
| CN | 101208037 | 6/2008 |
| CN | 101208045 | 6/2008 |
| CN | 101495025 | 7/2009 |
| CN | 101626735 | 1/2010 |
| CN | 101653355 | 2/2010 |
| CN | 101677767 | 3/2010 |
| CN | 101686820 | 3/2010 |
| CN | 101686873 | 3/2010 |
| CN | 101690672 | 4/2010 |
| DE | 1810800 | 6/1970 |
| DE | 3227984 | 2/1984 |
| DE | 4302895 | 8/1994 |
| DE | 19618891 | 4/1997 |
| DE | 19833703 | 2/2000 |
| DE | 10245025 | 4/2004 |
| DE | 102005004317 | 6/2006 |
| EP | 0121362 | 9/1987 |
| EP | 0329787 | 8/1989 |
| EP | 0428253 | 5/1991 |
| EP | 0464479 | 1/1992 |
| EP | 0464480 | 1/1992 |
| EP | 0513713 | 5/1992 |
| EP | 0513736 | 11/1992 |
| EP | 0558993 | 9/1993 |
| EP | 0574707 | 12/1993 |
| EP | 0576337 A1 | 12/1993 |
| EP | 0612504 | 8/1994 |
| EP | 0632999 | 1/1995 |
| EP | 0664198 | 7/1995 |
| EP | 0673624 | 9/1995 |
| EP | 0705567 | 4/1996 |
| EP | 0755656 | 1/1997 |
| EP | 0576337 B1 | 3/1997 |
| EP | 0826337 | 3/1998 |
| EP | 0839499 | 5/1998 |
| EP | 0913123 | 5/1999 |
| EP | 0916310 | 5/1999 |
| EP | 0960600 | 12/1999 |
| EP | 1075843 B1 | 2/2005 |
| EP | 1525851 | 4/2005 |
| EP | 1532942 | 5/2005 |
| EP | 1800609 | 6/2007 |
| EP | 0991359 B1 | 11/2007 |
| EP | 1852071 | 11/2007 |
| EP | 1656890 | 12/2008 |
| EP | 2036502 A2 | 3/2009 |
| EP | 1948261 B1 | 11/2010 |
| EP | 2245992 | 11/2010 |
| EP | 1726317 B1 | 7/2012 |
| EP | 1585434 | 1/2015 |
| FR | 2619129 | 2/1989 |
| FR | 2693108 | 1/1994 |

(56) References Cited

FOREIGN PATENT DOCUMENTS

| | | |
|---|---|---|
| GB | 267007 | 3/1927 |
| GB | 1091282 | 11/1967 |
| GB | 1428560 | 3/1976 |
| GB | 1506362 | 4/1978 |
| GB | 1508627 | 4/1978 |
| GB | 2409211 | 6/2005 |
| JP | S54-116419 | 9/1979 |
| JP | S63-288146 | 11/1988 |
| JP | S64-013034 | 1/1989 |
| JP | H01-113091 | 5/1989 |
| JP | H03-80868 | 4/1991 |
| JP | H03-165751 | 7/1991 |
| JP | H04-96758 | 3/1992 |
| JP | H04-266749 | 9/1992 |
| JP | H09-103477 | 4/1997 |
| JP | H10-85225 | 4/1998 |
| JP | H11-313826 | 11/1999 |
| JP | H11-332828 | 12/1999 |
| JP | 2002-059235 | 2/2002 |
| JP | 2003-275217 | 9/2003 |
| JP | 2007-502281 | 2/2007 |
| JP | 2009-118967 | 6/2009 |
| KR | 2005-0072908 | 7/2005 |
| KR | 2006-0013299 | 2/2006 |
| NZ | 501224 | 3/2002 |
| NZ | 531262 | 12/2005 |
| RU | 2139690 | 10/1999 |
| RU | 2175855 | 11/2001 |
| RU | 2241389 | 12/2004 |
| RU | 2268752 C2 | 1/2006 |
| SU | 560599 | 6/1977 |
| SU | 1745214 | 7/1992 |
| SU | 1752358 | 8/1992 |
| WO | WO 96/06565 | 3/1966 |
| WO | WO 86/00020 | 1/1986 |
| WO | WO 87/01270 | 3/1987 |
| WO | WO 88/09157 | 12/1988 |
| WO | WO 89/05618 | 6/1989 |
| WO | WO 90/09149 | 8/1990 |
| WO | WO 90/14795 | 12/1990 |
| WO | WO 92/22336 | 12/1992 |
| WO | WO 95/16399 | 6/1995 |
| WO | WO 95/29637 | 11/1995 |
| WO | WO 97/00047 | 1/1997 |
| WO | WO 98/52473 | 11/1998 |
| WO | WO 98/55031 | 12/1998 |
| WO | WO 99/21488 | 5/1999 |
| WO | WO 99/33401 | 7/1999 |
| WO | WO 99/52478 | 10/1999 |
| WO | WO 99/59477 | 11/1999 |
| WO | WO 99/62431 | 12/1999 |
| WO | WO 00/51658 | 9/2000 |
| WO | WO 00/51685 | 9/2000 |
| WO | WO 01/06952 | 2/2001 |
| WO | WO 01/56626 | 8/2001 |
| WO | WO 2003/001979 | 1/2003 |
| WO | WO 2003/003925 | 1/2003 |
| WO | WO 2003/045255 | 6/2003 |
| WO | WO 2003/077772 | 9/2003 |
| WO | WO 2003/092758 | 11/2003 |
| WO | WO 2003/103733 | 12/2003 |
| WO | WO 2003/103972 | 12/2003 |
| WO | WO 2003/105703 | 12/2003 |
| WO | WO 2004/014236 | 2/2004 |
| WO | WO 2004/030517 | 4/2004 |
| WO | WO 2004/030520 | 4/2004 |
| WO | WO 2004/030704 | 4/2004 |
| WO | WO 2004/030705 | 4/2004 |
| WO | WO 2004/062459 | 7/2004 |
| WO | WO 2004/100801 | 11/2004 |
| WO | WO 2004/112853 | 12/2004 |
| WO | WO 2005/016176 | 2/2005 |
| WO | WO 2005/074913 | 8/2005 |
| WO | WO 2005/096955 | 10/2005 |
| WO | WO 2005/096956 | 10/2005 |
| WO | WO 2005/112787 | 12/2005 |
| WO | WO 2006/005144 | 1/2006 |
| WO | WO 2006/012128 | 2/2006 |
| WO | WO 2006/037399 | 4/2006 |
| WO | WO 2006/061868 | 6/2006 |
| WO | WO 2006/079469 | 8/2006 |
| WO | WO 2006/082060 | 8/2006 |
| WO | WO 2006/099703 | 9/2006 |
| WO | WO 2006/138300 | 12/2006 |
| WO | WO 2007/005291 | 1/2007 |
| WO | WO 2007/005905 | 1/2007 |
| WO | WO 2007/038837 | 4/2007 |
| WO | WO 2007/053812 | 5/2007 |
| WO | WO 2007/089864 | 8/2007 |
| WO | WO 2007/112024 | 10/2007 |
| WO | WO 2007/133103 | 11/2007 |
| WO | WO 2007/145614 | 12/2007 |
| WO | WO 2008/107979 | 9/2008 |
| WO | WO 2008/128113 | 10/2008 |
| WO | WO 2008/150773 | 12/2008 |
| WO | WO 2009/042841 | 4/2009 |
| WO | WO 2009/068252 | 6/2009 |
| WO | WO 2009/087105 | 7/2009 |
| WO | WO 2009/097408 | 8/2009 |
| WO | WO 2009/097556 | 8/2009 |
| WO | WO 2009/105663 | 8/2009 |
| WO | WO 2009/151876 | 12/2009 |
| WO | WO 2010/008815 | 1/2010 |
| WO | WO 2010/052007 | 5/2010 |
| WO | WO 2011/025760 | 3/2011 |
| WO | WO 2011/053375 | 5/2011 |
| WO | WO 2011/090628 | 7/2011 |
| WO | WO 2011/139916 | 11/2011 |
| WO | WO 2011/140283 | 11/2011 |
| WO | WO 2015/069042 | 5/2015 |

OTHER PUBLICATIONS

Bacci, Pier Antonio, "Chirurgia Estetica Mini Invasiva Con Fili Di Sostegno", Collana di Arti, Pensiero e Scienza; Minelli Editore—2006; 54 pgs.

Behl, Marc et al., "Shape-Memory Polymers", Materials Today Apr. 2007; 10(4); 20-28.

Belkas, J. S. et al., "Peripheral nerve regeneration through a synthetic hydrogel nerve tube", Restorative Neurology and Neuroscience 23 (2005) 19-29.

Bellin, I. et al., "Polymeric triple-shape materials", Proceedings of the National Academy of Sciences of the United States of America Nov. 28, 2006; 2103(48):18043-18047.

Boenisch, U.W. et al. 'Pull-Out strength and stiffness of meniscal repair using absorbable arrows or Ti-Cron vertical and horizontal loop sutures' American Journal of Sports Medicine, Sep.-Oct. 1999 vol. 27, Issue 5, pp. 626-631.

Buckley, P.R. 'Actuation of Shape Memory Polymer using Magnetic Fields for Applications in Medical Devices' Master of Science in Mechanical Engineering in Massachusetts Institute of Technology Jun. 2003, 144 pages.

Buncke, Jr., H.J. et al. 'The Suture Repair of One-Millimeter Vessels, microvascular surgery' (1966) Report of First Conference; Oct. 6-7 pp. 24-35.

Bunnell, S. 'Gig pull-out suture for tendons' J Bone Joint Surg. Am (1954) vol. 36A, No. 4 pp. 850-851.

CCPR Centro De Cirurgia Plastica e Reabilitacao Up Lifting (Aptos Threads) http://ccpr.com.br/upl-l.htm, Aug. 19, 2002 pp. 1-2.

Croce, E. et al 'Intracorporeal Knot-Tying and Suturing Techniques in Laparoscopic Surgery: Technical Details' Journal of the Society of Laparoendoscopic Surgeons (2000) vol. 4 pp. 17-22.

Dahlin, Lars, "Techniques of Peripheral Nerve Repair", Scandinavian Journal of Surgery 97: 310-316, 2008.

Datillo, Jr., P.P. 'Knotless Bi-directional Barbed Absorbable Surgical Suture' Dissertation submitted to the Graduate Faculty of North Carolina State University Textile Management and Technology Nov. 2002, 75 pages.

Datillo, Jr. P.P et al. 'Medical Textiles: Application of an Absorbable Barbed Bi-Directional Surgical Suture' (2002) The Journal of Textile and Apparel Technology and Management vol. 2, Issue 2, pp. 1-5.

(56) References Cited

OTHER PUBLICATIONS

Datillo, Jr., P. et al. 'Tissue holding performance of knotless absorbable sutures' Society for Biomaterials 29th Annual Meeting Transactions (2003) p. 101.
Declaration of Dr. Gregory L. Ruff, dated Aug. 19, 2005, 8 pages, with Exhibits A-E.
De Persia, Raul et al., "Mechanics of Biomaterials: Sutures After the Surgery", Applications of Engineering Mechanics in Medicine, GED-University of Puerto Rico, Mayaguez May 2005, p. F1-F27.
Delorenzi, C.L., "Barbed Sutures: Rationale and Technique", Aesthetic Surg. J. Mar. 26, 2006(2): 223-229.
Demyttenaere, Sebastian V. et al., "Barbed Suture for Gastrointestinal Closure: A Randomized Control Trial", Surgical Innovation; vol. 16, No. 3; Sep. 2009; pp. 237-242.
Einarsson, Jon I. et al., "Barbed Suture, now in the toolbox of minimally invasive gyn surgery", OBG Management; vol. 21, No. 9; Sep. 2009; pp. 39-41.
Gross, Alex, "Physician perspective on thread lifts", Dermatology Times Feb. 27, 2006(2): 2 pages.
Gross, R.A. et al. 'Biodegradable Polymers for the Environment' Science (2002) vol. 297, Issue 5582 p. 803.
Han, H. et al. 'Mating and Piercing Micromechanical Suture for Surface Bonding Applications' (1991) Proceedings of the 1991 Micro Electro Mechanical Systems (NIEMS>91), An Investigation of Micro Structures, Sensors, Actuators, Machines and Robots pp. 253-258.
http://www.merriam-webster.com/dictionary/remove, Apr. 14, 2016.
Ingle, N.P. et al. 'Barbed Suture Anchoring Strength: Applicability to Dissimilar Polymeric Materials' College of Textiles, North Carolina State University, 7th World Biomaterials Congress 2004, 1 page.
Ingle, N.P. et al. 'Mechanical Performance and Finite Element Analysis of Bi-directional Barbed Sutures' Master of Science in Textile Technology & Management at North Carolina State University Aug. 2003, 126 pages.
Ingle, N.P. et al., "Optimizing the tissue anchoring performance of barbed sutures in skin and tendon tissues", Journal of Biomechanics 43 (2010); pp. 302-309.
Ingle, Nilesh P et al., "Testing the Tissue-holding Capacity of Barbed Sutures", College of Textiles, North Carolina State University, Fiber Science, The Next Generation Oct. 17-19, 2005, New Jersey Institute of Technology, Newark, NJ, 4 pages.
Jennings et al. 'A New Technique in primary tendon repair' Surg. Gynecol. Obstet. (1952) vol. 95, No. 5 pp. 597-600.
Jeong, H.E. et al. 'A nontransferring dry adhesive with hierarchical polymer nanohairs' PNAS 106 (14) pp. 5639-5644 (2009).
Kaminer, M. et al., "ContourLift™: A New Method of Minimally Invasive Facial Rejuvenation", Cosmetic Dermatology Jan. 2007; 20(1): 29-35.
Kelch et al., "Shape-memory Polymer Networks from Olio [(ϵ-hydroxycaproate)-co-glycolate] dimethacrylates and Butyl Acrylate with Adjustable Hydrolytic Degradation Rate", Biomacromolecules 2007;8(3):10181027.
Khademhosseini, Ali et al., "Nanobiotechnology Drug Delivery and Tissue Engineering", Chemical Engineering Progress 102:38-42 (2006).
Kuniholm J.F. et al. 'Automated Knot Tying for Fixation in Minimally Invasive, Robot Assisted Cardiac Surgery' Master of Science in Mechanical & Aerospace Engineering at North Carolina State University May 2003, 71 pages.
Lendlein, A. et al. 'Biodegradable, Elastic Shape-Memory Polymers for Potential Biomedical Applications' (2002) Science vol. 296 pp. 1673-1676.
Lendlein, A. et al. 'Shape-Memory Polymers' Agnew Chem. Int. Ed. (2002) vol. 41 pp. 2034-2057.
Leung, J. et al. 'Barbed, Bi-directional Medical Sutures: Biomechanical Properties and Wound Closure Efficacy Study' 2002 Society for Biomaterials 28th Annual Meeting Transactions 1 page.
Leung, J. et al. 'Barbed, Bi-directional Surgical Sutures' International Conference & Exhibition on Healthcare & Medical Textiles, Jul. 8-9, 2003 pp. 1-8.
Leung, J. et al. 'Barbed, Bi-directional Surgical Sutures: In Vivo Strength and Histopathology Evaluations' 2003 Society for Biomaterials 29th Annual Meeting Transactions pp. 100.
Leung, J. et al., "Barbed Suture Technology: Recent Advances", Medical Textiles 2004, Advances in Biomedical Textiles and Healthcare Products, Conference Proceedings, IFAI Expo 2004, Oct. 26-27, 2004, Pittsburgh, PA., pp. 62-80.
Leung, J. et al. 'Performance Enhancement of a Knotless Suture via Barb Geometry Modifications' 7th World Biomaterials Congress 2004, 1 page.
Li, Y.Y. et al. 'Polymer Replicas of Photonic Porous Silicon for Sensing and Drug Delivery Applications' (2003) Science vol. 299 pp. 2045-2047.
Liu, Changdeng et al., "Shape Memory Polymer with Improved Shape Recovery", Mater. Res. Soc. Symp. Proc. vol. 855E, 2005 Materials Research Society, pp. W4.7.1-W4.7.6.
Madduri, Srinivas et al., "Neurotrophic factors release from nerve conduits for peripheral axonal regeneration", European Cells and Materials vol. 16; Suppl. 1 (2008), p. 14.
Madhave et al. 'A biodegradable and biocompatible gecko-inspired tissue adhesive' PNAS 105(7) pp. 2307-2312 (2008).
Maitland et al., "Prototype laser-activated shape memory polymer foam device for embolic treatment of aneurysms", Journal of Biomedical Optics May/Jun. 2007;12(3): pp. 030504-1 to 030504-3.
Malina, M. et al. 'Endovascular AAA Exclusion: Will Stents with Hooks and Barbs Prevent Stent-Graft Migration' Journal Endovascular Surgery (1998) vol. 5 pp. 310-317.
Mansberger et al. 'A New Type Pull-Out Wire for Tendon Surgery: A Preliminary Report' Department of Surgery, University Hospital and University of Maryland School of Medicine, Baltimore, Maryland, Received for Publication May 10, 1951 pp. 119-121.
Martin, D.P. et al. 'Medical applications of poly-4-hydroxybutyrate: a strong flexible absorbable biomaterial' Biochemical Engineering Journal vol. 16 (2003) pp. 97-105.
Mason, M.L. 'Primary and Secondary Tendon Suture. A discussion of the significance of technique in tendon surgery' (1940) Surg Gynecol Obstet 70.
McKee, GK 'Metal anastomosis tubes in tendon suture' The Lancet (1945) pp. 659-660.
McKenzie 'An Experimental Multiple Barbed Suture for the Long Flexor Tendons of the Palm and Fingers' The Journal of Bone and Joint Surgery (1967) vol. 49B, No. 3 pp. 440-447.
Middleton and Tipton 'Synthetic Biodegradable Polymers as Medical Devices' (1998) Medical Plastics and 13iomaterial s Magazine, 9 pages.
Moran et al., "Bidirectional-Barbed Sutured Knotless Running Anastomosis v Classic van Velthovan in a Model System", Journal of Endourology Oct. 2007; 21(10); 1175-1177.
Mullner, "Metal Foam Has a Good Memory", Dec. 18, 2007 Original story at http://www.physorg.com/news117214996.html.
Murtha et al., "Evaluation of a Novel Technique for Wound Closure Using A Barbed Suture", Journal of the American Society of Plastic Surgeons 2006; 117(6); 1769-1780.
Nie, Zhihong and Kumacheva, Eugenia, "Patterning surfaces with functional polymers", Nature Materials vol. 7(2008): 277-290.
Paul, Malcolm D., "Bidirectional Barbed Sutures for Wound Closure: Evolution and Applications", Journal of the American College of Certified Wound Specialists (2009) 1, 51-57.
Paul, Malcolm D. and Rui Avelar, "Quill™ SRS Techniques & Procedures A Novel Approach to Soft Tissue Approximation", Canada, Angiotech Pharmaceuticals, Inc., First Edition Aug. 2007: 20 pages.
Paul, Malcolm D. and Rui Avelar, "Quill™ SRS Techniques & Procedures A Novel Approach to Soft Tissue Approximation", Canada, Angiotech Pharmaceuticals, Inc., Second Edition Aug. 2008: 20 pages.

(56) References Cited

OTHER PUBLICATIONS

Paul, Malcolm D. and Rui Avelar, "Quill™ SRS Techniques & Procedures A Novel Approach to Soft Tissue Approximation", Canada, Angiotech Pharmaceuticals, Inc., Third Edition 2009, 8 2007-2009: 27 pages.
Paul, Malcolm D. and Rui Avelar, "Quill™ SRS Techniques & Procedures A Novel Approach to Soft Tissue Approximation", Canada, Angiotech Pharmaceuticals, Inc., Fourth Edition 2010, 8 2007-2010: 27 pages.
Paul, Malcolm D., "Using Barbed Sutures in Open/Subperiosteal Midface Lifting", Aesthetic Surgery Journal 2006(26): 725-732.
Potenza, A. 'Tendon Healing Within the Flexor Digital Sheath in the Dog: An Experimental Study' Journal of Bone & Joint Surgery (1962) vol. 44A No. 1 pp. 49-64.
Pulvertaft 'Suture Materials and Tendon Junctures' American Journal of Surgery (1965) vol. 109 pp. 346-352.
Quill Medical, Inc. 'Barbed Sutures, wrinkle filters give patients more innovative, non-surgical options' Press Release of Program presented at American Society of Plastic Surgeons annual scientific meeting; Philadelphia, Oct. 9, 2004 3 pages.
Quill Medical, Inc. 'Quill Medical's Novel-Self-Anchoring Surgical Suture Approved for Sale in Europe' Press Release; Research Triangle Park, N.C. May 10, 2004, 1 page.
Quill Medical, Inc., "Quill Medical, Inc. Receives FDA Clearance for First-in-Class Knot-Less Self-Anchoring Surgical Suture", Press Release; Research Triangle Park, N.C., Nov. 4, 2004, 1 page.
Richert, Ludovic et al., "Surface Nanopatterning to Control Cell Growth", Advanced Materials 2008(15): 1-5.
Rodeheaver, G.T. et al., "Barbed Sutures for Wound Closure: In Vivo Wound Security, Tissue Compatibility and Cosmesis Measurements", Society for I3iomaterials 30th Annual Meeting Transactions, 2005, 2 pages.
Rofin-Baasel 'Laser Marking on Plastic Materials' (2001) RB50.0, Rofin-Baasel Inc. 2 pages.
Ruff, Gregory, "Technique and Uses for Absorbable Barbed Sutures", Aesthetic Surgery Journal Sep./Oct. 2006; 26:620-628.
Scherman, Peter et al., "Sutures as longitudinal guides for the repair of nerve defects—Influence of suture numbers and reconstruction of nerve bifurcations", Restorative Neurology and Neuroscience 23 (2005) 79-85.
Schmid A. et al. 'The outspreading anchor cord. A material for arthroscopic suturing of a fresh anterior cruciate ligament rupture' Surgical Clinic of the University of Gottingen (1987) pp. 417-426.
Semenov, G.M. et al. 'Surgical Suture' (2001) Piter, Saint Petersburg, pp. 12-13 and 92-98.
Serafetinides, AA 'Short pulse laser beam interactions with polymers biocompatible materials and tissue' Proce SPIE vol. 3052 (1996) pp. 111-123.
Sulamanidze, M. et al., "APTOS Suture Lifting Methods: 10 Years of Experience", Cl in Plastic Surg 36 (2009); pp. 281-306.
Sulamanidze, M.A. et al. 'Clinical aspects of bloodless facelift using APTOS filaments' A.V. Vishncvsky Institute of Surgery, Bol'shaya Scrpukhovskaya ul, 7, 113811, Moscow, Russia (2002) pp. 24-34.
Sulamanidze, M.A. et al. 'Facial lifting with Aptos threads' International Journal of Cosmetic Surgery and Aesthetic Dermatology (2001) No. 4 pp. 1-8.
Sulamanidze, M.A. et al. 'Management of Facial Rhytids by Subcutaneous Soft Tissue Dissection' (2000) International Journal of Cosmetic Surgery and Aesthetic Dermatology vol. 2 No. 4 pp. 255-259.
Sulamanidze, M.A. et al. 'Morphological foundations of facelift using APTOS filaments' Bolshaya Serpukhovskaya ul 27, 113811 Moscow, Russia (2002) pp. 19-26.
Sulamanidze, M.A. et al. 'Removal of Facial Soft Tissue Ptosis with Special Threads' Dermatol Surg (2002) vol. 28 pp. 367-371.
Sulamanidze, MD, M.A. et al., "Soft tissue lifting in the mid-face: old philosophy, new approach-internal stitching technique (Aptos Needle)", Plastic and Aesthetic Surgery Clinic Total Sharm, Moscow, Russia, (2005): 15-29.
Sulzle, Inc. B.G et al. Drilled End Surgical Needles Jul. 2002 Syracuse, New York.
Surgical Specialties Corporation, "Wound Closure Catalog"; Summer 2005, 5 pages.
Szarmach, R. et al. 'An Expanded Surgical Suture and Needle Evaluation and Selection Program by a Healthcare Resource Management Group Purchasing Organization' Journal of Long-Term Effects of Medical Implants (2003) vol. 13 No. 3 pp. 155-170.
Verdan, C. 'Primary Repair of Flexor Tendons' Journal of Bone and Joint Surgery (1960) vol. 42, No. 4 pp. 647-657.
Villa, Mark T. et al., "Barbed Sutures: A Review of Literature", Plastic and Reconstructive Surgery; Mar. 2008; vol. 121, No. 3; pp. 102e-108e.
Wu. W. 'Barbed Sutures in Facial Rejuvenation' Aesthetic Surgery Journal (2004) vol. 24 pp. 582-587.
Zoltan, J. 'Cicatrix Optimia: Techniques for Ideal Wound Healing' English language edition University Park Press Baltimore (1977) Chapter 3 pp. 54-55.
Australian Office Action, Patent Examination Report No. 1, dated Dec. 19, 2013 for Application No. AU 2011248116, 2 pgs.
Australian Office Action, Patent Examination Report No. 1, dated Jan. 29, 2014 for Application No. AU 2011248117, 3 pgs.
Australian Office Action, Patent Examination Report No. 2, dated Sep. 18, 2014 for Application No. AU 2011248117, 3 pgs.
Canadian Office Action dated Mar. 28, 2017 for Application No. CA 2,798,373, 3 pgs.
Canadian Office Action dated Apr. 4, 2017 for Application No. CA 2,798,361, 3 pgs.
Chinese Office Action, Second, dated Jun. 11, 2015 for Application No. CN 201180033164.9, 3 pgs.
Chinese Search Report dated May 29, 2015 for Application No. CN 201180033164.9, 2 pgs.
Chinese Search Report dated Jun. 3, 2016 for Application No. CN 201510092908.4, 4 pgs.
Chinese Search Report dated Mar. 27, 2017 for Application No. CN 201510525008.4, 2 pgs.
Chinese Office Action, The First Office Action, and Search Report, dated Sep. 2, 2014 for Application No. CN 201180033132.9, 8 pgs.
Chinese Office Action, The Second Office Action dated Apr. 20, 2015 for Application No. CN 201180033132.9, 6 pgs.
Chinese Office Action, The First Office Action, dated Oct. 29, 2014 for Application No. CN 201180033164.9, 5 pgs.
Chinese Office Action, The Third Office Action, dated Nov. 12, 2015 for Application No. CN 201180033164.9, 8 pgs.
Chinese Office Action, First Office Action, dated Jun. 20, 2016 for Application No. CN 201510092908.4, 5 pgs.
Chinese Office Action, First Office Action, dated Apr. 6, 2017 for Application No. CN 201510525008.4, 6 pgs.
Chinese Office Action, The Second Office Action, and Supplementary Search Report, dated Feb. 23, 2018 for Application No. CN 201510525008.4, 7 pgs.
Chinese Search Report, Supplementary, dated Aug. 22, 2018 for Application No. CN 201510525008.4, 1 pg.
Communication from EPO re: EP10000486 dated Apr. 4, 2011, 4 pages.
European Search Report re: EP05025816 dated Jun. 23, 2006.
European Search Report for EP07006258.3 dated May 4, 2007, 4 pages.
European Search Report for EP07015906 dated Oct. 2, 2007.
European Search Report for EP07015905.8 dated Oct. 2, 2007, 2 pages.
European Search Report for EP07016222 dated Jan. 7, 2008.
European Search Report for EP09014651 dated Jan. 12, 2010.
European Search Report for EP10000629.5 dated Mar. 10, 2010, 4 pages.
European Search Report re: EP10000486 dated Apr. 23, 2010.
European Search Report re: EP10004453 dated Jun. 15, 2010.
European Search Report for EP10011871.0 dated Dec. 3, 2010, 2 pages.
European Search Report for EP10011868.6 dated Dec. 6, 2010, 2 pages.
European Search Report for EP10011869 dated Jan. 20, 2011.
European Search Report for EP10011872 dated Apr. 20, 2011.

(56) References Cited

OTHER PUBLICATIONS

European Search Report for EP10012437 dated Apr. 28, 2011.
European Search Report for EP10186592.1 dated Jan. 19, 2011, 2 pages.
European Search Report for EP10184766 dated Apr. 20, 2011
Partial European Search Report re: EP05025816 dated Mar. 20, 2006
Extended European Search Report re: EP07015905.8 dated Oct. 23, 2007
Extended European Search Report re: EP07016222.7 dated Jan. 30, 2008.
Extended European Search Report re: 11778310.0 dated Apr. 21, 2015.
European Search Report, Extended, and Written Opinion dated Aug. 28, 2015 for Application No. EP 11778310.0, 9 pgs.
Supplementary European Search Report re: EP98923664 dated Jun. 12, 2001.
Supplementary European Search Report re: EP03752630 dated Nov. 17, 2005.
Supplementary European Search Report re: EP03770556 dated Nov. 17, 2005.
Supplementary European Search Report re: EP03754965 dated Nov. 18, 2005.
Supplementary European Search Report re: EP03785177 dated May 19, 2009.
Supplementary European Search Report re: EP07017663 dated Nov. 7, 2007.
Supplementary European Search Report re: 11778311 dated Apr. 30, 2015.
European Search Report, Supplementary, and Written Opinion dated Apr. 30, 2015 for Application No. EP 11778311.8, 7 pgs.
European Exam Report dated Oct. 28, 2016 for Application No. EP 11778311.8, 5 pgs.
European Search Report and Written Opinion dated Sep. 24, 2018 for Application No. EP 18178256.6, 10 pgs.
European Search Report, Supplementary Partial, dated May 6, 2015 for Application No. EP 11778310.0, 5 pgs.
European Decision to Grant a European Patent dated May 25, 2018 for Application No. EP 11778310.0, 2 pgs.
European Decision to grant a European Patent dated Aug. 23, 2018 for Application No. EP 11778311.8, 2 pgs.
Indian Office Action dated Aug. 24, 2018 for Application No. 10090/DELNP/2012, 6 pg.
Indian Office Action dated Dec. 14, 2018 for Application No. 10179/DELNP/2012, 10 pgs.
International Search Report for PCT/US1994/09631 dated Dec. 9, 1994.
International Search Report for PCT/US1998/10478 dated Sep. 23, 1998.
International Search Report for PCT/US2002/027525 dated Dec. 9, 2002, 3 pgs.
International Search Report for PCT/US2003/030664 dated May 25, 2004.
International Search Report for PCT/US2003/030666 dated Dec. 15, 2004.
International Search Report for PCT/US2003/025088 dated Dec. 29, 2003.
International Search Report for: PCT/US2003/030674 dated Sep. 2, 2004.
International Search Report for: PCT/US2004/014962 dated Feb. 24, 2005.
International Search Report for PCT/US2007/002688 dated Oct. 22, 2007.
International Search Report for PCT/US2007/074658 dated Jun. 12, 2007, 3 pgs.
International Search Report for PCT/US2008/060127 dated Sep. 23, 2008, 5 pgs.
International Search Report for PCT/US2008/077813 dated Mar. 31, 2009.
International Search Report for PCT/US2008/082009 dated Feb. 16, 2010.
International Search Report for PCT/US2009/032693 dated Aug. 26, 2009.
International Search Report for PCT/US2009/034703 dated Sep. 28, 2009.
International Search Report for PCT/US2009/040545 dated Oct. 29, 2009.
International Search Report for PCT/US2009/041685 dated Dec. 22, 2009.
International Search Report for PCT/US2010/056898 dated Aug. 2, 2011.
International Search Report for PCT/US2010/060889 dated Oct. 11, 2011.
International Search Report for PCT/US2011/034660 dated Feb. 8, 2012.
International Search Report for PCT/US2011/035270 dated Jan. 12, 2012.
International Search Report for PCT/US2011/035271 dated Jan. 12, 2012.
International Search Report for: PCT/US2011/035431 dated Jan. 12, 2012.
International Search Report for PCT/US2011/059238 dated May 21, 2012.
International Preliminary Report re: PCT/US1998/010478 dated Dec. 11, 1999.
International Preliminary Report re: PCT/US2007/002688 dated Aug. 14, 2008.
International Preliminary Report re: PCT/US2008/060127 dated Oct. 13, 2009.
International Preliminary Report re: PCT/US2008/064921 dated Dec. 1, 2009.
International Preliminary Report re: PCT/US2008/075849 dated Mar. 16, 2010.
International Preliminary Report re: PCT/US2008/087788 dated Jun. 22, 2010.
International Preliminary Report re: PCT/US2009/032693 dated Aug. 3, 2010.
International Preliminary Report re: PCT/US2009/034703 dated Aug. 24, 2010.
International Preliminary Report re: PCT/US2009/040545 dated Oct. 19, 2010.
International Preliminary Report re: PCT/US2009/041685 dated Oct. 26, 2010.
International Preliminary Report re: PCT/US2011/035431 dated Nov. 6, 2012.
International Preliminary Report re: PCT/US2011/040014 dated Dec. 14, 2012.
International Preliminary Report re: PCT/US2011/059238 dated May 7, 2013.
Japanese Office Action, Notification of Reasons for Refusal, dated Nov. 18, 2014 for Application No. JP 2013-509246, 5 pgs.
Japanese Office Action, Notification of Reasons for Refusal, dated Apr. 7, 2015 for Application No. JP 2013-509247, 3 pgs.
Japanese Office Action, Notification of Reasons for Refusal, Final, dated Jan. 5, 2016 for Application No. JP 2013-509247, 4 pgs.
Japanese Office Action, Notification of Reasons for Refusal, dated Feb. 2, 2016 for Application No. JP 2015-023956, 4 pgs.
Japanese Office Action, Notification of Reasons for Refusal, dated Sep. 27, 2016 for Application No. JP 2015-023956, 3 pgs.
Japanese Search Report dated Nov. 21, 2014 for Application No. JP 2013-509246, 11 pgs.
Japanese Office Action, Decision of Refusal, dated May 12, 2015 for Application No. JP 2013-509246, 1 pg.
Japanese Office Action, Decision of Refusal, dated Jul. 5, 2016 for Application No. JP 2013-509247, 1 pg.
Japanese Office Action, Report of Reconsideration by Examiner before Appeal, dated Dec. 2, 2016 for Application No. JP 2013-509247, Appeal No. 2016-016502, 3 pgs.
Japanese Written Statement by Ethicon LLC in response to the Report of Reconsideration by Examiner before Appeal of Dec. 2, 2016, dated Mar. 31, 2017 for Application No. JP 2013-509247, Appeal No. 2016-016502, 7 pgs.

(56) References Cited

OTHER PUBLICATIONS

Japanese Written Argument and Revised Claims by Ethicon LLC in response to the Report of Reconsideration by Examiner before Appeal of Dec. 2, 2016, dated Dec. 22, 2017 for Application No. JP 2013-509247, Appeal No. 2016-016502, 6 pgs.
Japanese Search Report dated Dec. 25, 2015 for Application No. JP 2015-023956, 10 pgs.
Japanese Office Action, Decision to Grant a Patent, dated Jan. 24, 2017 for Application No. JP 2015-023956, 3 pgs.
Korean Office Action, Notice of Final Rejection, dated Jul. 31, 2017 for Application No. KR 10-2012-7031572, 2 pgs.
Korean Office Action, Notice of Preliminary Rejection, dated Jan. 29, 2018 for Application No. KR 10-2017-7030406, 3 pgs.
Korean Office Action, Notification of Reason for Refusal, dated Sep. 18, 2017 for Application No. KR 10-2012-7031614, 6 pgs.
Korean Office Action, Grant of Patent, dated Apr. 23, 2018 for Application No. KR 10-2012-7031614, 2 pgs.
Korean Office Action, Notification of Reason for Refusal, dated Jan. 17, 2017 for Application No. KR 10-2012-7031572, 6 pgs.
Korean Office Action, Notice of Final Rejection, dated Jul. 28, 2017 for Application No. KR 10-2012-7031572, 2 pgs.
Korean Office Action, Notice of Final Rejection, dated Sep. 21, 2017 for Application No. KR 10-2012-7031572, 3 pgs.
New Zealand Office Action, First Examination Report, dated Jun. 20, 2014 for Application No. NZ 626274, 2 pgs.
New Zealand Office Action dated Mar. 11, 2015 for Application No. NZ 705330, 3 pgs.
Singapore Search Report for Singapore Patent Application No. 200702625-5 dated Nov. 26, 2008, 7 pages.
Singapore Search Report for Singapore Patent Application No. 200702350-0 dated Nov. 26, 2008, 6 pages.
Singapore Search Report for Singapore Patent Application No. 200703688-2 dated Nov. 26, 2008, 7 pages.
U.S. Appl. No. 12/392,939, filed Feb. 25, 2009.
U.S. Appl. No. 61/290,750, filed Dec. 29, 2009.
U.S. Appl. No. 61/296,721, filed Jan. 20, 2010.
U.S. Appl. No. 61/331,294, filed May 4, 2010.
U.S. Appl. No. 61/331,302, filed May 4, 2010.
Japanese Office Action, Notice of Reasons for Refusal, dated Oct. 17, 2017 for Application No. JP 2013-509247, Appeal No. 2016-016502, 2 pgs.
Japanese Office Action, Trial and Appeal Decision, dated Feb. 27, 2018 for Application No. JP 2013-509247, Appeal No. 2016-016502, 2 pgs.
Korean Office Action, Trial Decision on Appeal against Decision to Reject Application, dated Jul. 31, 2019, for Application No. KR 2012-7031572, 8 pgs.
Korean Office Action, Grant of Patent, dated Aug. 27, 2019 for Application No. KR 2012-7031572, 2 pgs.
Korean Office Action, Notice of Final Rejection, dated Dec. 3, 2019 for Application No. KR 2017-7030406, 1 pg.

* cited by examiner

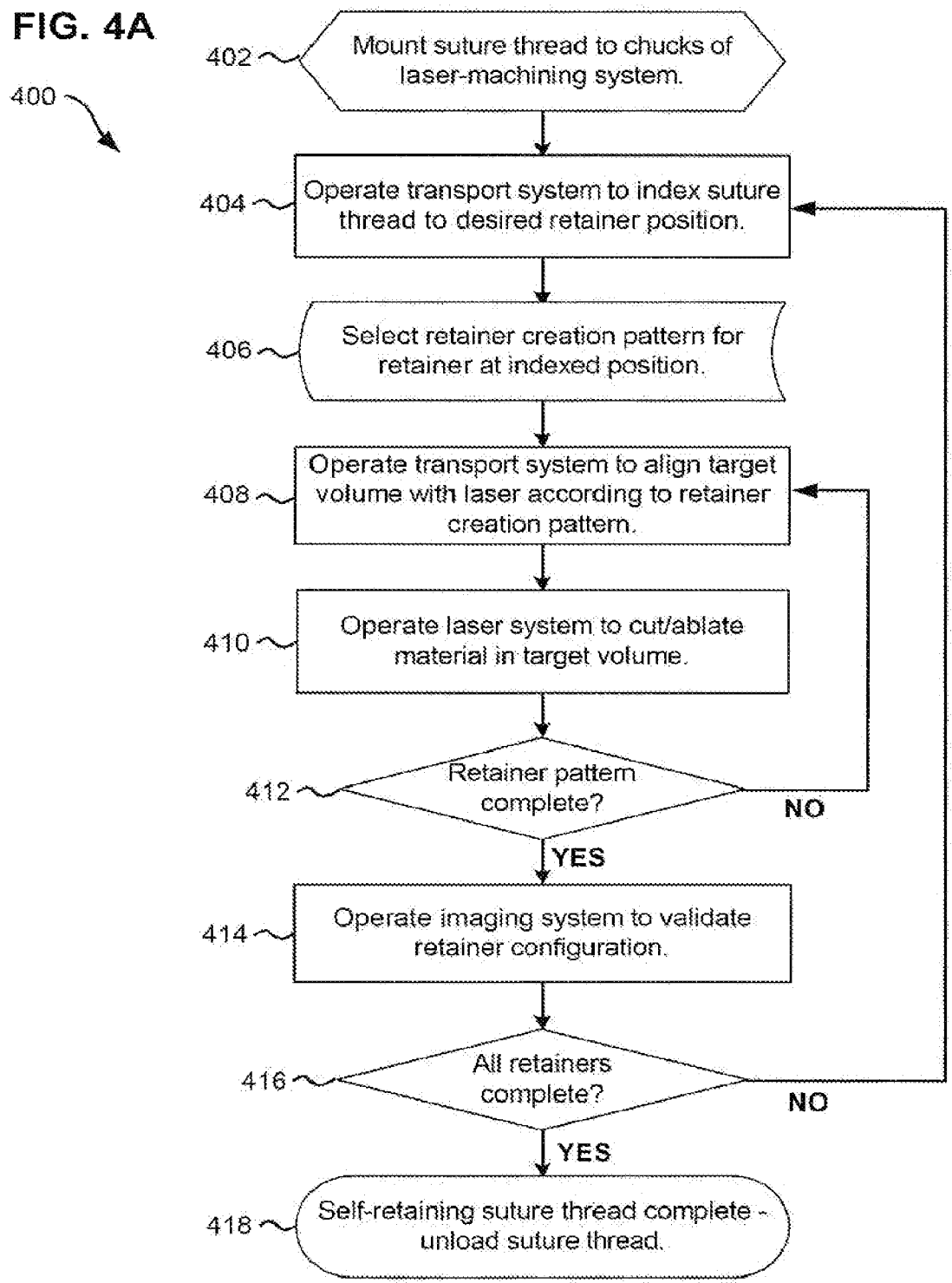

FIG. 9A
| Suture | Holding strength (g) | Tensile strength (g) |
|---|---|---|
| Laser-cut 6-0 prototype no heat treatment or tension applied. | 1.759 | 151.261 |
| Laser-cut 6-0 prototype heat treated at 155C for five minutes. | 55.0683 | 166.105 |
| Laser-cut 6-0 prototype heat treated at 155C under tension for five minutes. | 67.0903 | 138.919 |
| Mechanically-cut quadrahelix self-retaining suture. | 99.8451 | |
| Non barbed 6-0 polypropylene suture. | Knot strength is 200 (110 for 7-0) | 333.174 |
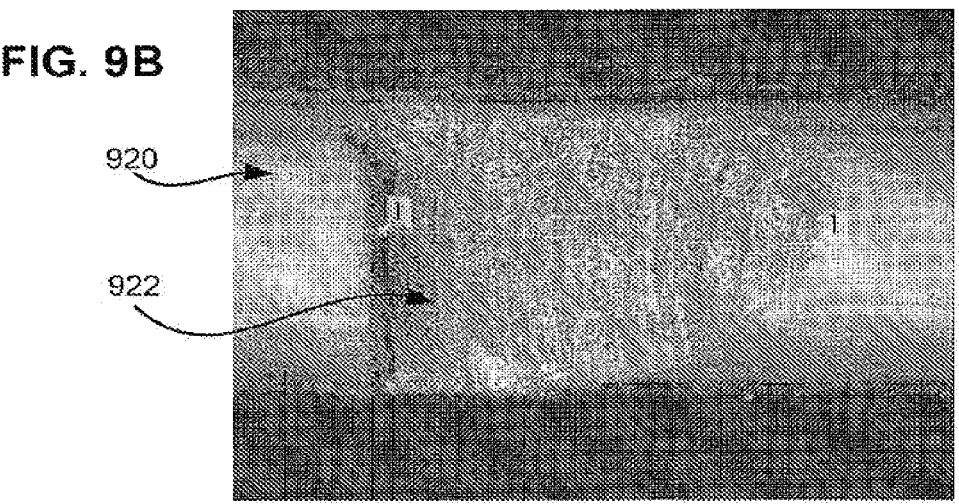
FIG. 9B
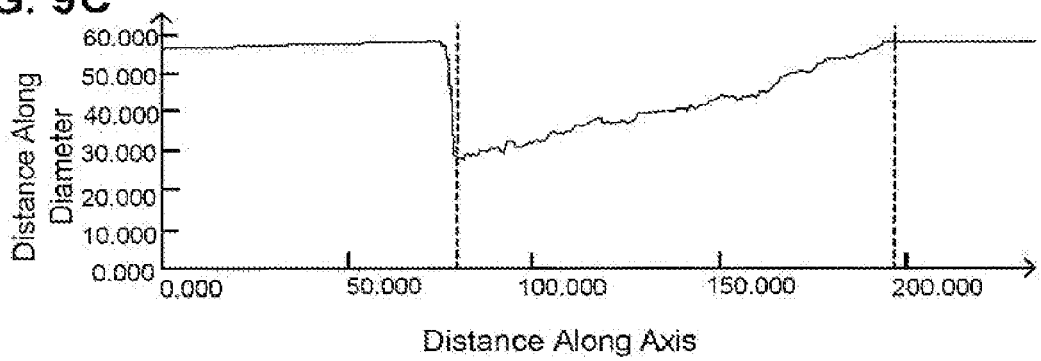
FIG. 9C

SELF-RETAINING SYSTEM HAVING LASER-CUT RETAINERS

CROSS-REFERENCE TO RELATED APPLICATIONS

This application is a National Stage application under 35 U.S.C. 371 of PCT/US2011/035271, filed on May 4, 2011, which claims priority from U.S. Provisional Application Ser. No. 61/331,294, filed on May 4, 2010 and U.S. Provisional Application Ser. No. 61/331,302, filed on May 4, 2010.

FIELD OF INVENTION

This application is a continuation of U.S. patent application Ser. No. 13/695,089, filed on May 8, 2013 and issued as U.S. Pat. No. 10,420,546 on Sep. 24, 2019, which is a National Stage application under 35 U.S.C. 371 of PCT/US2011/035271, filed on May 4, 2011 and published as W.O. Pub. No. 2011/140283 on Nov. 10, 2011, which claims priority from U.S. Provisional Application Ser. No. 61/331,294, filed on May 4, 2010 and U.S. Provisional Application Ser. No. 61/331,302, filed on May 4, 2010.

BACKGROUND OF INVENTION

Wound closure devices such as sutures, staples and tacks have been widely used in superficial and deep surgical procedures in humans and animals for closing wounds, repairing traumatic injuries or defects, joining tissues together (bringing severed tissues into approximation, closing an anatomical space, affixing single or multiple tissue layers together, creating an anastomosis between two hollow/luminal structures, adjoining tissues, attaching or reattaching tissues to their proper anatomical location), attaching foreign elements to tissues (affixing medical implants, devices, prostheses and other functional or supportive devices), and for repositioning tissues to new anatomical locations (repairs, tissue elevations, tissue grafting and related procedures) to name but a few examples.

Sutures are often used as wound closure devices. Sutures typically consist of a filamentous suture thread attached to a needle with a sharp point. Suture threads can be made from a wide variety of materials including bioabsorbable (i.e., that break down completely in the body over time), or non-absorbable (permanent; non-degradable) materials. Absorbable sutures have been found to be particularly useful in situations where suture removal might jeopardize the repair or where the natural healing process renders the support provided by the suture material unnecessary after wound healing has been completed; as in, for example, completing an uncomplicated skin closure. Non-degradable (non-absorbable) sutures are used in wounds where healing may be expected to be protracted or where the suture material is needed to provide physical support to the wound for long periods of time; as in, for example, deep tissue repairs, high tension wounds, many orthopedic repairs and some types of surgical anastomosis. Also, a wide variety of surgical needles are available; the shape and size of the needle body and the configuration of the needle tip is typically selected based upon the needs of the particular application.

To use an ordinary suture, the suture needle is advanced through the desired tissue on one side of the wound and then through the adjacent side of the wound. The suture is then formed into a "loop" which is completed by tying a knot in the suture to hold the wound closed. Knot tying takes time and causes a range of complications, including, but not limited to (i) spitting (a condition where the suture, usually a knot) pushes through the skin after a subcutaneous closure), (ii) infection (bacteria are often able to attach and grow in the spaces created by a knot), (iii) bulk/mass (a significant amount of suture material left in a wound is the portion that comprises the knot), (iv) slippage (knots can slip or come untied), and (v) irritation (knots serve as a bulk "foreign body" in a wound). Suture loops associated with knot tying may lead to ischemia (knots can create tension points that can strangulate tissue and limit blood flow to the region) and increased risk of dehiscence or rupture at the surgical wound. Knot tying is also labor intensive and can comprise a significant percentage of the time spent closing a surgical wound. Additional operative procedure time is not only bad for the patient (complication rates rise with time spent under anesthesia), but it also adds to the overall cost of the operation (many surgical procedures are estimated to cost between $15 and $30 per minute of operating time).

Self-retaining sutures (including barbed sutures) differ from conventional sutures in that self-retaining sutures possess numerous tissue retainers (such as barbs) which anchor the self-retaining suture into the tissue following deployment and resist movement of the suture in a direction opposite to that in which the retainers face, thereby eliminating the need to tie knots to affix adjacent tissues together (a "knotless" closure). Knotless tissue-approximating devices having barbs have been previously described in, for example, U.S. Pat. No. 5,374,268, disclosing armed anchors having barb-like projections, while suture assemblies having barbed lateral members have been described in U.S. Pat. Nos. 5,584,859 and 6,264,675. Sutures having a plurality of barbs positioned along a greater portion of the suture are described in U.S. Pat. No. 5,931,855, which discloses a unidirectional barbed suture, and U.S. Pat. No. 6,241,747, which discloses a bidirectional barbed suture. Methods and apparatus for forming barbs on sutures have been described in, for example, U.S. Pat. No. 6,848,152. Self-retaining systems for wound closure also result in better approximation of the wound edges, evenly distribute the tension along the length of the wound (reducing areas of tension that can break or lead to ischemia), decrease the bulk of suture material remaining in the wound (by eliminating knots) and reduce spitting (the extrusion of suture material—typically knots—through the surface of the skin. All of these features are thought to reduce scarring, improve cosmesis, and increase wound strength relative to wound closures using plain sutures or staples. Thus, self-retaining sutures, because such sutures avoid knot tying, allow patients to experience an improved clinical outcome, and also save time and costs associated with extended surgeries and follow-up treatments. It is noted that all patents, patent applications and patent publications identified throughout are incorporated herein by reference in their entirety.

The ability of self-retaining sutures to anchor and hold tissues in place even in the absence of tension applied to the suture by a knot is a feature that also provides superiority over plain sutures. When closing a wound that is under tension, this advantage manifests itself in several ways: (i) self-retaining sutures have a multiplicity of retainers which can dissipate tension along the entire length of the suture (providing hundreds of "anchor" points this produces a superior cosmetic result and lessens the chance that the suture will "slip" or pull through) as opposed to knotted interrupted sutures which concentrate the tension at discrete points; (ii) complicated wound geometries can be closed (circles, arcs, jagged edges) in a uniform manner with more precision and accuracy than can be achieved with interrupted sutures; (iii) self-retaining sutures eliminate the need for a "third hand" which is often required for maintaining tension across the wound during traditional suturing and knot tying (to prevent "slippage" when tension is momentarily released during tying); (iv) self-retaining sutures are superior in procedures where knot tying is technically difficult, such as in deep wounds or laparoscopic/endoscopic procedures; and (v) self-retaining sutures can be used to approximate and hold the wound prior to definitive closure. As a result, self-retaining sutures provide easier handling in anatomically tight or deep places (such as the pelvis, abdomen and thorax) and make it easier to approximate tissues in laparoscopic/endoscopic and minimally invasive procedures; all without having to secure the closure via a knot. Greater accuracy allows self-retaining sutures to be used for more complex closures (such as those with diameter mismatches, larger defects or purse string suturing) than can be accomplished with plain sutures.

A self-retaining suture may be unidirectional, having one or more retainers oriented in one direction along the length of the suture thread; or bidirectional, typically having one or more retainers oriented in one direction along a portion of the thread, followed by one or more retainers oriented in another (often opposite) direction over a different portion of the thread (as described with barbed retainers in U.S. Pat. Nos. 5,931,855 and 6,241,747). Although any number of sequential or intermittent configurations of retainers are possible, one form of unidirectional self-retaining suture includes a tissue anchor on the distal end and a needle on the proximal end and a plurality of barbs on the surface of the suture thread having tips projecting "away" from the needle. Projecting "away" from the needle means that the tip of the barb is further away from the needle and the portion of suture comprising the barb may be pulled more easily through tissue in the direction of the needle than in the opposite direction (towards the tissue anchor). The tissue anchor is designed to secure the distal end of the suture and includes in some embodiments a loop, staple, tack, bar, plug, sheet, or ball.

Although any number of sequential or intermittent configurations of retainers are possible, one form of bidirectional self-retaining suture includes a needle at one end of a suture thread which has barbs having tips projecting "away" from the needle until the transition point (often the midpoint) of the suture is reached; at the transition point the configuration of barbs reverses itself about 180° (such that the barbs are now facing in the opposite direction) along the remaining length of the suture thread before attaching to a second needle at the opposite end (with the result that the barbs on this portion of the suture also have tips projecting "away" from the nearest needle). Put another way, the barbs on both "halves" of a typical bidirectional self-retaining suture have tips that point towards the middle, with a transition segment (lacking barbs) interspersed between them, and with a needle attached to either end.

SUMMARY OF INVENTION

Despite the multitude of advantages of unidirectional and bidirectional self-retaining sutures, there remains a need to improve upon the design of the suture such that a variety of limitations can be eliminated and enhanced and/or additional functionality is provided.

In accordance with another aspect, the present invention provides retainer designs suitable for cutting on a suture thread with a laser.

In accordance with another aspect, the present invention provides a suture thread having a plurality of laser-cut retainers.

In accordance with another aspect, the present invention provides a unidirectional self-retaining suture system having a plurality of laser-cut retainers.

In accordance with another aspect, the present invention provides a bidirectional self-retaining suture system having a plurality of laser-cut retainers.

The details of one or more embodiments are set forth in the description below. Other features, objects and advantages will be apparent from the description, the drawings, and the claims.

In addition, the disclosures of all patents and patent applications referenced herein are incorporated by reference in their entirety, including, U.S. patent application Ser. No. 12/101,885, filed Apr. 11, 2008, issued as U.S. Pat. No. 8,793,863 on Aug. 5, 2014, entitled "SELF-RETAINING SYSTEMS FOR SURGICAL PROCEDURES"; U.S. patent application Ser. No. 12/392,939, filed Feb. 25, 2009 entitled "ALTERNATIVE GEOMETRY SELF-RETAINING SUTURES SYSTEM"; U.S. patent application Ser. No. 12/340,444, filed Dec. 19, 2008, issued as U.S. Pat. No. 8,916,077 on Dec. 23, 2014, entitled "SELF-RETAINING SUTURES WITH RETAINERS FORMED FROM MOLTEN MATERIALS"; and U.S. patent application Ser. No. 13/695,112, filed Mar. 12, 2013, published as U.S. Pub. No. 2013/0180966 on Jul. 18, 2013, now abandoned, which is a U.S. National Phase of International No. PCT/US2011/035270, filed May 4, 2011, entitled LASER CUTTING SYSTEM AND METHODS FOR CREATING SELF-RETAINING SUTURES, published as W.O. Pub. No. 2011/140282.

BRIEF DESCRIPTION OF THE DRAWINGS

Features of the invention, its nature and various advantages will be apparent from the accompanying drawings and the following detailed description of various embodiments.

FIG. 4A is a flow chart of a method for creating a self-retaining suture utilizing the laser-machining system of FIG. 2A.

FIG. 9A is a table showing the results of mechanical testing of prototype self-retaining sutures made utilizing the laser-machining system of FIG. 2A according to embodiments of the present invention.

FIG. 9B is an image of a laser-cut surface of a self-retaining suture.

FIG. 9C is a graph showing the profile of the laser-cut surface of FIG. 9B.

DETAILED DESCRIPTION

Definitions

Figure 1A:
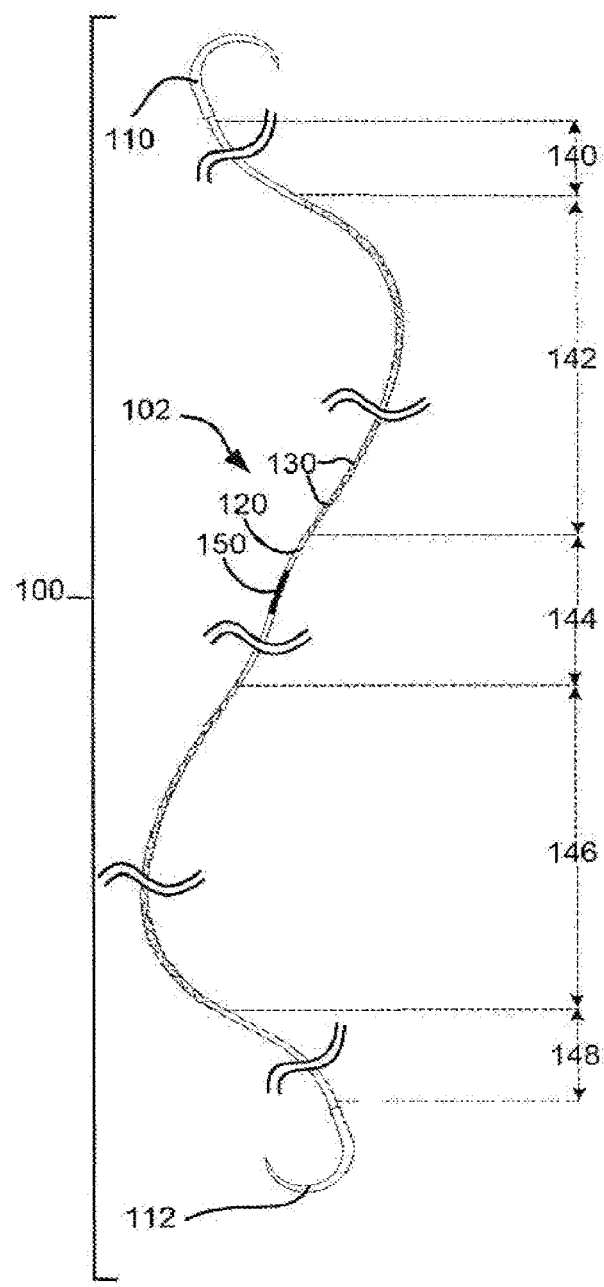
FIG. 1A is a perspective view of a bidirectional self-retaining suture in accordance with an embodiment of the present invention.

Definitions of certain terms that may be used hereinafter include the following.

"Self-retaining system" refers to a self-retaining suture together with devices for deploying the suture into tissue. Such deployment devices include, without limitation, suture needles and other deployment devices as well as sufficiently rigid and sharp ends on the suture itself to penetrate tissue.

"Self-retaining suture" refers to a suture that comprises features on the suture filament for engaging tissue without the need for a knot or suture anchor.

"Tissue retainer" (or simply "retainer") or "barb" refers to a physical feature of a suture filament which is adapted to mechanically engage tissue and resist movement of the suture in at least one axial directions. By way of example only, tissue retainer or retainers can include hooks, projections, barbs, darts, extensions, bulges, anchors, protuberances, spurs, bumps, points, cogs, tissue engagers, traction devices, surface roughness, surface irregularities, surface defects, edges, facets and the like. In certain configurations, tissue retainers are adapted to engage tissue to resist movement of the suture in a direction other than the direction in which the suture is deployed into the tissue by the physician, by being oriented to substantially face the deployment direction. In some embodiments the retainers lie flat when pulled in the deployment direction and open or "fan out" when pulled in a direction contrary to the deployment direction. As the tissue-penetrating end of each retainer faces away from the deployment direction when moving through tissue during deployment, the tissue retainers should not catch or grab tissue during this phase. Once the self-retaining suture has been deployed, a force exerted in another direction (often substantially opposite to the deployment direction) causes the retainers to be displaced from the deployment position (i.e. resting substantially along the suture body), forces the retainer ends to open (or "fan out") from the suture body in a manner that catches and penetrates into the surrounding tissue, and results in tissue being caught between the retainer and the suture body; thereby "anchoring" or affixing the self-retaining suture in place. In certain other embodiments, the tissue retainers may be configured to permit motion of the suture in one direction and resist movement of the suture in another direction without fanning out or deploying. In certain other configurations, the tissue retainer may be configured or combined with other tissue retainers to resist motion of the suture filament in both directions. Typically a suture having such retainers is deployed through a device such as a cannula which prevents contact between the retainers and the tissue until the suture is in the desired location.

"Retainer configurations" refers to configurations of tissue retainers and can include features such as size, shape, flexibility, surface characteristics, and so forth. These are sometimes also referred to as "barb configurations".

"Bidirectional suture" refers to a self-retaining suture having retainers oriented in one direction at one end and retainers oriented in the other direction at the other end. A bidirectional suture is typically armed with a needle at each end of the suture thread. Many bidirectional sutures have a transition segment located between the two barb orientations.

"Transition segment" refers to a retainer-free (barb-free) portion of a bidirectional suture located between a first set of retainers (barbs) oriented in one direction and a second set of retainers (barbs) oriented in another direction. The transition segment can be at about the midpoint of the self-retaining suture, or closer to one end of the self-retaining suture to form an asymmetrical self-retaining suture system.

"Suture thread" refers to the filamentary body component of the suture. The suture thread may be a monofilament, or comprise multiple filaments as in a braided suture. The suture thread may be made of any suitable biocompatible material, and may be further treated with any suitable biocompatible material, whether to enhance the sutures' strength, resilience, longevity, or other qualities, or to equip the sutures to fulfill additional functions besides joining tissues together, repositioning tissues, or attaching foreign elements to tissues.

"Monofilament suture" refers to a suture comprising a monofilamentary suture thread.

"Braided suture" refers to a suture comprising a multifilamentary suture thread. The filaments in such suture threads are typically braided, twisted, or woven together.

"Degradable suture" (also referred to as "biodegradable suture" or "absorbable suture") refers to a suture which, after introduction into a tissue is broken down and absorbed by the body. Typically, the degradation process is at least partially mediated by, or performed in, a biological system. "Degradation" refers to a chain scission process by which a polymer chain is cleaved into oligomers and monomers. Chain scission may occur through various mechanisms, including, for example, by chemical reaction (e.g., hydrolysis, oxidation/reduction, enzymatic mechanisms or a combination of these) or by a thermal or photolytic process. Polymer degradation may be characterized, for example, using gel permeation chromatography (GPC), which monitors the polymer molecular mass changes during erosion and breakdown. Degradable suture material may include polymers such as polyglycolic acid, copolymers of glycolide and lactide, copolymers of trimethylene carbonate and glycolide with diethylene glycol (e.g., MAXON™, Covidien), terpolymer composed of glycolide, trimethylene carbonate, and dioxanone (e.g., BIOSYN™ [glycolide (60%), trimethylene carbonate (26%), and dioxanone (14%)], Covidien), copolymers of glycolide, caprolactone, trimethylene carbonate, and lactide (e.g., CAPROSYN™, Covidien). A dissolvable suture can also include partially deacetylated polyvinyl alcohol. Polymers suitable for use in degradable sutures can be linear polymers, branched polymers or multi-axial polymers. Examples of multi-axial polymers used in sutures are described in U.S. Patent Application Publication Nos. 2002/0161168, now abandoned, 2004/0024169, issued as U.S. Pat. No. 7,026,437 on Apr. 11, 2006, and 2004/0116620, issued as U.S. Pat. No. 7,070,858 on Jul. 4, 2006. Sutures made from degradable suture material lose tensile strength as the material degrades. Degradable sutures can be in either a braided multifilament form or a monofilament form.

"Non-degradable suture" (also referred to as "non-absorbable suture") refers to a suture comprising material that is not degraded by chain scission such as chemical reaction processes (e.g., hydrolysis, oxidation/reduction, enzymatic mechanisms or a combination of these) or by a thermal or photolytic process. Non-degradable suture material includes polyamide (also known as nylon, such as nylon 6 and nylon 6,6), polyester (e.g., polyethylene terephthlate), polytetrafluoroethylene (e.g., expanded polytetrafluoroethylene), polyether-ester such as polybutester (block copolymer of butylene terephthalate and polytetra methylene ether glycol), polyurethane, metal alloys, metal (e.g., stainless steel wire), polypropylene, polyethelene, silk, and cotton. Sutures made of non-degradable suture material are suitable for applications in which the suture is meant to remain permanently or is meant to be physically removed from the body.

"Suture diameter" refers to the diameter of the body of the suture. It is to be understood that a variety of suture lengths may be used with the sutures described herein and that while the term "diameter" is often associated with a circular periphery, it is to be understood herein to indicate a cross-sectional dimension associated with a periphery of any shape. Suture sizing is based upon diameter. United States Pharmacopeia ("USP") designation of suture size runs from 0 to 7 in the larger range and 1-0 to 11-0 in the smaller range; in the smaller range, the higher the value preceding the hyphenated zero, the smaller the suture diameter. The actual diameter of a suture will depend on the suture material, so that, by way of example, a suture of size 5-0 and made of collagen will have a diameter of 0.15 mm, while sutures having the same USP size designation but made of a synthetic absorbable material or a non-absorbable material will each have a diameter of 0.1 mm. The selection of suture size for a particular purpose depends upon factors such as the nature of the tissue to be sutured and the importance of cosmetic concerns; while smaller sutures may be more easily manipulated through tight surgical sites and are associated with less scarring, the tensile strength of a suture manufactured from a given material tends to decrease with decreasing size. It is to be understood that the sutures and methods of manufacturing sutures disclosed herein are suited to a variety of diameters, including without limitation 7, 6, 5, 4, 3, 2, 1, 0, 1-0, 2-0, 3-0, 4-0, 5-0, 6-0, 7-0, 8-0, 9-0, 10-0 and 11-0.

"Needle attachment" refers to the attachment of a needle to a suture requiring same for deployment into tissue, and can include methods such as crimping, swaging, using adhesives, and so forth. The suture thread is attached to the suture needle using methods such as crimping, swaging and adhesives. Attachment of sutures and surgical needles is described in U.S. Pat. Nos. 3,981,307, 5,084,063, 5,102,418, 5,123,911, 5,500,991, 5,722,991, 6,012,216, and 6,163,948, and U.S. Patent Application Publication No. US 2004/0088003, now abandoned. The point of attachment of the suture to the needle is known as the swage.

"Suture needle" refers to needles used to deploy sutures into tissue, which come in many different shapes, forms and compositions. There are two main types of needles, traumatic needles and atraumatic needles. Traumatic needles have channels or drilled ends (that is, holes or eyes) and are supplied separate from the suture thread and are threaded on site. Atraumatic needles are eyeless and are attached to the suture at the factory by swaging or other methods whereby the suture material is inserted into a channel at the blunt end of the needle which is then deformed to a final shape to hold the suture and needle together. As such, atraumatic needles do not require extra time on site for threading and the suture end at the needle attachment site is generally smaller than the needle body. In the traumatic needle, the thread comes out of the needle's hole on both sides and often the suture rips the tissues to a certain extent as it passes through. Most modern sutures are swaged atraumatic needles. Atraumatic needles may be permanently swaged to the suture or may be designed to come off the suture with a sharp straight tug. These "pop-offs" are commonly used for interrupted sutures, where each suture is only passed once and then tied. For barbed sutures that are uninterrupted, these atraumatic needles are preferred.

Suture needles may also be classified according to the geometry of the tip or point of the needle. For example, needles may be (i) "tapered" whereby the needle body is round and tapers smoothly to a point; (ii) "cutting" whereby the needle body is triangular and has a sharpened cutting edge on the inside; (iii) "reverse cutting" whereby the cutting edge is on the outside; (iv) "trocar point" or "taper cut" whereby the needle body is round and tapered, but ends in a small triangular cutting point; (v) "blunt" points for sewing friable tissues; (vi) "side cutting" or "spatula points" whereby the needle is flat on top and bottom with a cutting edge along the front to one side (these are typically used for eye surgery).

Suture needles may also be of several shapes including, (i) straight, (ii) half curved or ski, (iii) ¼ circle, (iv) ⅜ circle, (v) ½ circle, (vi) ⅝ circle, (v) and compound curve.

Suturing needles are described, for example, in U.S. Pat. Nos. 6,322,581 and 6,214,030; and 5,464,422; and 5,941,899; 5,425,746; 5,306,288 and 5,156,615; and 5,312,422; and 7,063,716. Other suturing needles are described, for example, in U.S. Pat. Nos. 6,129,741; 5,897,572; 5,676,675; and 5,693,072. The sutures described herein may be deployed with a variety of needle types (including without limitation curved, straight, long, short, micro, and so forth), needle cutting surfaces (including without limitation, cutting, tapered, and so forth), and needle attachment techniques (including without limitation, drilled end, crimped, and so forth). Moreover, the sutures described herein may themselves include sufficiently rigid and sharp ends so as to dispense with the requirement for deployment needles altogether.

"Needle diameter" refers to the diameter of a suture deployment needle at the widest point of that needle. While the term "diameter" is often associated with a circular periphery, it is to be understood herein to indicate a cross-sectional dimension associated with a periphery of any shape.

"Armed suture" refers to a suture having a suture needle on at least one suture deployment end. "Suture deployment end" refers to an end of the suture to be deployed into tissue; one or both ends of the suture may be suture deployment ends. The suture deployment end may be attached to a deployment device such as a suture needle, or may be sufficiently sharp and rigid to penetrate tissue on its own.

"Wound closure" refers to a surgical procedure for closing of a wound. An injury, especially one in which the skin or another external or internal surface is cut, torn, pierced, or otherwise broken is known as a wound. A wound commonly occurs when the integrity of any tissue is compromised (e.g., skin breaks or burns, muscle tears, or bone fractures). A wound may be caused by an act, such as a puncture, fall, or surgical procedure; by an infectious disease; or by an underlying medical condition. Surgical wound closure facilitates the biological event of healing by joining, or closely approximating, the edges of those wounds where the tissue has been torn, cut, or otherwise separated. Surgical wound closure directly apposes or approximates the tissue layers, which serves to minimize the volume new tissue formation required to bridge the gap between the two edges of the wound. Closure can serve both functional and aesthetic purposes. These purposes include elimination of dead space by approximating the subcutaneous tissues, minimization of scar formation by careful epidermal alignment, and avoidance of a depressed scar by precise eversion of skin edges.

'Tissue elevation procedure" refers to a surgical procedure for repositioning tissue from a lower elevation to a higher elevation (i.e. moving the tissue in a direction opposite to the direction of gravity). The retaining ligaments of the face support facial soft tissue in the normal anatomic position. However, with age, gravitational effects and loss of tissue volume effect downward migration of tissue, and fat descends into the plane between the superficial and deep facial fascia, thus causing facial tissue to sag. Face-lift procedures are designed to lift these sagging tissues, and are one example of a more general class of medical procedure known as a tissue elevation procedure. More generally, a tissue elevation procedure reverses the appearance change that results from effects of aging and gravity over time, and other temporal effects that cause tissue to sag, such as genetic effects. It should be noted that tissue can also be repositioned without elevation; in some procedures tissues are repositioned laterally (away from the midline), medially (towards the midline) or inferiorly (lowered) in order to restore symmetry (i.e. repositioned such that the left and right sides of the body "match").

"Medical device" or "implant" refers to any object placed in the body for the purpose of restoring physiological function, reducing/alleviating symptoms associated with disease, and/or repairing and/or replacing damaged or diseased organs and tissues. While normally composed of biologically compatible synthetic materials (e.g., medical-grade stainless steel, titanium and other metals or polymers such as polyurethane, silicon, PLA, PLGA and other materials) that are exogenous, some medical devices and implants include materials derived from animals (e.g., "xenografts" such as whole animal organs; animal tissues such as heart valves; naturally occurring or chemically-modified molecules such as collagen, hyaluronic acid, proteins, carbohydrates and others), human donors (e.g., "allografts" such as whole organs; tissues such as bone grafts, skin grafts and others), or from the patients themselves (e.g., "autografts" such as saphenous vein grafts, skin grafts, tendon/ligament/muscle transplants). Medical devices that can be used in procedures in conjunction with the present invention include, but are not restricted to, orthopedic implants (artificial joints, ligaments and tendons; screws, plates, and other implantable hardware), dental implants, intravascular implants (arterial and venous vascular bypass grafts, hemodialysis access grafts; both autologous and synthetic), skin grafts (autologous, synthetic), tubes, drains, implantable tissue bulking agents, pumps, shunts, sealants, surgical meshes (e.g., hernia repair meshes, tissue scaffolds), fistula treatments, spinal implants (e.g., artificial intervertebral discs, spinal fusion devices, etc.) and the like.

Laser-Cut Self-Retaining Sutures

As discussed above, the present invention provides self-retaining suture having laser-cut retainers, methods of manufacturing and methods of using such sutures in surgical procedures which eliminate a variety of limitations and provide enhanced and/or additional functionality. FIG. 1A illustrates a laser-cut self-retaining suture system 100. Self-retaining suture system 100 comprises needles 110, 112 attached to self-retaining suture thread 102. Self-retaining suture thread 102 includes a plurality of retainers 130 distributed on the surface of a filament 120. In lead-in section 140 of filament 120 there are no retainers 130. In section 142 of filament 120 there are a plurality of retainers 130 arranged such that the suture can be deployed in the direction of needle 110, but resists movement in the direction of needle 112. In transition section 144, there are no retainers 130. In section 146, there is a plurality of retainers 130 arranged such that the suture can be deployed in the direction of needle 112, but resists movement in the direction of needle 110. In lead-in section 148 of filament 120 there are no retainers 130. A break is shown in each of sections 140, 142, 144, 146 and 148 to indicate that the length of each section may be varied and selected depending upon the application for which the suture is intended to be used. For example, transition section 144 can be asymmetrically located closer to needle 110 or needle 112, if desired.

Self-retaining suture system 100 is composed of two arms. Each arm may be considered to be a section of self-retaining suture system 100. The first arm includes sections 142 and section 140 of self-retaining suture thread 102 and a curved needle 110 has relatively small retainer suitable for engaging harder/denser tissue. The second arm includes sections 146 and 148 and needle 112 of self-retaining suture thread 102.

Although self-retaining suture system 100 of FIG. 1A has two arms, in alternative embodiments, a self-retaining suture system has single-armed sutures; dual-armed sutures; triple-armed sutures; multiple-armed sutures; heterofunctional sutures having two or more sections of suture having different features; dual-arm sutures having different types (or sizes) of needles on each end; single or dual-armed sutures for use with different layers/depth and types of tissue; single or dual armed sutures with sections of filament having different diameters for use with different layers/depth and types of tissue.

Retainers 130 are laser-cut retainers formed on the surface of filament 120 by cutting and/or ablating portions of the filament with a laser as described below. The retainers 130 are in some embodiments identical to one another. In alternative embodiments, retainers 130, vary in shape, dimensions and/or distribution in different sections and/or within sections of the self-retaining suture thread 102 as best suited for engaging tissue. It is an advantage of self-retaining suture system having laser-cut retainers that it is feasible to create multiple configurations of retainers on a suture thread with a single cutting device as will be described below.

Figure 1B:
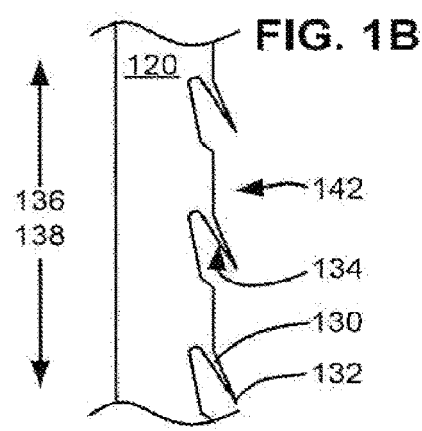
FIGS. 1B-1D are enlarged views of portions of the suture of FIG. 1A.

FIG. 1B illustrates a magnified view of self-retaining suture thread 102 in section 142. As shown in FIG. 1B, a plurality of retainers 130 is distributed on the surface of filament 120. The affixation of self-retaining sutures after deployment in tissue entails the penetration of retainer ends 132 into the surrounding tissue resulting in tissue being caught between the retainer 130 and the body of suture filament 120. The inner surface 134 of the retainer 130 that is in contact with the tissue that is caught between the retainer 130 and the body of filament 120, is referred to herein as the "tissue engagement surface" or "inner retainer surface." As illustrated in FIG. 1B, each retainer 130 has a tip 132 and tissue retainer surface 134. When self-retaining suture thread 102 is moved in the direction of arrow 136, retainers 130 lies flat against the body of filament 120. However, when self-retaining suture thread 102 is moved in the direction of arrow 138, tip 132 of retainer 130 engages tissue surrounding filament 120 and causes retainer 130 to fan out from filament 120 and engage the tissue with tissue engagement surface 134 thereby preventing movement of the suture in that direction.

Figure 1C:
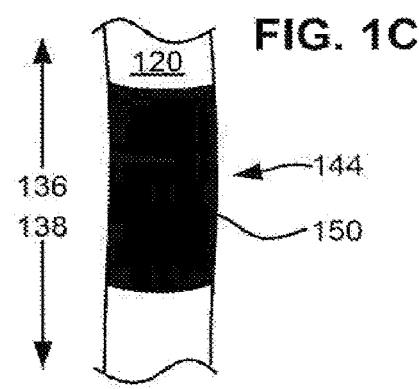

FIG. 1C illustrates a magnified view of self-retaining suture thread 102 in section 144. As shown in FIG. 1C, in section 144, there are no retainers 130. Section 144 may be referred to as the transition section of self-retaining suture system 100. Section 144 may be deployed in either both of the directions shown by arrows 136 and 138. In many procedures it is desirable to locate the transition region in order to properly situate the transition region at the beginning of suture deployment. Thus, the filament 120 in section 144 is, in some embodiments, provided with an identifiable feature. For example, as shown in FIGS. 1A and 1C, section 144 of self-retaining suture system 100 is provided with an identifiable marker in the form of visible band 150. Band 150 represents a portion of filament 120 having a different visible characteristic than other portions of filament 120 which can thus be identified by a surgeon in order to identify and locate the transition section 144 of self-retaining suture system 100. In alternative embodiments, markers are provided on other sections of the filament and/or needles in order to identify features of the self-retaining suture system associated with the section marked. Additionally, marker differences can include different shapes, different colors, different numbers, and different letters to name a few types of markers.

Figure 1D:
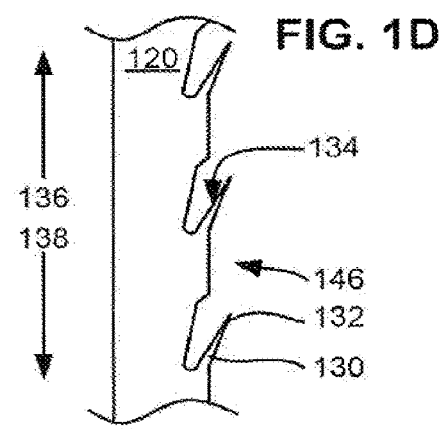

FIG. 1D illustrates a magnified view of self-retaining suture thread 102 in section 146. As shown in FIG. 1D, a plurality of retainers 130 is distributed on the surface of filament 120. As illustrated in FIG. 1D, each retainer 130 has a tip 132 and tissue retainer surface 134. When self-retaining suture thread 102 is moved in the direction of arrow 138, retainer 130 lies flat against the body of filament 120. However, when self-retaining suture thread 102 is moved in the direction of arrow 136, tip 132 or retainer 130 engages tissue surrounding filament 120 and causes retainer 130 to fan out from filament 120 and engage the tissue with face 134, thereby preventing movement of the suture in that direction. Thus, in section 146 retainers 130 are oriented in the opposite direction to the retainers 130 in section 142.

Figure 1E:
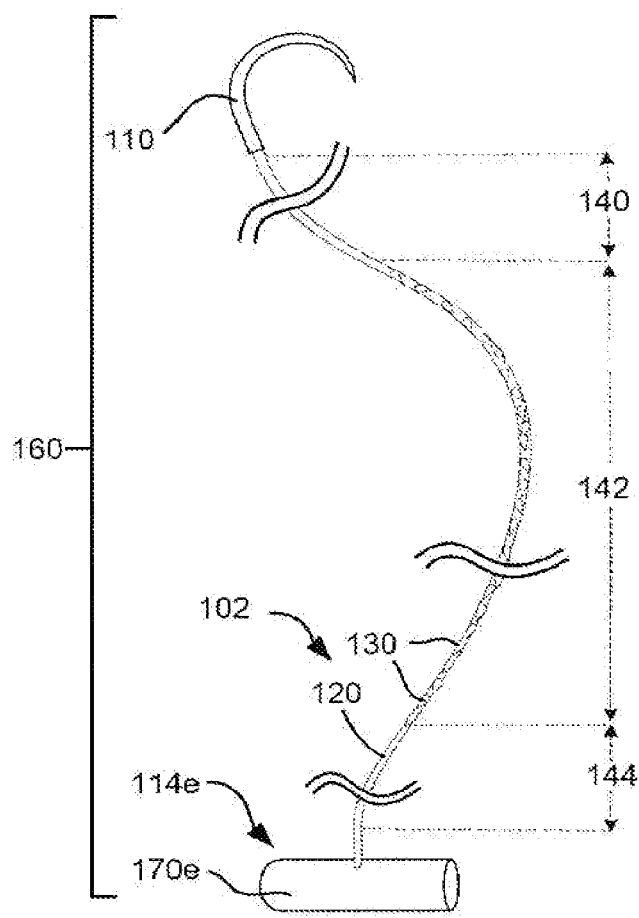
FIG. 1E is a perspective view of a unidirectional self-retaining suture in accordance with an embodiment of the present invention.

FIG. 1E illustrates an alternative embodiment of a self-retaining suture system 160. Self-retaining suture system 160 includes needle 110 and sections 140, 142 and 144 of self-retaining suture system 100 of FIG. 1A. However, self-retaining suture system 160 is a single-armed system. As shown in FIG. 1E, filament 120 terminates following section 146 in a tissue anchor 114e. Tissue anchor 114e is a device for engaging tissue and preventing filament 120 from moving through tissue in the direction of needle 110. Tissue anchor 114e is in some embodiments formed in one piece with filament 120 or formed separately and subsequently attached to filament 120. As shown in FIG. 1E, tissue anchor 114e has a bar-shaped body 170e which extends approximately perpendicular to the axis of filament 120. Bar-shaped body 170e is sufficiently long and stiff to preclude movement of filament 120 in the direction of needle 110 after tissue anchor 114e has engaged a tissue.

Figure 1F:
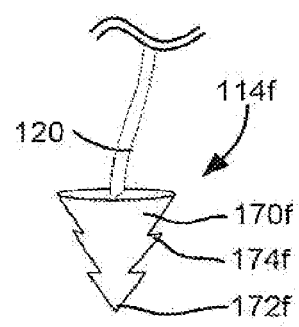
FIGS. 1F-1H are views of alternative tissue anchors for the unidirectional self-retaining suture of FIG. 1E in accordance with alternative embodiments of the present invention.

FIG. 1F shows an alternative anchor 114f which could be used in place of tissue anchor 114e of FIG. 1E. As shown in FIG. 1F, tissue anchor 114f comprises a conical body 170f. Conical body 170f has a pointed end 172f and tissue engaging features 174f which consist of ribs and/or barbs. Tissue anchor 114f is configured to be pushed into tissue in order to anchor filament 120 to that tissue and preclude movement of filament 120 in the direction of needle 110.

Figure 1G:
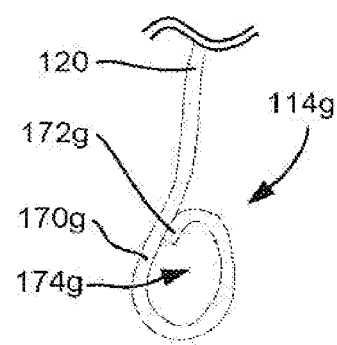

FIG. 1G shows an alternative anchor 114g which could be used in place of tissue anchor 114e of FIG. 1E. As shown in FIG. 1G, tissue anchor 114g comprises a loop 170g. Loop 170g is, in this embodiment, formed by folding back the end 172g of filament 120 and securing end 172g to filament 120 by welding, fusing and/or adhesive. Loop 170g is thus formed from the material of filament 120. Loop 170g has an aperture 174g through which needle 110 can pass in order to create a noose which can be used to engage tissue and preclude movement of filament 120 in the direction of needle 110.

Figure 1H:
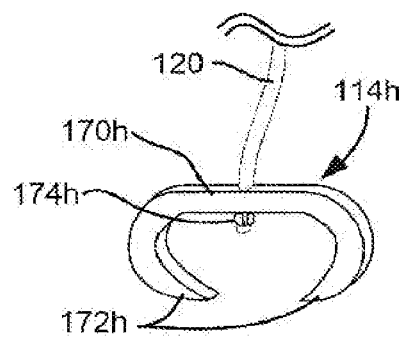

FIG. 1H shows an alternative anchor 114h which could be used in place of tissue anchor 114e of FIG. 1E. As shown in FIG. 1H, tissue anchor 114h comprises a staple-shaped body 170h. Filament 120 passes through an aperture in anchor 114h and is secured by a crimp 174h. Staple-shaped body 170h has two points pointed end 172h which can be deformed towards each other to engage tissue and preclude movement of filament 120 in the direction of needle 110.

Laser-Machining System for Creating Self-Retaining Sutures

In embodiments of the present invention, a laser machining system is utilized to create retainers on the surface of a suture thread and/or provide visible markings on the suture thread. The laser machining system uses a focused beam of coherent light to selectively cut and/or ablate material from a suture thread to generate retainers having a desired configuration on the suture thread. The cutting/ablating process is a noncontact process. A suitable laser machining system has very high spatial confinement and control and very low heat deposition to the suture thread so as to prevent damage to the suture thread during retainer formation.

In general, a laser machining system is used to apply a laser beam to a volume of material within a suture thread. The laser energy is absorbed by the material which is thereby vaporized and removed. The suture thread is, in some embodiments, provided with a component which promotes absorption of the laser energy. The laser light is provided at power, wavelength, and pulse duration selected to vaporize the selected volume of suture material without damaging the remaining suture thread. The wavelength of the laser is typically in the range of UV to visible to infrared light. Light as used herein is not limited to the visible spectrum. The ideal wavelength or spectrum of wavelengths is selected to achieve the best cutting/ablation characteristics.

The exposure required to cause the ablation/cutting may be accomplished in one continuous exposure or a plurality of pulses. Exposure to a plurality of laser pulses allows the energy of each laser pulse to dissipate and therefore induces a lower temperature rise in the suture thread than one continuous pulse of the same total length. The power of the laser beam and/or pulse duration are controlled to cut/ablate the desired material while delivering insufficient total energy to the surrounding material to adversely affect the bulk material properties of the suture thread. For example, in a preferred embodiment a femtosecond laser is used which provides high power for very short duration laser pulses. The wavelength, power, focus and/or pulse duration are also controlled to achieve the desired penetration of the laser into the suture thread.

A variety of different lasers and control system can be used to direct the laser to the selected locations of a suture to create the retainers. In some embodiments, a steered beam system is used to achieve the desired cutting/ablation. In a steered beam system a pulsed laser is directed at a moving point on the suture thread. Mirrors mounted on computer-controlled galvanometers are used to direct the laser beam at targeted volumes of the suture thread. In alternative embodiments, a mask or other optics are used to generate a shaped laser beam having a suitable shape for achieving the desired cutting/ablation. In alternative embodiments, a stepwise pattern is used to create the laser marked indicia. A volume of the suture material is targeted and ablated/cut by modulating a laser on and off. The suture and/or laser is then moved to align a new target volume with the laser and the new target is ablated/cut by modulating the laser on and off. The process is continued to direct the beam stepwise or to move the suture thread stepwise until the desired retainer configuration is achieved.

Figure 2A:
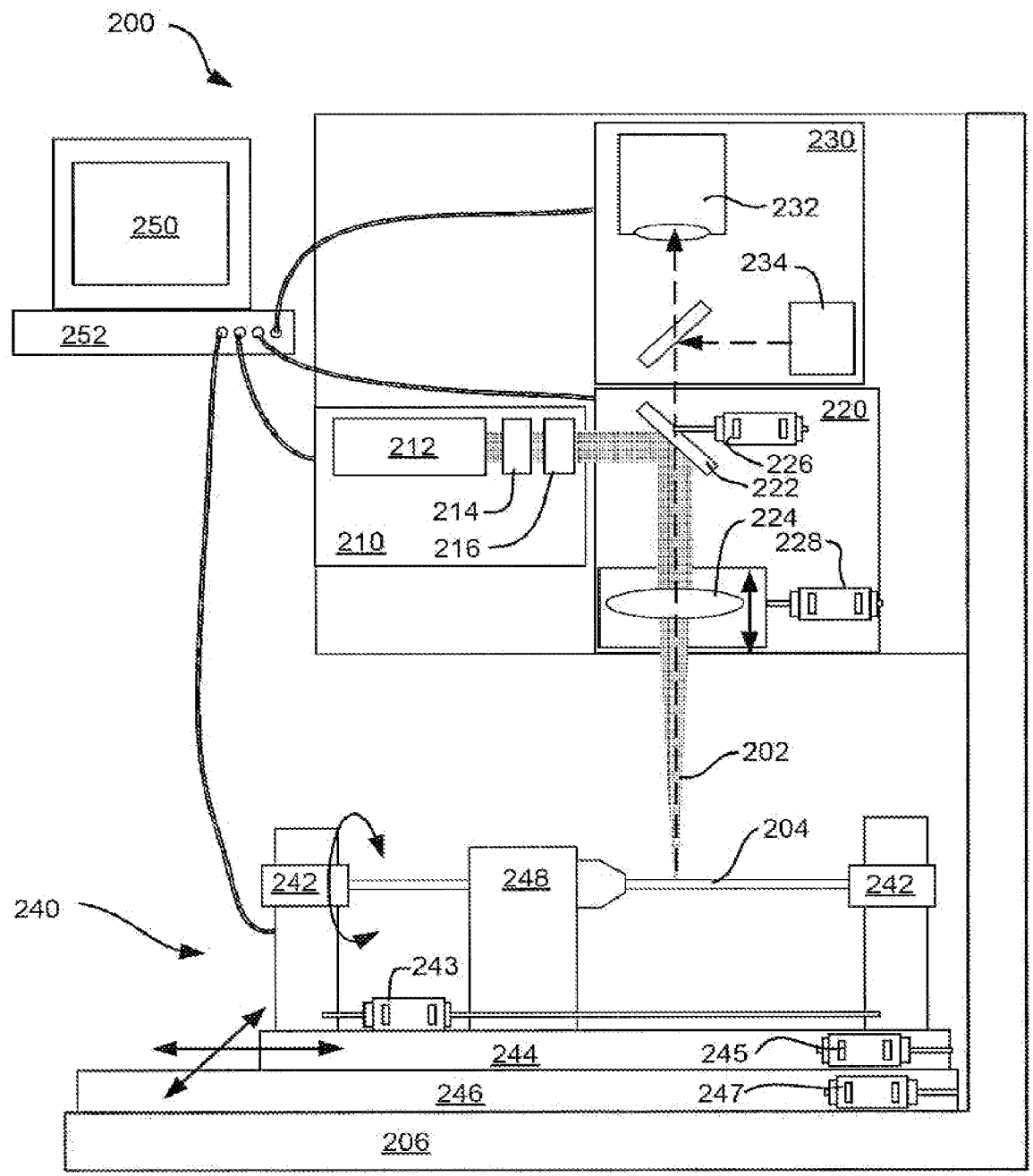
FIG. 2A shows a schematic diagram of a laser-machining system suitable for forming retainers on a suture thread.

FIG. 2A is a schematic diagram of a laser-machining system suitable for manufacturing self-retaining sutures. As shown in FIG. 2A, a laser-machining system 200 includes five subsystems. The five subsystems of laser-machining system 200 are laser subsystem 210, optics subsystem 220, imaging subsystem 230, transport subsystem 240 and control subsystem 250. Laser subsystem 210 supplies laser power to laser machining system 200 in the form of laser beam 202. Laser subsystem 210 is under control of control subsystem 250. Laser subsystem 210 includes laser 212, laser attenuator 214 and laser homogenizer 216. Laser 212 generates laser beam 202. Laser attenuator 214 modulates laser beam 202, allowing it to pass and blocking it as necessary under control of control subsystem 250. Laser homogenizer 216 modifies the laser beam 202 to produce an even power density across laser beam 202.

In a preferred embodiment, laser subsystem 210 is a femtosecond laser system. A femtosecond laser system provides ultra short pulses of laser energy suitable for cutting/ablating material from a suture thread with a high degree of accuracy and without causing damage to the surrounding suture thread. By using femtosecond laser pulses, the laser energy is deposited into small volumes of material by optical absorption followed by avalanche ionization of the material. The laser energy is deposited at a time scale much shorter than the timescale for heat transport in the material. Thus, the material targeted by the laser beam is transformed from solid to vapor phase and to plasma formation almost instantaneously and without significant heat transfer to the surrounding material. The femtosecond laser pulses thus reduce thermal damage to the suture thread.

A femtosecond laser is advantageous because it can achieve: high resolution and repeatability in a fully automated system; high aspect ratios for cutting/ablation of suture thread with low redeposition of ablated material; very localized effects and little damage to suture thread adjacent cutting/ablation zone; and effective cutting of suture thread material over a wide range of materials and diameters (including, for example USP 12-0 to 7). For example, a femtosecond laser system can cut/ablate suture material with submicron resolution and nanometer scale surface roughness of cut surfaces. The parameters of the femtosecond laser can be adjusted to achieve the desired resolution, aspect ratio and reduce collateral damage including by selecting: the appropriate wavelength or combination of wavelengths; the power distribution of the beam (Gaussian, square wave, axiconic); the beam energy and pulse duration; and the focal length and depth of focus for the optics system. The parameters are in some cases modified for different suture thread materials and diameters and retainer configurations.

Laser beam 202 passes from laser subsystem 210 to optics subsystem 220. Optics subsystem 220 includes one or more mirrors 222 and lenses for directing and/or focusing laser beam 202 at a desired target. In particular, optics subsystem 220 includes an object lens 224 from which laser beam 202 leaves optic subsystem 220 towards the desired target. Optics subsystem 220 also includes one or more actuators 226, 228 under control of computer subsystem 250 for adjusting the positions of the mirror(s) 222 and lens(es) 224.

Imaging subsystem 230 allows observation of suture thread 204 and monitoring of the results of laser machining upon it. Imaging subsystem 230 includes an imaging device 232 which is in some embodiments a camera. Imaging system also includes an illumination device 234 for illuminating suture thread 120. Imaging subsystem 230 can also include one or more mirrors and lenses for directing light to and from suture thread 202. Imaging subsystem 230 provides images of suture thread 204 to control subsystem 250. In a preferred embodiment, imaging subsystem 230 is provided in-line with optics subsystem 220 as shown. That is to say that illumination device 234 delivers illumination to suture thread 204 and imaging device 232 receives an image of suture thread 204 through the optic subsystem 220. The images of suture thread 204 can be used by control subsystem 250 to verify the correct operation of the laser subsystem 210 and optics subsystem 220 and make configuration adjustments as necessary. Advantageously image data from the imaging subsystem 230 can be used by the control subsystem 250 to monitor and adjust the depth of focus of the optic system to allow proper focusing and targeting of the laser beam. In alternative embodiments, an off-line imaging system can be used. The images of the suture thread 204 can also be used for quality control of retainer formation including, in some embodiments, validating the correct creation of 100% of the retainers.

Transport subsystem 240 operates to support suture thread 204 and move suture thread 204 relative to laser beam 202. The laser subsystem 210, imaging subsystem 230, optics subsystem 220 and transport subsystem 240 are all securely mounted to a bench 206 to prevent relative movement/vibration of the systems except as controlled by transport subsystem 240. Transport subsystem 240 includes chucks 242 for holding each end of suture thread 204. Chucks 242 are preferably driven by an actuator 243 which drives rotation of suture thread 204 around the longitudinal axis of the suture thread 204. Chucks 242 are mounted to an XY positioning stages 244, 246. XY positioning stages 244, 246 are preferably driven by actuators 245, 247 which control the position of the suture thread 204 relative to the laser beam 202. XY positioning stages 244, 246 are preferably aligned with the longitudinal axis of suture thread 204 such that one stage controls movement of the suture thread along its longitudinal axis relative to laser beam 202 and the other stage controls movement of suture thread 204 perpendicular to the longitudinal axis (across the laser beam 204). Actuators 243, 245, 247 are preferably under the control of control subsystem 250. Transport subsystem 240, in some embodiments, includes a suture spool and mechanism (not shown) for automatically feeding lengths of suture thread to be held between chucks 242 without the need for rethreading the suture thread.

Transport subsystem 240 also includes a stabilization device 248 for stabilizing suture thread 204 adjacent the laser beam 202. Stabilization device 248 reduces movement of suture thread 204 adjacent the cutting region in order to enhance the accuracy of the laser machining operation. In preferred embodiment stabilization device 248 is an air bearing which provides a stream of air to stabilize suture thread 204 without mechanically contacting suture thread 204. The stream of air also serves to cool the suture thread 204 and eliminate smoke and particles from the cutting region.

Control subsystem 250 is a general purpose machine control system having outputs for controlling actuators and inputs for receiving data from machine sensors. Control subsystem 250 includes memory for program and data storage. The program and data storage includes parameters for operation of the laser subsystem 210, optics subsystem 220, imaging subsystem 230, and transport subsystem 240 and/or recorded diagnostic and performance data concerning the operation of laser machining system 200. Data may be stored in control subsystem 250 or other data storage associated with the local network or WAN. Data may be stored in a single format or in multiple formats. Data may be stored on a single type of media or on multiple types of media e.g. hard disks, RAM, flash memory, floppy disks, web-storage systems, etc.

Control subsystem 250 includes one or more processors 252 which can be a computer processer, CPU, and typically includes a microcontroller, CPU, microprocessor or equivalent control circuitry or processor, designed specifically for controlling the laser machining system 200, and may further include RAM or ROM memory, logic and timing circuitry, state machine circuitry, and I/O circuitry. The control system contains and/or has access to programs and/or data which define the distribution of retainers to be formed on a filament and the shape/shapes of the retainers to be formed on the filament as well as the tolerances for the expected shape/shapes of the retainers. The details of the design of control subsystem 250 are not critical to the present invention. Rather, any suitable control subsystem 250 may be used that carries out the functions described herein. The use of computer/microprocessor-based control systems for controlling machine tools is well known in the art.

Figure 2B:
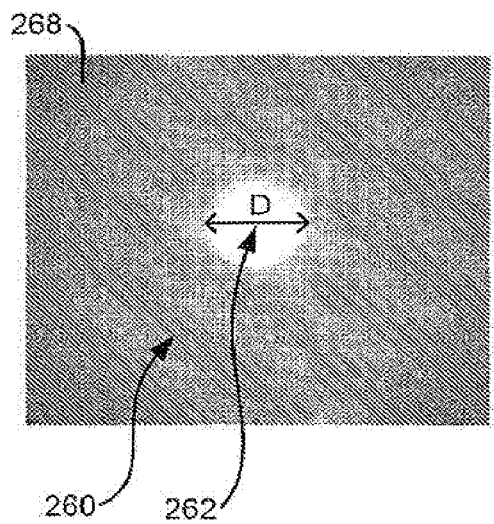
FIG. 2B is an image of a Gaussian laser beam.
Figure 2C:
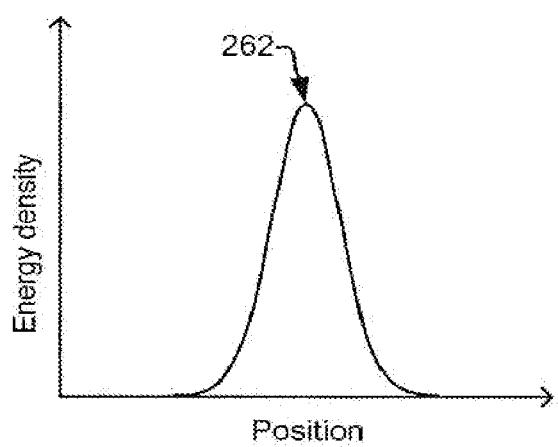
FIG. 2C is a graphical representation of the power density distribution in a Gaussian laser beam.

In an embodiment, the laser beam provided by laser subsystem 210 and optic subsystem 220 has a Gaussian power density distribution. FIG. 2B shows a representative image of a Gaussian laser beam 260 incident on a planar surface 268. As shown in FIG. 2B, the power density of Gaussian beam 260 drops off rapidly moving away from a peak at the center 262 of the beam 260. The diameter D of the zone of peak power density can be altered using the optic subsystem to focus the laser beam. FIG. 2C shows a graphical representation of the power density distribution of Gaussian laser beam (such as laser beam 260 of FIG. 2B).

An alternative laser beam shape/power distribution can be achieved by the use of an axicon prism system utilizing two axicon (rotationally revolved prism) and a lens. The first axicon produces a ring, the lens focuses the ring to a thin (5 micron) width and the second axicon collimates the ring. Varying the distance between the axicon prisms provides the ability to control the diameter of the ring from 0 microns to 300 microns while maintaining focus. The axicon prism system can be used to machine cones into the suture material at an angle. Cones of various diameters are used in a laser machining process to remove material from a filament. By adjusting the cone diameter and the angle of cone relative to the retainer/filament a wide variety of retainer configuration can be machined which would not be possible with a standard laser beam or mechanical cutting. For example, the cone produced by the axicon pair is in some embodiments set to be near 0 diameter, progressively getting larger while the focus of the laser is translated into the suture removing a 3D cone shape of suture material (at a compound angle relative to a retainer to be formed). The laser power is coordinated with the cone diameter to maintain a constant energy density in the ring regardless of ring diameter.

Figure 2D:
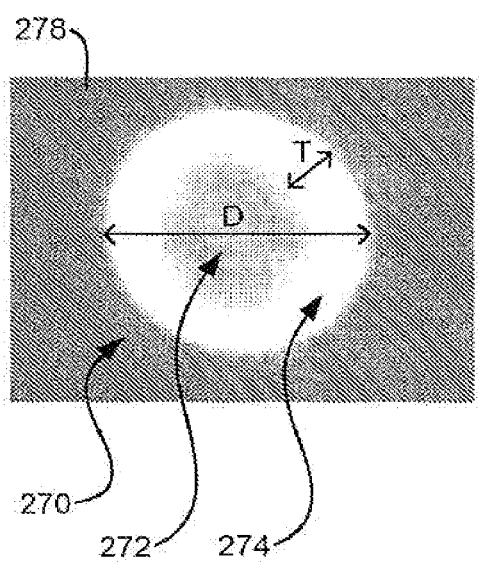
FIG. 2D is an image of a laser beam from an axicon prism system.
Figure 2E:
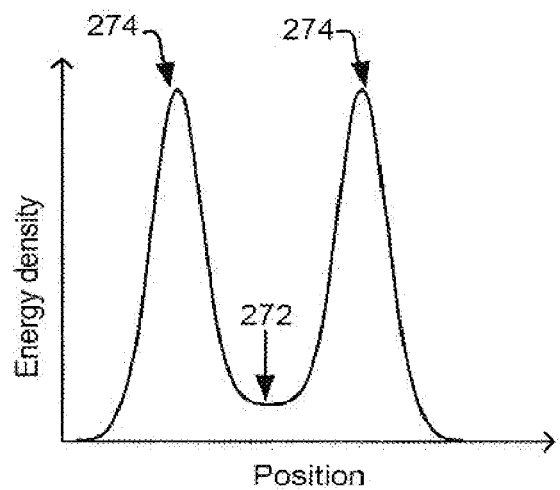
FIG. 2E is a graphical representation of the power density distribution in a laser beam from an axicon prism system.

FIG. 2D shows a representative image of a laser beam 270 from an axicon prism system incident on a planar surface 278. As shown in FIG. 2E the laser beam has a low power density at the center 272. The power density increases travelling away from center 272 until it peaks in ring 274. The power density then drops off rapidly moving outward from ring 274. The diameter D of ring 274 can be controlled by changing the distance between the axicon prisms. The thickness T of the ring can be controlled using the lens between the axicon prisms to focus the ring. FIG. 2E shows a graphical representation of the power density distribution of a laser beam (such as laser beam 270 of FIG. 2D) from an axicon prism system.

Figure 3A:
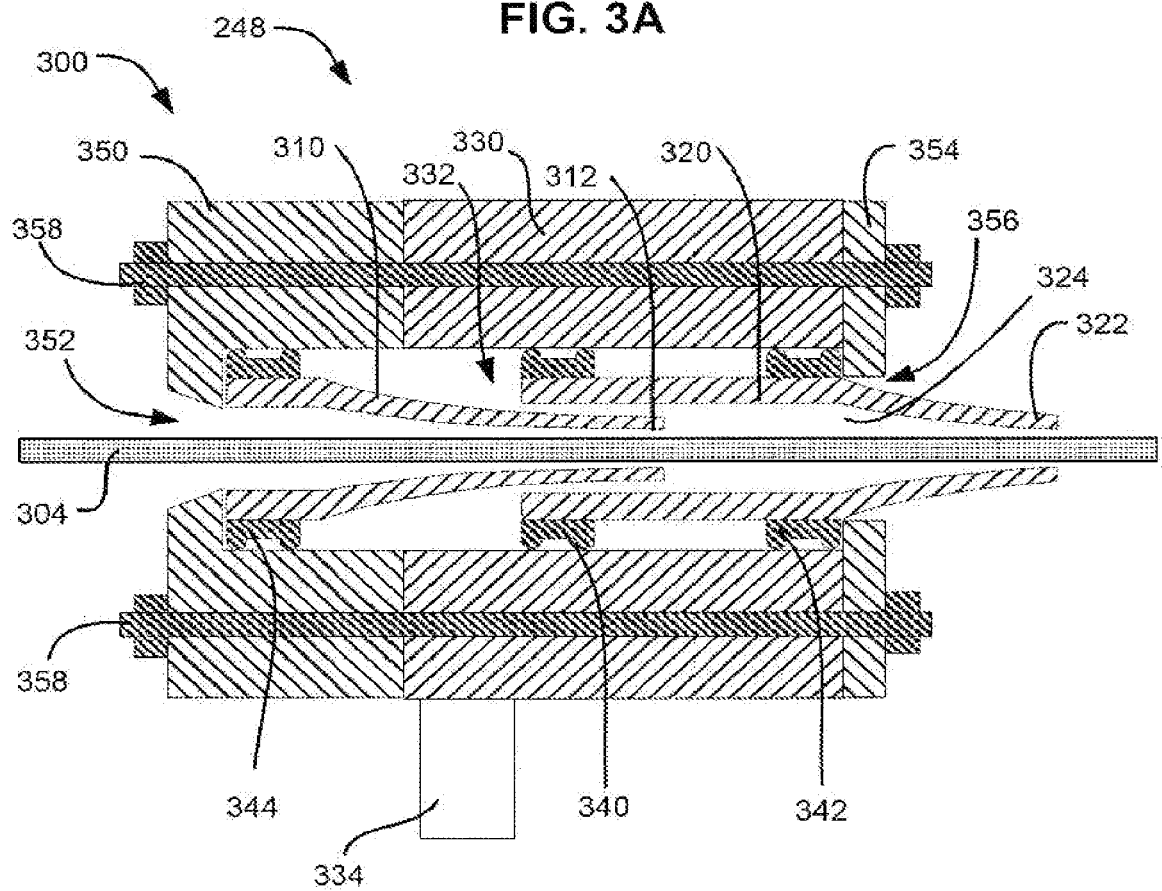
FIG. 3A shows a sectional view of an air bearing for use in the laser-machining system of FIG. 2A.

FIG. 3A shows a sectional view of an embodiment of a stabilization device 248 for stabilizing suture thread 204 adjacent the laser beam 202 (see FIG. 2A). The stabilization device 248 reduces movement of suture thread 204 adjacent the cutting region in order to enhance the accuracy of the laser machining operation (see FIG. 2A). As shown in FIG. 3A, a preferred embodiment of stabilization device 248 is an air bearing 300 which provides a stream of air to stabilize suture thread 304 without mechanically contacting suture thread 304. FIG. 3A shows a sectional view of an air bearing 300 which can be included in stabilization device 248 of FIG. 2A. As shown in FIG. 3A, air bearing comprises an entry nozzle 310 and an exit nozzle 320. Entry nozzle 310 and exit nozzle 320 have tips 312, 322 which have an inside diameter similar approximately two suture diameters in diameter. In preferred embodiments, different nozzles are used for suture threads of different size. Entry nozzle 310 and exit nozzle 320 can be made by drawing down a glass tube to the appropriate diameter for a particular suture thread and cutting and grinding the tip 312, 322.

As shown in FIG. 3A, exit nozzle 320 is mounted within a cavity 332 of a manifold 330. O-rings 340, 342 seal exit nozzle 320 to the surface of cavity 332. Manifold 330 is machined to deliver pressurized air from an intake line 334 evenly around cavity 332. Entry nozzle 310 is positioned with tip 312 within the lumen of exit nozzle 320 as shown. Entry nozzle 310 and exit nozzle 320 are positioned coaxially. Entry nozzle 310 is aligned and secured in position by entry cap 350. An o-ring 344 seals entry nozzle 310 to entry cap 350. Entry cap 350 has a chamfered entry port 352 which is positioned coaxial with entry nozzle 310 and exit nozzle 320. An exit cap 354 is mounted on the other end of manifold 330. Exit cap 354 has an exit port 356 through which exit nozzle 320 protrudes. Entry cap 350, manifold 330 and exit cap 354 are secured together by a plurality of fasteners 358.

A suture thread 304 can be introduced through entry port 352. Suture thread 304 passes through entry nozzle 310 and then through exit nozzle 320 passing out of tip 322 of exit nozzle 320 as shown. Pressurized air is introduced through intake 334 and passes into the cavity 332 of manifold 330. The pressurized air the passes into exit nozzle 320 and is forced out of tip 322 surrounding suture thread 304. (Some air also leaks out through entry nozzle 310). The fast moving air surrounding suture thread 304 operates as an air bearing stabilizing the position of suture thread 304 adjacent tip 322 without contacting suture thread 304.

Figure 3B:
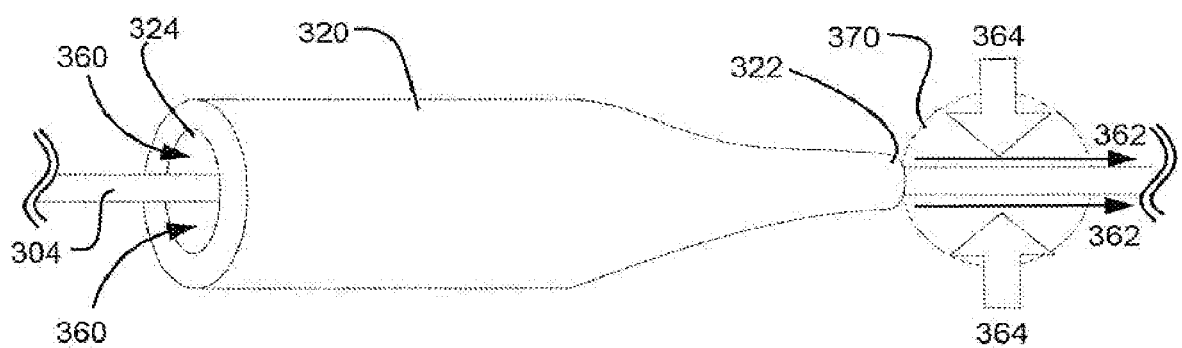
FIG. 3B shows a partial perspective view of the air bearing of FIG. 3A.

FIG. 3B, shows a perspective view only of exit nozzle 320 and suture thread 304. As shown in FIG. 3B pressurized air enters the lumen 324 of exit nozzle 320 (arrows 360 and is forced at high speed out of the narrow tip 322 of exit nozzle (arrows 362). The stream of air within tip 322 stabilizes suture thread within the center of tip 322 and so suture thread does not contact the walls of exit nozzle 320. Furthermore, a stream of high speed air surrounds suture thread 304 as it exits tip 322. The tip is designed to produce laminar flow of air in this stream in an area adjacent the tip. In this laminar flow zone, the high speed stream of air stabilizes the suture thread damping movement and vibration caused e.g. by the cutting process. Pressure is exerted by slower moving gas on the outside of the high speed stream forcing suture thread 304 to the center of stream as shown by arrows 364. Thus, the suture thread 304 is stabilized by the air bearing in the region 370 adjacent tip 322 of exit nozzle 320. The air bearing 300 is positioned so that stabilization region 370 is positioned in the cutting zone of the laser. The stream of air passing over suture thread 304 also serves to remove particulates and smoke from the laser cutting process and also cools the suture thread 304 during cutting by the laser. The suture thread is passes out of the tip 332 of exit nozzle 320 for cutting of retainers in the stabilization zone. After cutting the retainers are moved away from exit nozzle 320. It is preferred that the retainers not move into the exit nozzle as the high velocity air can damage the retainers, and the retainers can cause turbulence in the high velocity air destabilizing the suture thread in stabilization region 370.

For cutting USP 2-0 blue polypropylene suture material without an air bearing (See FIGS. 3A-3B) the following femtosecond laser parameters were found effective: a 10× objective 0.26 N.A. lens; 26 mW average laser power; 775 nm laser wavelength: (frequency doubled and mode locked erbium fiber laser with Titanium Sapphire chirped pulse amplifier; a pulse width 122 femtoseconds; an RF Divider establishing a 3 kHz pulse rate; and a cutting speed of 9.5 mm/minute. The best cutting results were achieved by penetrating the suture within the body of the filament and then moving outward to edge. For cutting USP 4-0 blue propylene suture material the following femtosecond laser parameters were found effective: a 20× objective lens, 36 mW average laser power; and a cutting speed of 10 mm/minute. With these parameters each retainer took only 1.16 second to create. Addition of an air bearing allows retainers to be created more effectively on USP 2-0, 4-0 and 6-0 blue polypropylene suture material because of e.g. stabilization of the filament and cooling of the filament during cutting. However, use of UV wavelengths was found to be more effective for cutting the blue polypropylene suture material as it vaporizes the suture material more effectively with less heating of surrounding material. In a preferred embodiment a combination of UV and IR wavelength is used to ablate material with about 70% or more of the energy being supplied in the UV wavelength.

FIG. 4A is a flowchart of a method 400 for operating the laser machining system 200 of FIG. 2A. In the first step 402, the suture thread is mounted to the chucks of the transport system. The suture thread should also be tensioned to a desired tension during the mounting step. The tension should be the same for each suture thread. At step 404, the control system operate the transport subsystem is operated to index and rotate the suture thread to the correct position for forming the first retainer. The distribution/location of retainers is stored in a retainer distribution pattern data or program file. At step 406, the control subsystem selects the correct retainer creation pattern for the indexed location on the suture thread. The retainer creation pattern dictates the final orientation, shape and size of the retainer to be created at a particular location.

The laser machining system is then operated to form a retainer at the indexed location in accordance with the selected retainer creation pattern. At step 408, the transport system is operated to align a target volume of the suture thread with the laser. At step 410, the laser subsystem is operated to ablate/cut material in the target volume. Step 410 can also include validation of the ablation/cutting using the imaging subsystem. At step 412, if further material needs to be ablated/cut to form the retainer, the process returns to step 408 to operate the transport system to align a new target volume with the laser in accordance with the retainer creation pattern. At step 412, if the laser creation pattern is completed, the process moves on to step 414.

At step 414, the imaging subsystem is operated to image the completed retainer and provide the image data to the control subsystem. The control subsystem uses the image data to validate that the retainer is within the tolerances defined by the retainer creation pattern. If the retainer cannot be validated, the control system can do one or more of: operate the transport subsystem and laser subsystem to correct the defect; fail the particular suture thread; mark an exception with respect to the suture thread for further inspection; set an alert for a human operator; and/or shut down operation of the laser-machining system. If the retainer is validated within tolerances at step 414 the process moves on to step 416. At step 416, if further retainers remain to be created, the process return to step 404 for indexing the suture thread to the next position for creating a retainer. At step 416, if all retainers have been completed, the process moves to step 418. At step 418 the suture thread is complete and is unloaded from the chucks.

Figure 4B:
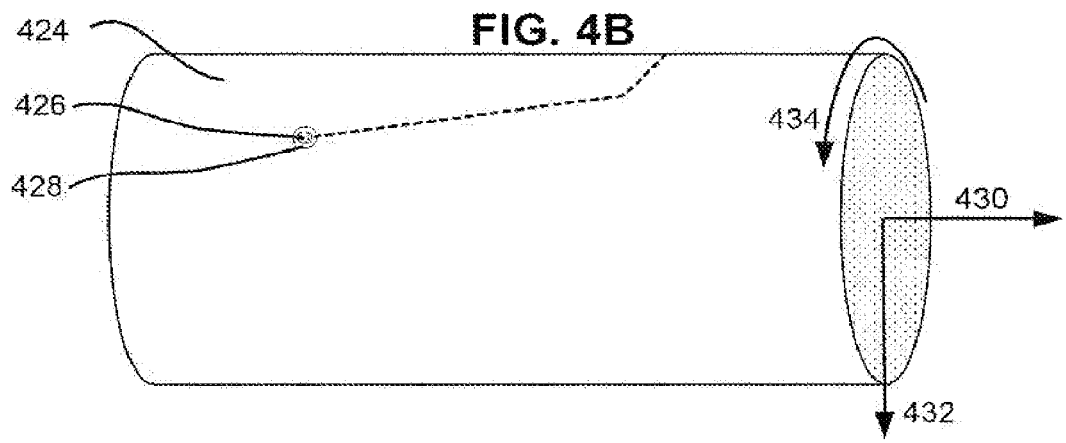
FIGS. 4B-4D are perspective views of a suture filament during the process of generating a laser-cut retainer utilizing the laser-machining system of FIG. 2A.
Figure 4C:
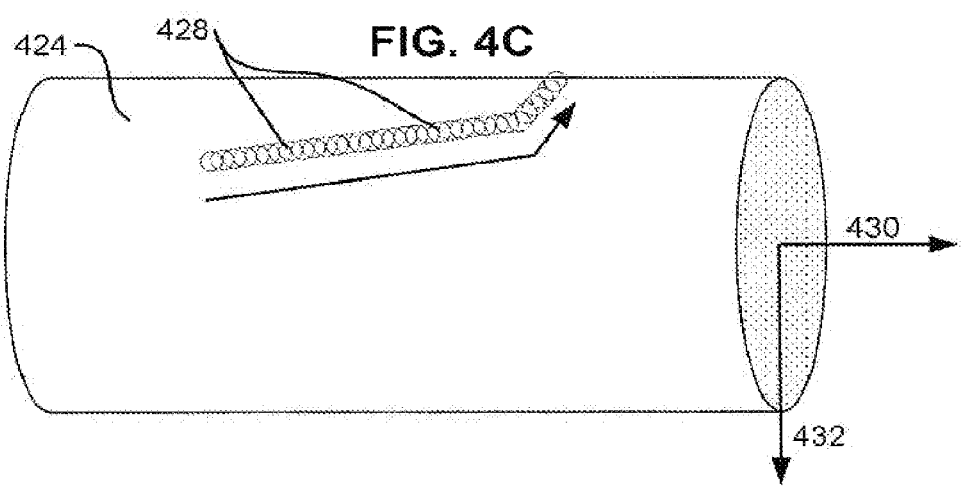
Figure 4D:
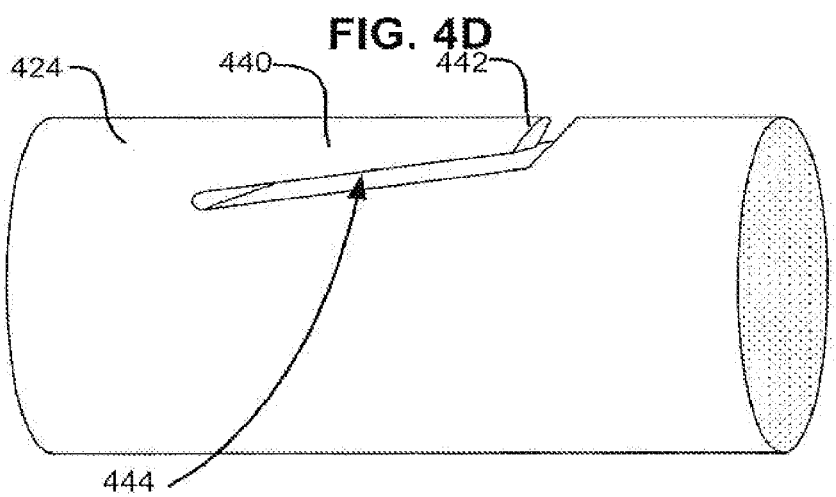

FIG. 4B-4D further illustrate steps in the process of forming a retainer according to the method of FIG. 4A. As shown in FIG. 4B, the suture thread 424 is moved longitudinally 430, laterally (432) and axially (434) by the transport subsystem to align the laser beam 426 with a target volume of the suture thread 424. The laser subsystem is then operated to ablate material from the suture thread 424, generating a cavity or slot 428. Note that cavity 428 is larger in diameter than laser beam 426. In an embodiment, a laser beam 3 μm in diameter generates a cavity of approximately 7 μm in diameter.

As shown in FIG. 4C, the suture thread 424 is moved longitudinally 430 and laterally 432 stepwise to a series of positions aligning new target volumes with the laser beam to generate a series of cavities through suture thread 424. The target volumes are dictated by the suture creation pattern. Note that it is preferable to make interior cuts to form the tissue engagement surface of the retainer prior to cutting the tip of the retainer.

FIG. 4D shows the completed retainer 440 having a tip 442 and retainer engagement surface 444. Note that tip 442 is not elevated above the surface of suture thread 424. Post-cut processing can be carried out in some cases to elevate the tip above the surface of the suture thread 424. In other embodiments, the retainer 440 is designed to be effective without elevation of the retainer tip 442 above the original surface of the suture thread 424. The same steps are repeated for the remaining retainers on suture thread 424. Note that different configurations and orientations of retainer can be created at different locations on the suture using a different retainer creation pattern without requiring a different cutting head or reloading the suture thread.

An advantage of utilizing a laser-machining system to create retainers is the ability to form retainers in configurations that are difficult and/or impossible to make using mechanical cutting with a blade. FIGS. 5A-5D show examples of retainer configurations which can be created with a laser-machining system according to embodiments of the present invention. FIGS. 5A-5D illustrate capabilities of the laser-machining system of the present invention and examples of features of retainers which can be created. These features can be used in any desired combination.

Figure 5A:
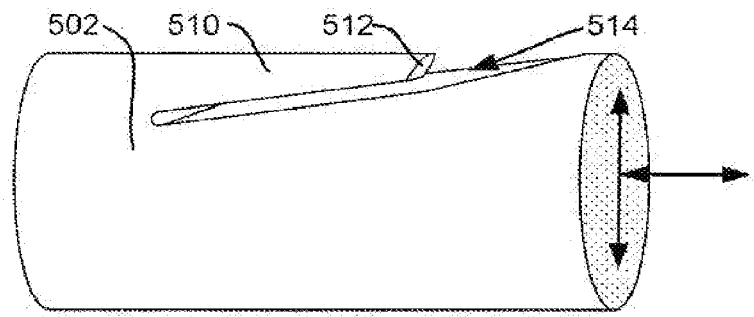
FIGS. 5A-5H show alternative laser-cut retainer configurations that can be created utilizing the laser-machining system of FIG. 2A according to embodiments of the present invention.

FIG. 5A shows a retainer 510. Note that additional material has been removed ahead of tip 512 of retainer 510 to form an entrance ramp 514. Entrance ramp 514 allows tip 512 to engage tissue during deployment without elevation of tip 512 above the original surface of suture thread 502. One advantage of the laser-machining system of the present invention is the ability to remove suture material in sculpting a retainer rather than merely cutting the material.

Figure 5B:
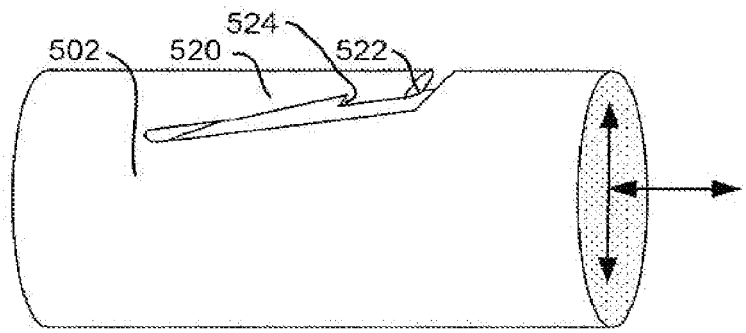

FIG. 5B shows a retainer 520 having a tip 522. Note that additional material has been removed from the inside surface of retainer 520 to create a secondary retainer 524 in the form of a ridge oriented towards the base of the retainer 520. Secondary retainer 524 serves to enhance tissue engagement by retainer 520. One advantage of the laser-machining system of the present invention is the ability to remove suture material in sculpting a retainer and also changing the angle or direction of a cut surface without the need for multiple mechanical cutting steps with a blade.

Figure 5C:
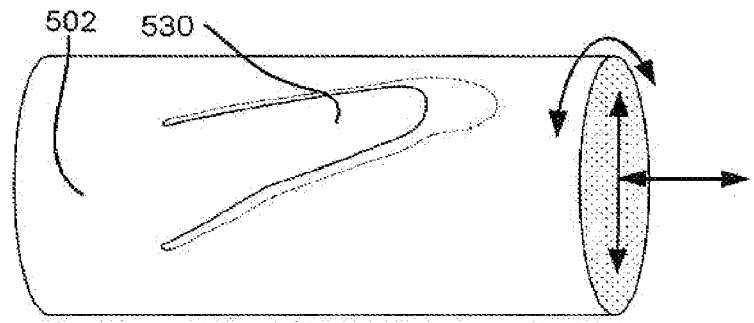

FIG. 5C shows a retainer 530 similar in configuration to retainer 510 of FIG. 5A. However, during the creation of retainer 530 suture thread 502 is moved axially as well as longitudinally and laterally. The resulting retainer 530 curves around suture thread 502 at an angle to the longitudinal axis of suture thread 502. Any combination of longitudinal, lateral and axial movement necessary for creation of a desired retainer can be achieved with the laser-machining system of the present invention without limitations imposed by mechanical cutting mechanisms.

Figure 5D:
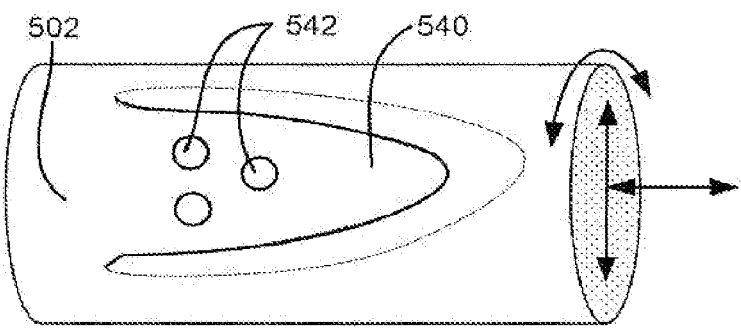

FIG. 5D shows a retainer 540 similar in configuration to retainer 510 of FIG. 5A. However, the laser-machining system has been operated to make one or more apertures 542 in retainer 540. Apertures 542 can, in some embodiments, pass from the exterior surface of retainer 540 through to the tissue engagement surface (not shown) of retainer 540; during the creation of retainer 540, suture thread 502 is moved axially as well as longitudinally and laterally. Apertures 542 need not (and preferably do not) pass all the way through suture thread 502. Apertures 542 (or other features removing material) can be used to modulate the flexibility/strength of the retainer, encourage tissue in-growth; and/or enhance tissue engagement by the retainer.

Figure 5E:
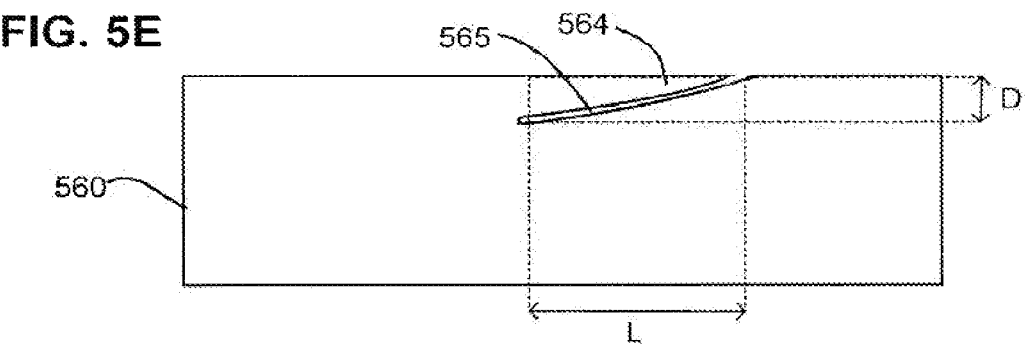
Figure 5F:
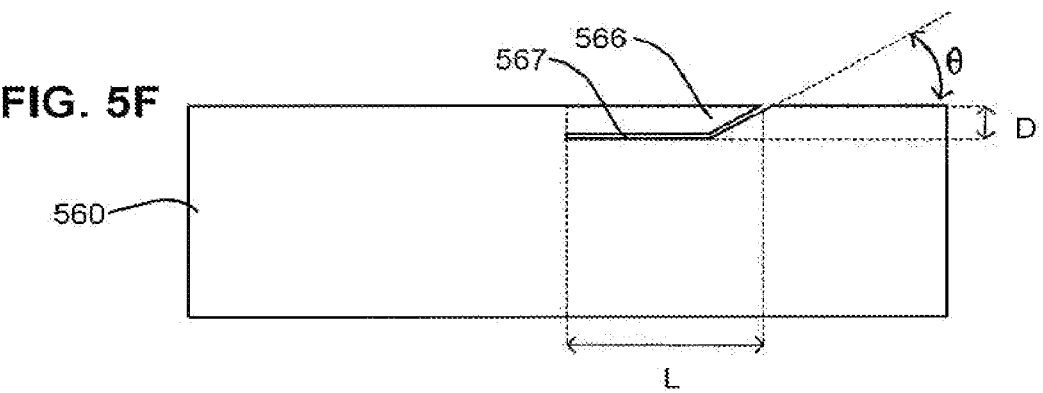

FIGS. 5E-5H show a range of additional retainer designs. For each retainer, a USP 4-0 suture filament 560 is used. FIG. 5E shows a parabolic retainer 564. The depth of cut D (measured transversely) is 60 µm. The length of cut L (measured axially) is 250 µm. The width of the kerf 565 (the channel of material removed by the laser) is 7 µm. FIG. 5F shows an alternative retainer 566 having a 30 degree tip slope and then a retainer face which is cut substantially parallel to the longitudinal axis of the suture. The depth of cut D (measured transversely) is 0.036 mm. The length of cut L (measured axially) is 0.234 mm although the length can be any desired length limited only by the functional requirements of the retainer. The angle of entry θ is 30 degrees from the suture axis. Once again, the width of the kerf 567 (the channel of material removed by the laser) is 7 µm.

Figure 5G:
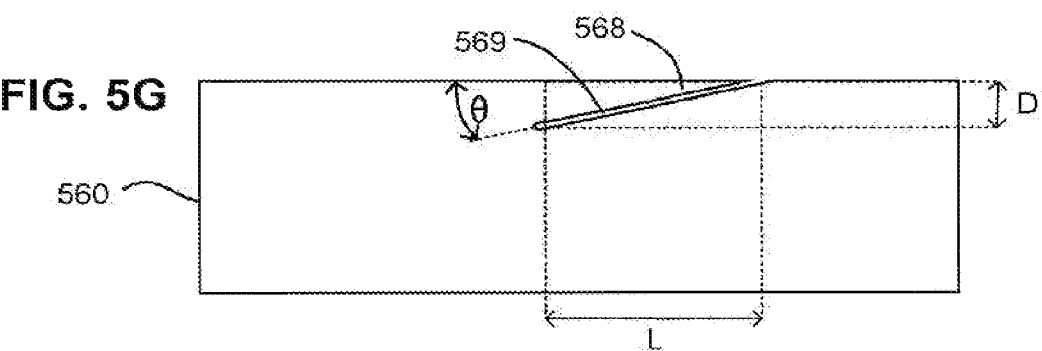
Figure 5H:
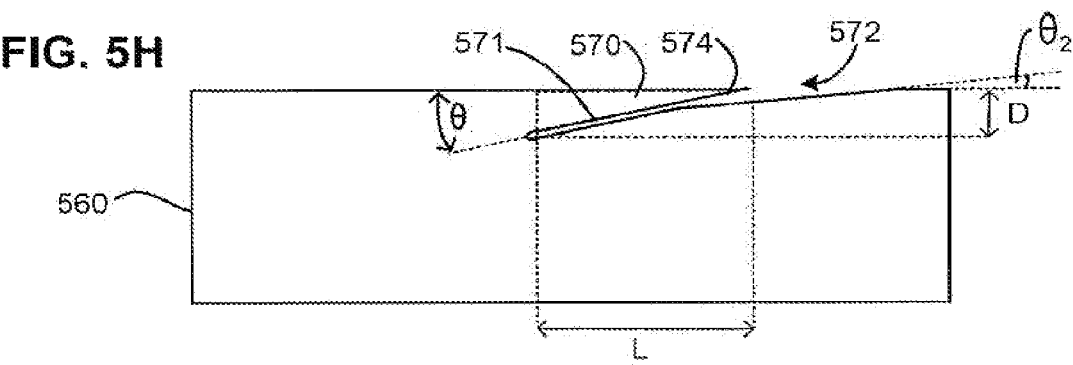

FIG. 5G shows a straight-cut retainer 568. The depth of cut D (measured transversely) is 60 µm. The length of cut L (measured axially) is 250 µm. The angle θ of the cut is 13 degrees from the suture axis. The width of the kerf 569 (the channel of material removed by the laser) is again 7 µm. FIG. 5H shows a straight-cut retainer 570 preceded by an entrance ramp 572. The depth of cut D (measured transversely) is 60 µm. The length of cut L (measured axially) is 250 µm. The angle of the cut θ of retainer 570 is 13 degrees from the suture axis. The angle of cut $\theta_2$ of entrance ramp is 6 degrees from the suture axis. The width of the kerf 571 (the channel of material removed by the laser) is again 7 µm, however, additional material is removed from entrance ramp 572 due to the difference between θ and $\theta_2$. Entrance ramp 572 serves to expose the tip 574 of retainer 570 allowing retainer 570 to engage tissue without being elevated above the original surface of suture filament 560.

The above described retainer configurations can be scaled down in size for smaller suture diameters. Similarly, for smaller diameter sutures, the kerf width can be reduced by, for example, adjusting the power, pulse width and focus of the laser beam. For example, for a 6-0 suture a kerf width of 51 Am is preferred, whereas for a 2-0 suture a kerf width of 101.im is preferred. Also many alternative retainer designs can be made using the laser machining system of the present invention including for example alternative retainer shapes disclosed in U.S. patent application Ser. No. 12/101,885 titled "Self-Retaining Systems For Surgical Procedures" filed Apr. 11, 2008, issued as U.S. Pat. No. 8,793,863 on Aug. 5, 2014, which is incorporated herein by reference.

With some laser-cut retainer configurations it is desirable and/or necessary to elevate the tip of the retainer above the surface of the suture filament in order to place the retainer in a configurations suitable for engaging tissue. The retainers can be elevated by one or more of heating the suture filament and/or placing the suture filament under tension. Once elevated an annealing step can be performed to maintain the retainers in an elevated configuration. For example, placing a suture filament under 10 grams.6 grams of tension at 156 C is one protocol that can be utilized to elevate retainers on a suture filament.

Figure 6A:
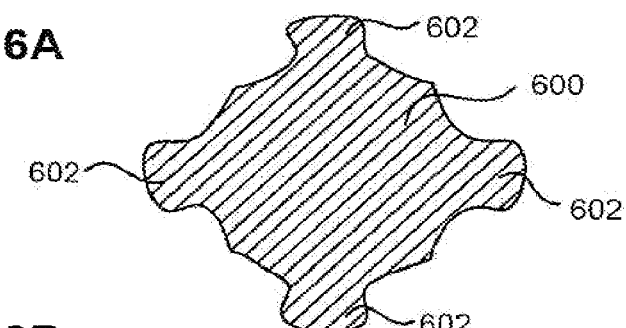
FIGS. 6A-6C are a sectional view, perspective view and an image of a filament having laser cut retainers thereon formed by an alternative material subtraction method of utilizing the laser-machining system of FIG. 2A according to an embodiment of the present invention.
Figure 6B:
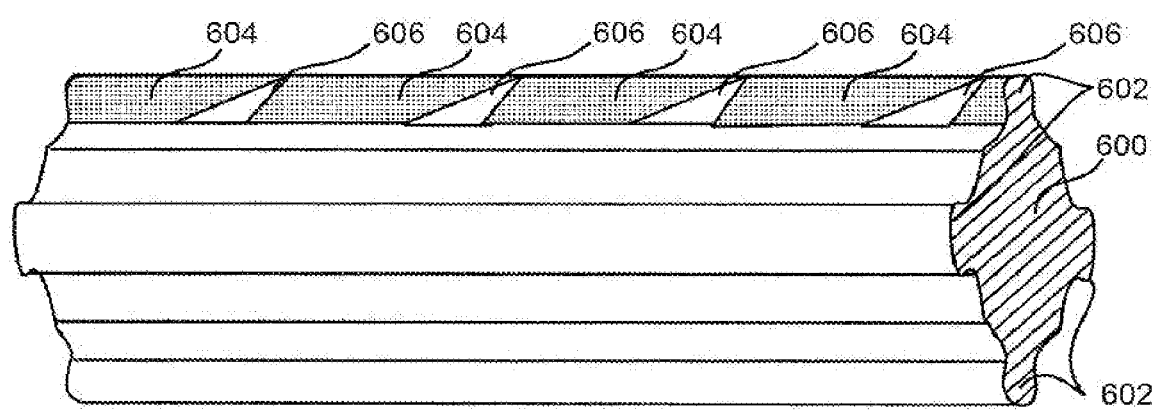
Figure 6C:
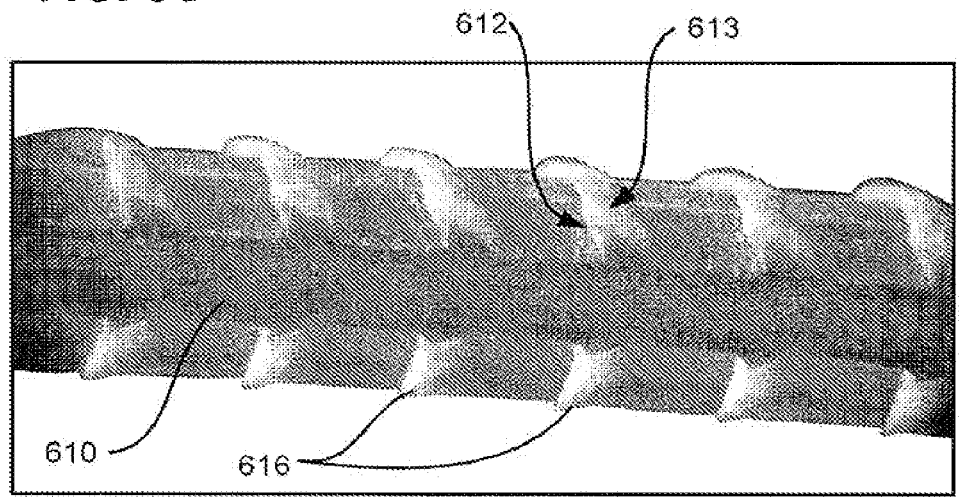

FIGS. 6A through 6C illustrate a somewhat different method for making retainers on the surface of a filament 600. FIG. 6A shows a cross-section of a filament 600. As shown in FIG. 6A, filament 600 has a plurality of ridges 602 protruding from filament 600. Filament 600 is in one embodiment extruded with the cross-section shown in FIG. 6A. However, the shape of filament 600 can be achieved in a number of ways. See, for example, U.S. patent application Ser. No. 12/392,939 titled "Alternate Geometry Self-retaining Suture" to Goraltchouk et al.; and U.S. patent application Ser. No. 12/340,444 titled "Composite Self-Retaining Sutures" to Goraltchouk et al., issued as U.S. Pat. No. 8,916,077 on Dec. 23, 2014, which references are incorporated herein by reference.

FIG. 6B is a perspective drawing of filament 600. Portions of the upper ridge 602 are shaded. The shaded regions of ridge 602 are targeted with the laser beam and removed. Removal of the shaded region 604 leaves a plurality of retainers on 606 on the surface of filament 600. Because the retainers 606 are formed by the removal of surrounding material 604, the retainers are created in a configuration protruding from the laser-cut surface and advantageously positioned for engaging tissue without need for any post-processing. Retainers may be similarly formed on the other ridges 602 of filament 600 to create a barbed filament.

FIG. 6C is an image of a barbed filament created using the subtraction process described with respect to FIG. 6B. To create the barbed filament shown in FIG. 6C, a 775 nm femtosecond laser was used at a power output of 0.87 watts. The highest features of the filament were removed leaving the retainers 616 shown protruding from the surface of the filament 610. Retainers 616 were thus created by ablating the surrounding material from filament 610 with a laser beam. As can be seen from FIG. 6C, the retainers 616 are proud of the final surface of filament 610 and do not require elevation or other post processing in order to engage tissue.

In the embodiment shown in FIG. 6C each retainer has a laser-cut inner surface 612 and a laser cut outer surface 613. The shape of each of laser-cut inner surface 612 and a laser cut outer surface 613 can be selected as desired for the function of the retainer 616. Thus retainers 616 can be created in a wide range of shapes, sizes and configurations, including, for example those retainer configurations disclosed in U.S. patent application Ser. No. 12/101,885 entitled "Self-Retaining Systems For Surgical Procedures" to Hunter et al., issued as U.S. Pat. No. 8,793,863 on Aug. 5, 2014 which is incorporated herein by reference in its entirety. Furthermore, because each retainer is created individually by the laser machining system a self-retaining suture can be created having retainers of a plurality different shapes, sizes and configurations and orientations on a single filament.

Figure 6D:
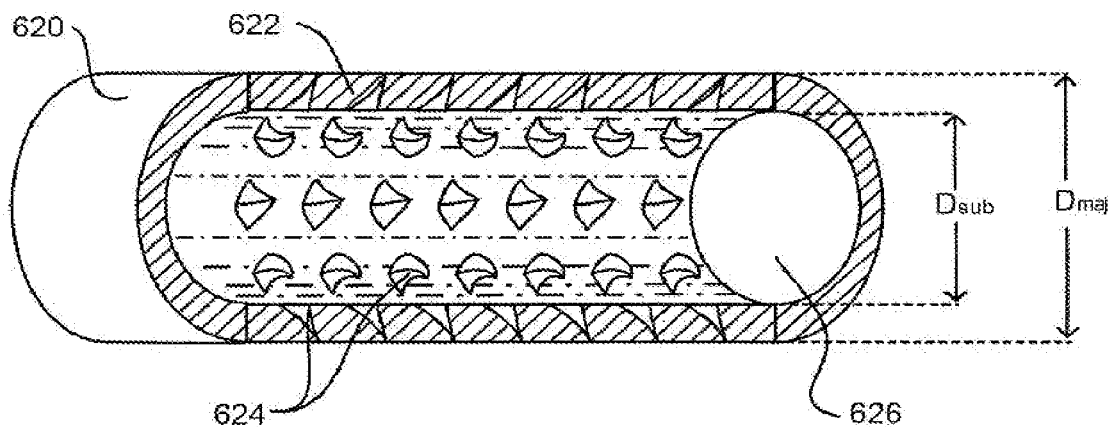
FIG. 6D is a partial cutaway view of an alternative design for a self-retaining suture utilizing the material subtraction design described with respect to FIGS. 6A-6C.

FIG. 6D shows a partial cutaway drawing of a suture filament having a plurality of laser-cut retainers formed thereon by removal of material surrounding the retainers. As shown in FIG. 6D, a filament 620 has an initial diameter $D_{maj}$. A laser machining system is used to remove material from the surface (see shaded regions 622) of filament 620 until it has a reduced diameter of $D_{sub}$. However, during the removal of the material by the laser, the laser is controlled to avoid removing the material in the shape of a plurality of retainers 624. Thus, after removal of material by the laser machining system a suture filament 626 remains of diameter $D_{sub}$ and having a plurality of retainers 624 arrayed on its surface. In one embodiment, filament 620 is a 6-0 polypropylene suture.

Figure 6E:
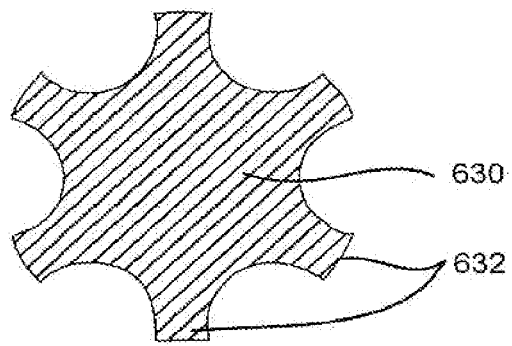
FIGS. 6E and 6F are sectional and perspective views of an alternative design for a self-retaining suture utilizing the material subtraction design described with respect to FIGS. 6A-6C.
Figure 6F:
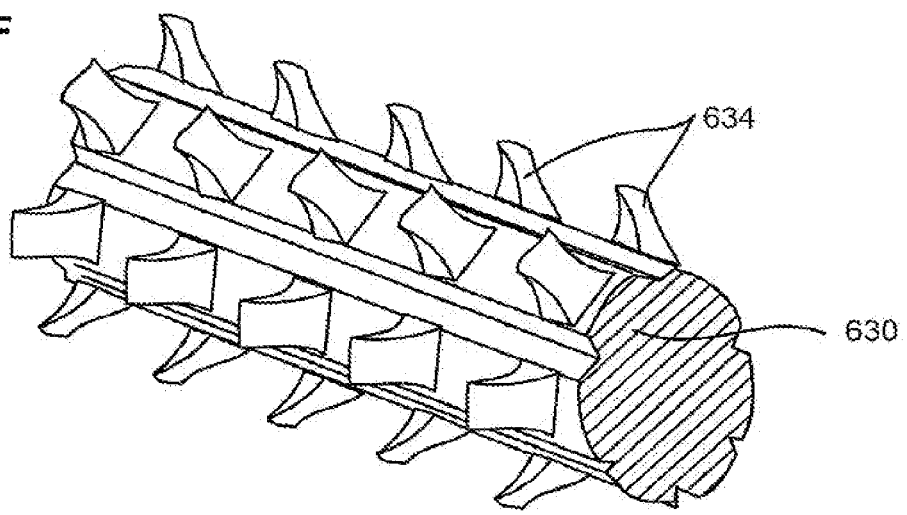

FIGS. 6E and 6F show sectional and perspective views of another alternative suture filament having a plurality of laser-cut retainers formed thereon by removal of material surrounding the retainers. FIG. 6E shows a sectional view of the stock suture filament 630. As shown in FIG. 6E, suture filament 630 has six ridges 632 spaced 60 degrees from one another around the circumference of filament 630. As previously discussed with respect to FIGS. 6A-6C, a laser-machining system is used to remove material from ridges 632 leaving retainers 634 on the surface of filament 630 as shown in FIG. 6F. Utilized a shaped laser beam coming from a compound angle the retainers 634 shaped as shown in FIG. 6F can be formed without clipping other retainers during removal of the material of ridges 632. Compound angle refers to the incidence of the laser beam from an angle other than perpendicular to the longitudinal axis of the suture. Shaped laser beam refers, for example to a conical laser beam formed with e.g. an axicon-based optic system.

Figure 7A:
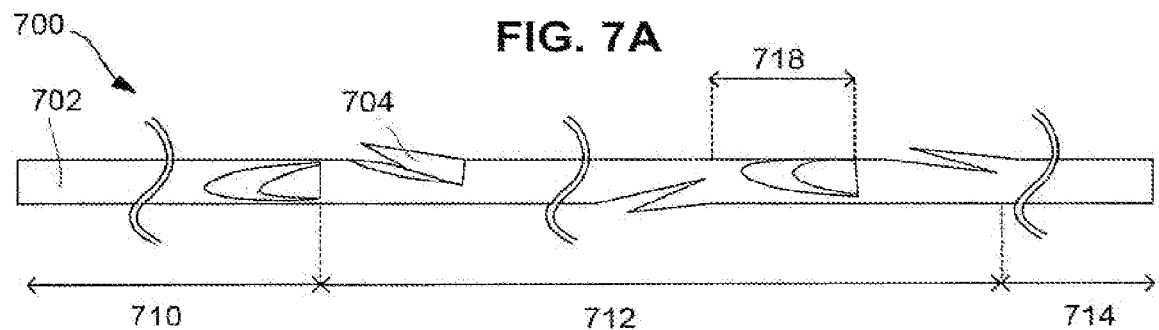
FIGS. 7A-7C show retainer distribution configurations for self-retaining sutures made utilizing the laser-machining system of FIG. 2A according to embodiments of the present invention.
Figure 7B:
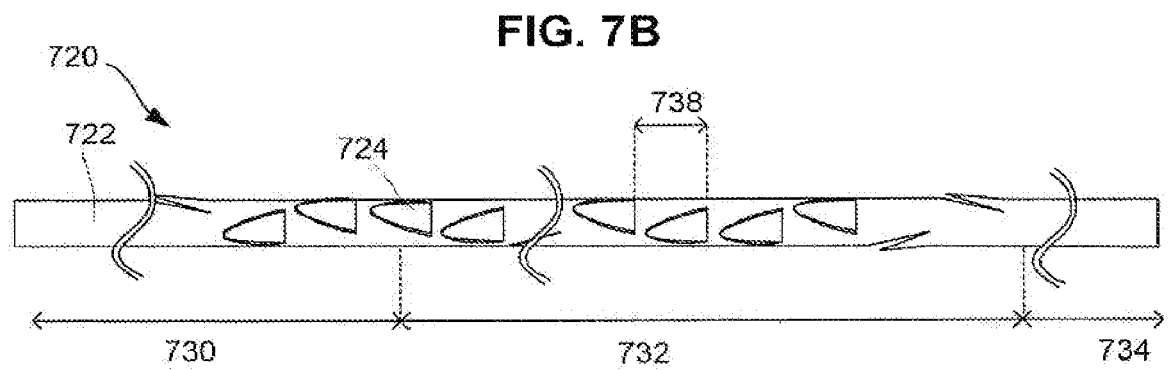
Figure 7C:
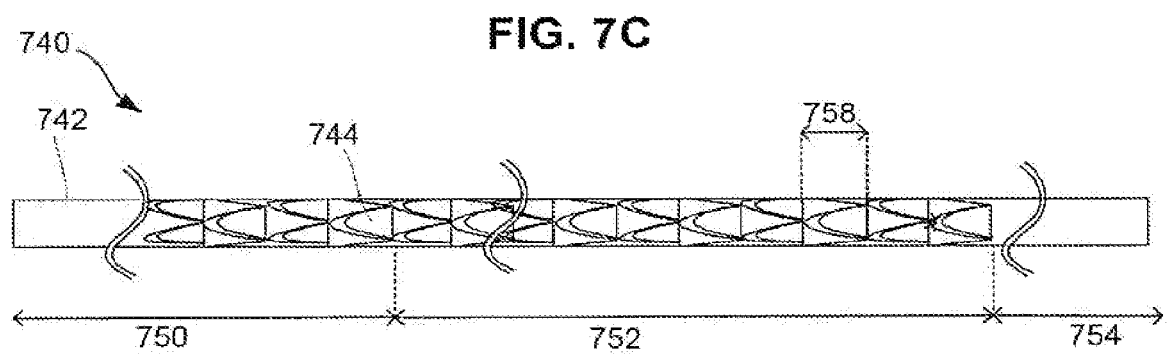

FIGS. 7A, 7B, and 7C show a range of retainer distributions and patterns that can be created using the laser machining system. For example, FIG. 7A shows a single helix distribution of laser-cut retainers on a self-retaining suture according to an embodiment of the invention; FIG. 7B shows a double helix distribution of laser-cut retainers on a drug-eluting self-retaining suture according to an embodiment of the invention; FIG. 7C show a high density distribution of laser-cut retainers on a self-retaining suture according to an embodiment of the invention. The laser-cut retainers can have any laser-cut retainer configuration described herein and/or different laser-cut retainer configurations can be present at different points of the self-retaining suture. Note also that the laser machining system of the present invention is capable of creating non-uniform retainer distributions along a single suture thread if advantageous for a particular self-retaining suture application.

Referring first to FIG. 7A which shows a single helix distribution of laser-cut retainers 704 on a self-retaining suture 700. As shown in FIG. 7A, the self-retaining suture 700 has a filament 702 which is of USP 2-0, 4-0, 6-0, 7-0, 8-0, 9-0, 10-0, 11-0, 12-0 or below. As shown in FIG. 7A, the filament is 0.25 mm in diameter which is a 4-0 suture. The self-retaining suture 700 includes a plurality of laser-cut retainers 704 arranged in a helical pattern around and along the filament 702. As shown in FIG. 7A, the helix has a pitch of 4.46 mm (or 5.7 twists per inch). The distance between the base of one laser-cut retainer and the base of the adjacent laser-cut retainer in the same helix is 0.6 mm—measured axially—see arrow 718. In an embodiment, the self-retaining suture has a barbed section 712 at least 70 mm in length and a 100 mm unbarbed lead 710, 714 on either side of the barbed section 712. The barbed section 712 may have retainers 704 in one orientation or in different orientations. Note that because the laser machining system is contactless, retainer distribution patterns can be designed without limitations imposed by the need to support a suture without impairing already cut retainers during mechanical cutting. Thus, for example, in some embodiments, the pitch can be less than the length of a retainer.

Referring now to FIG. 7B which shows a double helix distribution of laser-cut retainers 724 on a self-retaining suture 720. As shown in FIG. 7B, the self-retaining suture 720 has a filament 722 which is of USP 2-0, 4-0, 6-0, 7-0, 8-0, 9-0, 10-0, 11-0, 12-0 or below. As shown in FIG. 7B, the filament is 0.25 mm in diameter which is a 4-0 suture. The self-retaining suture 720 includes a plurality of laser-cut retainers 724 arranged in a double helical pattern around and along the filament 722. As shown in FIG. 7B, each helix has a pitch of 7 mm (or 4.2 twists per inch). The helixes are shifted axially by 0.49 mm relative to one another. The distance between the base of one laser-cut retainer and the base of the adjacent laser-cut retainer in the same helix 1 mm—measured axially—see arrow 738. In an embodiment, the self-retaining suture has a barbed section 732 at least 100 mm in length and a 100 mm unbarbed lead 730, 734 on either side of the barbed section 732. The barbed section 732 may have retainers 724 in one orientation or in different orientations. Note that because the laser machining system is contactless, retainer distribution patterns can be designed without limitations imposed by the need to support a suture without impairing already cut retainers during mechanical cutting. Thus, for example, in some embodiments the pitch can be less than the length of a retainer.

Referring now to FIG. 7C which shows a high density distribution of laser-cut retainers 744 on a self-retaining suture 740. As shown in FIG. 7C, the self-retaining suture 740 has a filament 742 which is of USP 7-0, 7-0, 8-0, 9-0, 10-0, 11-0, 12-0 or below. As shown in FIG. 7C, the filament is 0.25 mm in diameter which is a 4-0 suture. The self-retaining suture 740 includes a plurality of laser-cut retainers 744 arranged in groups of four retainers each arranged at 90 degrees spacing. Each adjacent set of four laser-cut retainers is offset to the adjacent sets by 45 degrees. Each retainer is 0.18 mm from tip of depression to base of cut—measured axially—see arrow 758. The distance between the base of the laser-cut retainer in one set and the base of the adjacent laser-cut retainers is 0.28 mm—measured axially—see arrow 758. In an embodiment the self-retaining suture has a barbed section 752 at least 70 mm in length and a 100 mm unbarbed lead 750, 754 on either side of the barbed section 752. The barbed section 752 may have laser-cut retainers 744 in one orientation or in different orientations. Note that because the laser machining system is contactless, retainer distribution patterns can be designed without limitations imposed by the need to support a suture without impairing already cut retainers during mechanical cutting. Thus, for example, in alternative embodiments each group can include five, six or more retainers and/or the pitch can be less than the length of a retainer so long as the retainers do not interfere.

Examples of Self-Retaining Sutures with Laser-Cut Retainers

FIGS. 8A-8J are images of examples of self-retaining sutures comprising suture threads with a plurality of laser-cut retainers thereon made to test the capabilities of a laser-machining system in accordance with FIG. 2A. The suture threads were, in each case blue-colored propylene filaments.

Figure 8A:
FIGS. 8A-8F show examples of self-retaining sutures made utilizing the laser-machining system of FIG. 2A according to embodiments of the present invention.

FIG. 8A shows an image of 2-0 polypropylene suture 810 having laser-cut retainers 812 thereon. Laser-cut retainers 812 have a straight cut configuration and are distributed in a high density quadra-helix distribution. After the retainers 812 were cut, the suture 810 was heat treated for five minutes at 155 C to elevate the retainers 812.

Figure 8B:
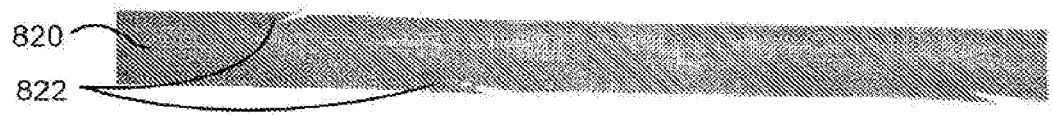

FIG. 8B shows an image of 2-0 polypropylene suture 820 having laser-cut retainers 822 thereon. Laser-cut retainers 822 have a straight cut configuration and are distributed in a double-helix distribution. After the retainers 822 were cut, the suture 820 was heat treated for five minutes at 155 C while under 32 grams of tension to elevate the retainers 822.

Figure 8C:
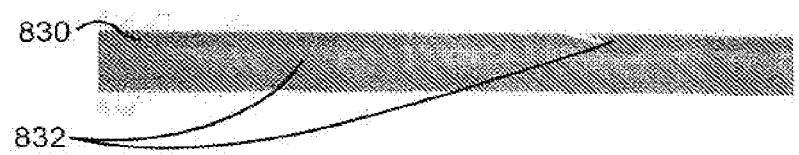

FIG. 8C shows an image of 2-0 polypropylene suture 830 having laser-cut retainers 832 thereon. Laser-cut retainers 832 have a straight cut configuration and are distributed in a double-helix distribution. After the retainers 832 were cut, the suture 830 was heat treated for five minutes at 155 C without tension to elevate the retainers 832.

Figure 8D:
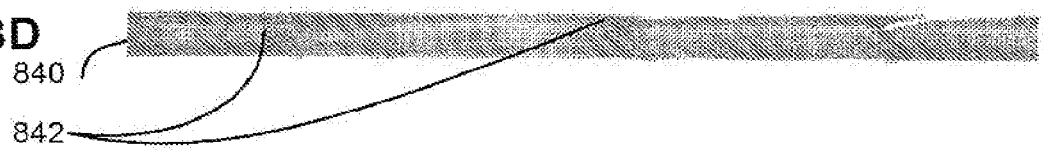

FIG. 8D shows an image of 6-0 polypropylene suture 840 having laser-cut retainers 842 thereon. Laser-cut retainers 842 have an entrance-ramp configuration and are distributed in a double-helix distribution.

Figure 8E:

FIG. 8E shows an image of 6-0 polypropylene suture 850 having laser-cut retainers 852 thereon. Laser-cut retainers 852 have a straight cut configuration and are distributed in a double-helix distribution. After the retainers 852 were cut, the suture 850 was heat treated for five minutes at 155 C while under 10.6 grams of tension to elevate the retainers 852.

Figure 8F:
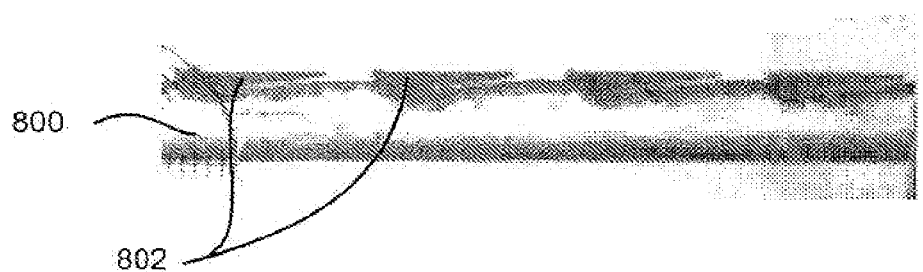

FIG. 8F shows an image of 10-0 polypropylene suture 800 having laser-cut retainers 802 thereon. Laser-cut retainers 852 have a straight cut configuration.

Figure 8G:
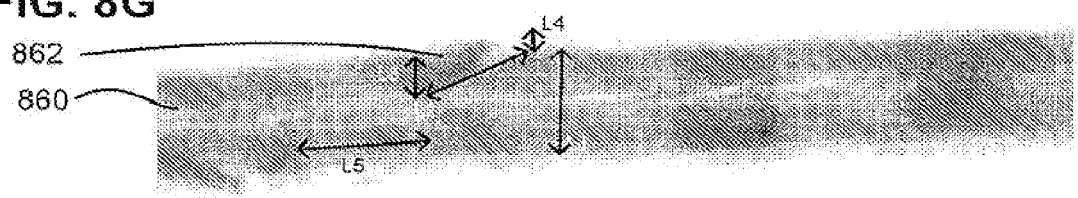
FIGS. 8G-8J show examples of self-retaining sutures made utilizing the laser-machining system of FIG. 2A and measurements of the self-retaining sutures according to embodiments of the present invention.

FIG. 8G shows an image of a polypropylene suture 860 having laser-cut retainers 862 thereon. Laser-cut retainers 862 have a straight cut configuration and are distributed in a double-helix distribution. After the retainers 862 were cut, the suture 860 was heat treated for five minutes at 155 C to elevate the retainers 862. The resulting parameters L1-L5 of suture 860 were then measured under a microscope. The suture diameter L1 was 101.8 µm; the cut length L2 was 99.5 µm; the cut depth L3 was 34.5 µm; the elevation L4 of the tip of the retainer above the surface of the filament was 15.8 µm; and the distance L5 between adjacent retainers was 118.3 µm.

Figure 8H:
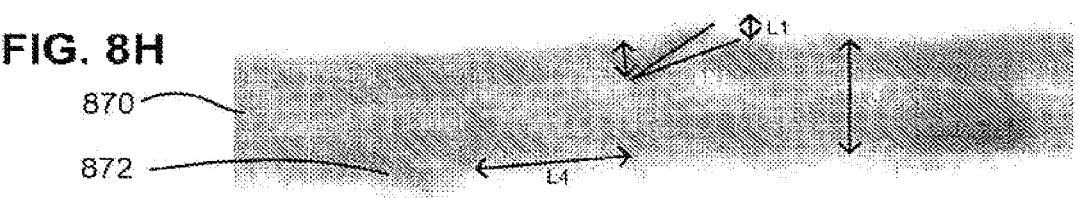

FIG. 8H shows an image of a polypropylene suture 870 having laser-cut retainers 872 thereon. Laser-cut retainers 872 have a straight cut configuration and are distributed in a double-helix distribution. After the retainers 872 were cut, the suture 870 was heat treated for five minutes at 155 C to elevate the retainers 872. The resulting parameters L1-L4 and AN1 of suture 870 were then measured under a microscope. The suture diameter L3 was 103.8 µm; the cut depth L2 was 29.7 µm; the elevation L1 of the tip of the retainer above the surface of the filament was 14.6 µm; the distance L4 between adjacent retainers was 131.3 µm; and the angle AN1 was 14.3 degrees.

Figure 8I:
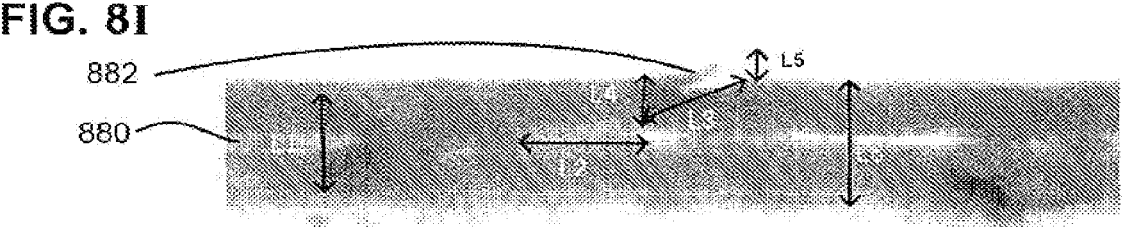

FIG. 8I shows an image of a polypropylene suture 880 having laser-cut retainers 882 thereon. Laser-cut retainers 882 have a straight cut configuration and are distributed in a double-helix distribution. After the retainers 882 were cut, the suture 880 was heat treated for five minutes at 155 C to elevate the retainers 882. The resulting parameters L1-L6 of suture 880 were then measured under a microscope. The suture diameter L6 was 93.3 µm; the width L1 of the retainer base was 77.6 µm; the cut length L3 was 69.2 µm; the cut depth L4 was 28.5 µm; the elevation L5 of the tip of the retainer above the surface of the filament was 14.6 µm; and the distance L2 between adjacent retainers was 89.1 µm.

Figure 8J:
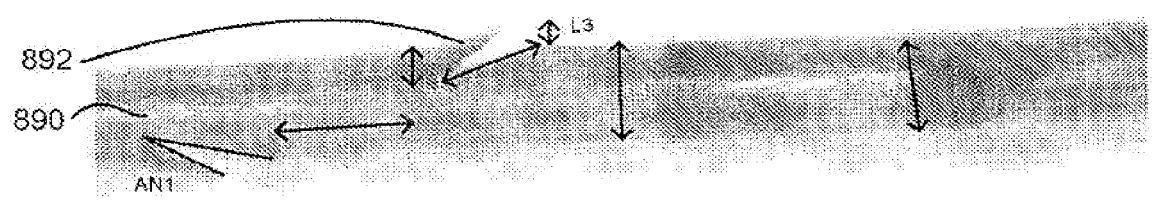

FIG. 8J shows an image of a polypropylene suture 890 having laser-cut retainers 892 thereon. Laser-cut retainers 892 have a straight cut configuration and are distributed in a double-helix distribution. After the retainers 892 were cut, the suture 890 was heat treated for five minutes at 155 C to elevate the retainers 892. The resulting parameters L1-L6 and AN1 of suture 890 were then measured under a microscope. The suture diameter L5 was 96.5 µm; the width L6 of the retainer base was 83.4 µm; the cut length L1 was 107.9 µm; the cut depth L2 was 37.0 µm; the elevation L3 of the tip of the retainer above the surface of the filament was 21.2 µm; the distance L4 between adjacent retainers was 117.2 µm; and angle An1 was 18 degrees.

Samples of laser-cut self-retaining suture prototypes were mechanically tested for holding strength and tensile strength as compared to mechanically cut quadrahelix self-retaining suture and plain USP 6-0 suture. The results were based on testing 10 samples of each suture FIG. 9A is a table showing the results of the mechanical testing.

A laser-cut surface of a self-retaining suture was examined for flatness and uniformity. A retainer was removed to allow image of the underlying laser-cut surface of the filament. The laser-cut tissue engagement surface of the retainer (not shown) should have similar characteristics of flatness and uniformity. FIG. 9B shows an image of the examined laser cut surface 922 machined into a suture thread 920. FIG. 9C shows a graph of the profile of laser-cut surface viewed laterally.

Indicia for Enhancing Utility of Self-Retaining Suture Having Laser-Cut Retainers As discussed above, it is useful to mark and identify portions of a self-retaining suture system where different sections of the suture have different features such as in bidirectional self-retaining suture systems. In self-retaining suture systems, the difference in function between sections of the suture may be the presence, absence and/or orientation of retainers. In one aspect it may be desirable to mark the transition section of a bidirectional suture. In one embodiment of the present invention, the laser-machining system 200 of FIG. 2A can also be operated to create laser-marked indicia which are readily recognized and distinguished by the physician under the conditions in which the suture is to be used thereby allowing the surgeon to locate the transition region and/or other section of the self-retaining suture.

When creating indicia, the laser subsystem is controlled to supply a modified laser beam suitable for denaturing, bleaching, and/or discoloring a colorant or other component of the suture thread without significant ablation, cutting and/or weakening of the suture thread. As the laser-marked indicia of a self-retaining or ordinary suture should be located appropriately to identify particular sections/features of the self-retaining suture, it is important that the laser-marking system be configured to align the laser marking head with the appropriate locations of the suture. This can be readily achieved by using the same system to create the retainers and laser-marked indicia. The laser-machining system can create laser-marked indicia as part of the same program which indexes the suture and create retainers thereon.

In alternative embodiments, the indicia, laser-marked or otherwise, are created on the suture thread in a process prior to loading the suture thread on the laser-machining system 200 of FIG. 2. After the suture thread is loaded in laser-machining system 200, the imaging subsystem 230 is used to identify the position of the indicia and provide the location of the information to the control subsystem 250. The control subsystem 250 then controls transport subsystem 240 to index the suture thread such the retainers are formed in the correct relationship to the detected indicia. For example, the suture thread may be a suture half one color and half another color. When loaded in the retainer-forming machine the imaging subsystem 230 is used to locate the boundary between the two colors. The transport subsystem 240 and laser subsystem 210 and optic subsystem are then operated to create retainers at positions relative to the boundary such that the transition section of the self-retaining suture is located at the boundary. This alternate process is useful, for example, where the indicia creating process is incompatible with integration into the laser-machining system 200 or is more efficiently utilized off-line from the retainer creation process.

To facilitate creation of indicia, the suture thread is provided with a colorant which changes color in response to e.g. laser exposure. Colorants include both dyes (water soluble) and pigments (not water soluble). Preferred colorants are non-reactive and biologically inert. Colorants are available in a variety of colors including black and white. In addition, colorants include dyes and pigments which can be visualized using alternate sources of energy such as using a "black light" which makes the colorant fluoresce or otherwise become visible. Suitable colorants, marking techniques and indicia are disclosed in U.S. Provisional Patent Applications 61/290,750 and 61/296,721 titled "Bidirectional Self-Retaining Sutures With Laser-Marked And/Or Non-Laser Marked Indicia And Methods" to Gross et al. which is incorporated herein by reference. The suture colorant is selected for its ability to change color in response to laser exposure that does not damage the suture thread. In preferred embodiments treatment of the suture with laser causes a color change in the treated region(s) which has high contrast with the untreated region(s) in order to enhance the visibility of the laser-marked indicia. The change in color is, in particular embodiments, from colored to uncolored, from uncolored to colored, from a first color to a second color different than the first color, and/or from a color at a first density to the same color at a different density.

Materials

Suture threads described herein may be produced by any suitable method, including without limitation, injection molding, stamping, cutting, laser, extrusion, and so forth. The suture threads described herein may use any material conventionally used for the manufacture of sutures including for example, non-degradable polymers, biodegradable polymers and natural materials. With respect to cutting, polymeric suture threads/filaments may be manufactured or purchased for the suture body, and the retainers can be subsequently cut onto the suture body. During cutting, either the laser beam or the suture thread may be moved relative to the other, or both may be moved, to control the size, shape and depth of the retainers.

It is an advantage of the laser-machining system described herein that it is operative to form retainers on a wide range of suture materials. Suitable suture materials include: degradable suture materials, non-degradable suture materials, natural suture materials, recombinant suture materials and metallic suture materials. Degradable suture materials (also referred to as "biodegradable suture" or "absorbable suture") are those which, after introduction into a tissue are broken down and absorbed by the body. Typically, the degradation process is at least partially mediated by, or performed in, a biological system. "Degradation" refers to a chain scission process by which a polymer chain is cleaved into oligomers and monomers. Chain scission may occur through various mechanisms, including, for example, by chemical reaction (e.g., hydrolysis, oxidation/reduction, enzymatic mechanisms or a combination of these) or by a thermal or photolytic process. Polymer degradation is, in some embodiments, characterized, for example, using gel permeation chromatography (GPC), which monitors the polymer molecular mass changes during erosion and breakdown. Non-degradable suture materials (also referred to as "non-absorbable suture") are those which are not degraded by chain scission such as chemical reaction processes (e.g., hydrolysis, oxidation/reduction, enzymatic mechanisms or a combination of these) or by a thermal or photolytic process.

Degradable suture materials include polymers for example polyglycolic acid, copolymers of glycolide and lactide, copolymers of trimethylene carbonate and glycolide with diethylene glycol (e.g., MAXON™, Tyco Healthcare Group), terpolymer composed of glycolide, trimethylene carbonate, and dioxanone (e.g., BIOSYN™ [glycolide (60%), trimethylene carbonate (26%), and dioxanone (14%)], Tyco Healthcare Group), copolymers of glycolide, caprolactone, trimethylene carbonate, and lactide (e.g., CAPROSYN™, Tyco Healthcare Group). A dissolvable suture can also include partially deacetylated polyvinyl alcohol. Polymers suitable for use in degradable sutures can be linear polymers, branched polymers or multi-axial polymers. Examples of multi-axial polymers used in sutures are described in U.S. Patent Application Publication Nos. 2002/0161168, now abandoned, 2004/0024169, issued as U.S. Pat. No. 7,026,437 on Apr. 11, 2006, and 2004/0116620, issued as U.S. Pat. No. 7,070,858 on Jul. 4, 2006. Sutures made from degradable suture material lose tensile strength as the material degrades. Degradable sutures can be in either a braided multifilament form or a monofilament form.

Non-degradable suture materials include, for example, polyamide (also known as nylon, such as nylon 6 and nylon 6,6), polyester (e.g., polyethylene terephthlate), polytetrafluoroethylene (e.g., expanded polytetrafluoroethylene), polyether-ester such as polybutester (block copolymer of butylene terephthalate and polytetra methylene ether glycol), polyurethane, metal alloys, metal (e.g., stainless steel wire), polypropylene, polyethelene, silk, and cotton. Sutures made of non-degradable suture material are suitable for applications in which the suture is meant to remain permanently in the body or is meant to be physically removed from the body after it has served its intended purpose.

Clinical Uses

In addition to the general wound closure and soft tissue repair applications, self-retaining sutures can be used in a variety of other indications.

Self-retaining sutures described herein may be used in various dental procedures, i.e., oral and maxillofacial surgical procedures and thus may be referred to as "self-retaining dental sutures." The above-mentioned procedures include, but are not limited to, oral surgery (e.g., removal of impacted or broken teeth), surgery to provide bone augmentation, surgery to repair dentofacial deformities, repair following trauma (e.g., facial bone fractures and injuries), surgical treatment of odontogenic and non-odontogenic tumors, reconstructive surgeries, repair of cleft lip or cleft palate, congenital craniofacial deformities, and esthetic facial surgery. Self-retaining dental sutures may be degradable or non-degradable, and may typically range in size from USP 2-0 to USP 6-0.

Self-retaining sutures described herein may also be used in tissue repositioning surgical procedures and thus may be referred to as "self-retaining tissue repositioning sutures". Such surgical procedures include, without limitation, face lifts, neck lifts, brow lifts, thigh lifts, and breast lifts. Self-retaining sutures used in tissue repositioning procedures may vary depending on the tissue being repositioned; for example, sutures with larger and further spaced-apart retainers may be suitably employed with relatively soft tissues such as fatty tissues.

Self-retaining sutures described herein may also be used in microsurgical procedures that are performed under a surgical microscope (and thus may be referred to as "self-retaining microsutures"). Such surgical procedures include, but are not limited to, reattachment and repair of peripheral nerves, spinal microsurgery, microsurgery of the hand, various plastic microsurgical procedures (e.g., facial reconstruction), microsurgery of the male or female reproductive systems, and various types of reconstructive microsurgery. Microsurgical reconstruction is used for complex reconstructive surgery problems when other options such as primary closure, healing by secondary intention, skin grafting, local flap transfer, and distant flap transfer are not adequate. Self-retaining microsutures have a very small caliber, often as small as USP 9-0, USP 10-0, USP 11-0 or USP 12-0, and may have an attached needle of corresponding size. The microsutures may be degradable or non-degradable.

Self-retaining sutures as described herein may be used in similarly small caliber ranges for ophthalmic surgical procedures and thus may be referred to as "ophthalmic self-retaining sutures". Such procedures include but are not limited to keratoplasty, cataract, and vitreous retinal microsurgical procedures. Ophthalmic self-retaining sutures may be degradable or non-degradable, and have an attached needle of correspondingly-small caliber. In addition, the self-retaining sutures can be used in a variety of veterinary applications for a wide number of surgical and traumatic purposes in animal health.

The present invention includes, in some embodiments and as described more fully herein, the self-retaining suture systems, and laser-cut retainers identified in the following numbered paragraphs:

A self-retaining suture thread wherein: the suture thread has an a surface and a central axis; a plurality of tissue retainers being distributed on the surface; wherein the plurality of tissue retainers each have at least one tissue engagement surface oriented at an acute angle to the central axis of the suture thread; and wherein the at least one tissue engagement surface is a laser-cut surface.

A self-retaining suture thread wherein:

the suture thread has an a surface and a central axis;

a plurality of tissue retainers being distributed on the surface;

wherein the plurality of tissue retainers each have a tip and at least one tissue engagement surface oriented at an acute angle to the central axis of the suture thread;

wherein the at least one tissue engagement surface is a laser-cut surface; and wherein the plurality of tissue retainers each have an entrance ramp from which a volume of material has been removed from the suture thread adjacent the tip of the retainer the entrance ramp being adapted to promote engagement of tissue by the tissue engagement surface of the retainer.

The self-retaining suture thread of paragraphs 148 and 149, wherein: the suture thread comprises a plurality of laser-cut slots which define said tissue retainers; each slots having a thickness from which material has been removed; and wherein the at least one tissue engagement surface of each of the plurality tissue retainers is defined by a laser-cut slot.

The self-retaining suture thread of paragraphs 148 and 149, wherein the suture thread is no greater than USP 2-0 in size.

The self-retaining suture thread of paragraphs 148 and 149, wherein the suture thread is no greater than USP 4-0 in size.

The self-retaining suture thread of paragraphs 148 and 149, wherein the suture thread is no greater than USP 6-0 in size.

The self-retaining suture thread of paragraphs 148 and 149, wherein the suture thread is no greater than USP 8-0 in size.

The self-retaining suture thread of paragraphs 148 and 149, wherein the suture thread is no greater than USP 10-0 in size.

A self-retaining suture comprising:

a suture thread having a plurality of slots wherein a volume of suture thread material has been removed, wherein each slot is oriented at an acute angle to a longitudinal axis of the suture thread and has an outer side and an inner side; and wherein the outer side of each slot define a tissue engagement surface of a tissue retainer.

The self-retaining suture of paragraph 156, wherein the plurality of slots are laser-cut.

The self-retaining suture of paragraph 156, wherein the inner side of each slot is approximately parallel to the outer side of each slot.

The self-retaining suture of paragraph 156, wherein the inner side of each slot is spaced from the outer side of each slot by approximately the same distance along the slot.

The self-retaining suture of paragraph 156, wherein the inner side of each slot is spaced from the outer side of each slot by approximately the same distance of 10 µm or less along the slot.

The self-retaining suture of paragraph 156, wherein the inner side of each slot is spaced from the outer side of each slot by approximately the same distance of 7 µm or less along the slot.

The self-retaining suture of paragraph 156, wherein the inner side of each slot is spaced from the outer side of each slot by approximately the same distance of 5 µm or less along the slot.

The self-retaining suture of paragraph 156, wherein the inner side of each slot is spaced from the outer side of each slot by approximately the same distance of 3 µm or less along the slot.

The self-retaining suture of paragraph 156, wherein the suture thread is of a size no greater than USP 4-0.

The self-retaining suture of paragraph 156, wherein the suture thread is of a size no greater than USP 6-0.

Although the present invention has been shown and described in detail with regard to only a few exemplary embodiments of the invention, it should be understood by those skilled in the art that it is not intended to limit the invention to the specific embodiments disclosed. Various modifications, omissions, and additions may be made to the disclosed embodiments without materially departing from the novel teachings and advantages of the invention, particularly in light of the foregoing teachings. Accordingly, it is intended to cover all such modifications, omissions, additions, and equivalents as may be included within the spirit and scope of the invention as defined by the following claims.

What is claimed is:

1. A method of making a self-retaining suture thread with a laser, comprising:
    (a) directing a laser beam toward a suture thread that extends along a longitudinal axis;
    (b) directing the laser beam along a first path relative to the longitudinal axis and thereby removing material from the suture thread along the first path;
    (c) directing the laser beam along a second path that is angled relative to the first path and thereby removing material from the suture thread along the second path, wherein the removal of the material along the first and second paths defines a slot in the suture thread that opens to an outer surface thereof, wherein the slot defines a tissue retainer of the self-retaining suture thread; and
    (d) maintaining a diameter of the laser beam while directing the laser beam along at least a portion of the first path such that the formed slot has an inner slot side and an outer slot side that is parallel to the inner slot side along at least a portion of the first path.

2. The method of claim 1, wherein the first path comprises a first linear path oriented at a first acute angle relative to the longitudinal axis, wherein the second path comprises a second linear path oriented at a second acute angle relative to the longitudinal axis.

3. A method of making a self-retaining suture thread with a laser, comprising:
    (a) removing material from a suture thread with a laser beam along a path and thereby forming a slot in the suture thread that opens to an outer surface of the suture thread, wherein the path comprises a first path portion and a second path portion angled relative to the first path portion; and
    (b) while removing the material from the suture thread along the path, maintaining a diameter of the laser beam such that at least a portion of the slot has opposed sides that are parallel to one another,
wherein the slot defines a tissue retainer of the self-retaining suture thread.

4. The method of claim 3, wherein at least a portion of the path is non-parallel to a longitudinal axis of the suture thread.

5. The method of claim 4, wherein the at least portion of the path is acutely angled relative to the longitudinal axis.

6. The method of claim 3, wherein removing material from the suture thread along the first path portion defines a first end of the slot, wherein removing material from the suture thread along the second path portion defines a second end of the slot that opens to the outer surface of the suture thread.

7. The method of claim 6, wherein the second path portion is acutely angled relative to a longitudinal axis of the suture thread.

8. The method of claim 6, wherein each of the first path portion and the second path portion is acutely angled relative to a longitudinal axis of the suture thread.

9. The method of claim 6, wherein at least one of the first path portion or the second path portion is linear.

10. The method of claim 3, wherein maintaining the diameter of the laser beam includes maintaining the diameter along the first path portion.

11. The method of claim 3, wherein at least a portion of the path is linear.

12. The method of claim 3, wherein the slot has a length measured parallel to a longitudinal axis of the suture thread and a depth measure transversely to the longitudinal axis, wherein the length is greater than the depth.

13. The method of claim 3, further comprising repeating steps (a) and (b) at least once and thereby forming a plurality of slots in the suture thread, wherein each of the slots defines a respective tissue retainer.

14. The method of claim 3, wherein removing the material from the suture thread with the laser beam along the path comprises moving the suture thread relative to the laser.

15. The method of claim 14, wherein moving the suture thread relative to the laser comprises moving the suture thread parallel to and transversely to a longitudinal axis defined by the suture thread.

16. The method of claim 3, further comprising stabilizing the suture thread with a stream of air while removing the material from the suture thread.

17. A method of making a self-retaining suture thread with a laser, comprising:
    (a) removing material from a suture thread with a laser beam along a first path;
    (b) removing material from the suture thread with the laser beam along a second path that is angled relative to the first path, thereby forming a slot in the suture thread that opens to an outer surface of the suture thread; and (c) while removing material from the suture thread, maintaining a diameter of the laser beam such that at least a portion of the slot has opposed sides that are parallel to one another, wherein the slot defines a tissue retainer of the self-retaining suture thread.

18. The method of claim 17, wherein each of the first path and the second path is angled relative to a longitudinal axis of the suture thread.

\* \* \* \* \*